United States Patent [19]

Robl

[11] Patent Number: 5,672,599
[45] Date of Patent: Sep. 30, 1997

[54] COMPOUNDS CONTAINING A FUSED BICYCLE RING

[75] Inventor: Jeffrey A. Robl, Newtown, Pa.

[73] Assignee: Bristol-Myers Squibb Co., Princeton, N.J.

[21] Appl. No.: 562,324

[22] Filed: Nov. 22, 1995

Related U.S. Application Data

[60] Division of Ser. No. 238,764, May 5, 1994, Pat. No. 5,508,272, which is a continuation-in-part of Ser. No. 77,978, Jun. 15, 1993, abandoned.

[51] Int. Cl.$^6$ ............ C07D 413/02; C07D 417/02; A61K 31/535; A61K 31/54

[52] U.S. Cl. ............ 514/227.2; 514/230.2; 514/80; 514/211; 514/230.5; 544/55; 544/92; 544/48; 544/91; 540/490; 562/556; 564/502; 564/503; 564/504; 564/505

[58] Field of Search ............ 514/258, 230.2, 514/227.2; 544/55, 92

[56] References Cited

U.S. PATENT DOCUMENTS

| | | | |
|---|---|---|---|
| 5,362,727 | 11/1994 | Robl | 514/214 |
| 5,504,080 | 4/1996 | Karanewsky | 514/214 |
| 5,508,272 | 4/1996 | Robl | 514/80 |
| 5,525,723 | 6/1996 | Robl | 540/521 |
| 5,552,397 | 9/1996 | Karanewsky et al. | 514/212 |

OTHER PUBLICATIONS

Baldwin et al., J. Chem. Soc. Chem. Commun., 1993, pp. 935–936.

Primary Examiner—Matthew V. Grumbling
Attorney, Agent, or Firm—Stephen B. Davis

[57] ABSTRACT

Compounds of the formula

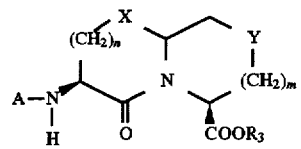

wherein X is O or S—$(O)_t$; n is one; m is zero or one; Y is $CH_2$, O, or S—$(O)_t$, provided that Y is O or S—$(O)_t$ only when m is one; and A is

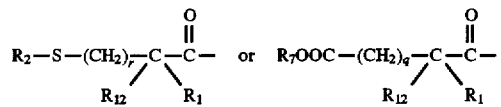

are dual inhibitors of NEP and ACE. Compounds wherein A is

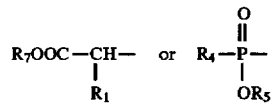

are selective ACE inhibitors. Also disclosed are methods of preparation and intermediates.

15 Claims, No Drawings

COMPOUNDS CONTAINING A FUSED BICYCLE RING

RELATED APPLICATION

This application is a division of Ser. No. 238,764 filed May 5, 1994, now U.S. Pat. No. 5,508,272 which is a continuation-in-part of Ser. No. 077,978 filed Jun. 15, 1993, now abandoned.

BACKGROUND OF THE INVENTION

Captopril, (S)-1-(3-mercapto-2-methyl-1-oxopropyl)-L-proline, having the structural formula

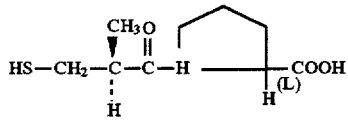

is an orally active angiotensin converting enzyme inhibitor useful for treating hypertension and congestive heart failure. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

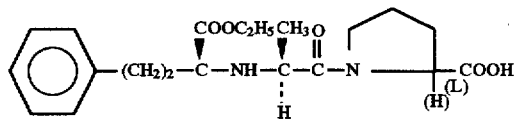

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S)-4-cyclohexyl-1-[[(R)-[(S)-1-hydroxy-2-methylpropoxy](4-phenylbutyl)phosphinyl]acetyl]-L-proline propionate (ester), sodium salt having the structural formula

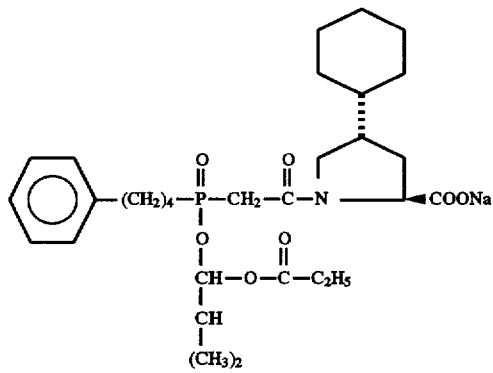

is also an orally active angiotensin converting enzyme inhibitor useful for treating hypertension. See Petrillo U.S. Pat. No. 4,337,201.

Haslanger et al. in U.S. Pat. No. 4,749,688 disclose treating hypertension by administering neutral metalloendopeptidase inhibitors alone or in combination with atrial peptides or angiotensin converting enzyme inhibitors.

Neustadt in U.S. Pat. No. 5,075,302 disclose that mercaptoacyl amino lactams of the formula

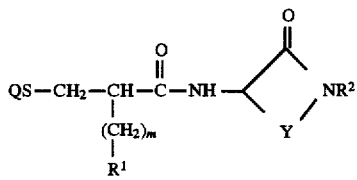

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt disclose employing such compounds alone or in combination with angiotensin converting enzyme inhibitors to treat cardiovascular diseases such as hypertension, congestive heart failure, edema, and renal insufficiency.

Delaney et al. U.K. Patent 2,207,351 disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al. in European Patent Application 481,522 disclose dual inhibitors of enkephalinase and angiotensin converting enzyme of the formulas

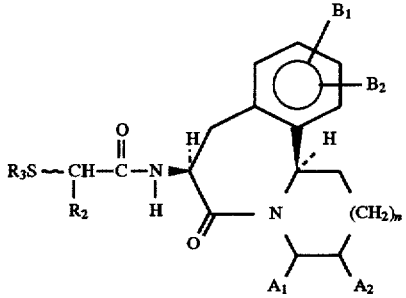

and

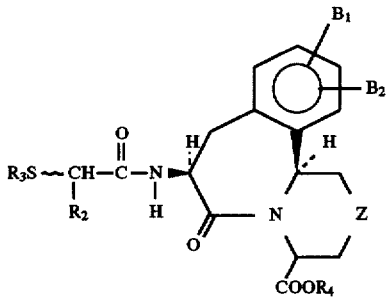

wherein n is zero or one and Z is O, S, —$NR_6$— or

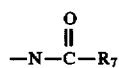

Additional tricyclic dual inhibitors are disclosed by Warshawsky et al. in European Patent Applications 534,363, 534,396 and 534,492.

Karanewsky et al. in U.S. Pat. Nos. 4,432,971 and 4,432,972 disclose phosphonamidate angiotensin converting enzyme inhibitors of the formula $$R_{21}-\underset{\underset{OR_3}{|}}{\overset{\overset{O}{\|}}{P}}-N-\underset{\underset{}{|}}{\overset{\overset{R_1}{|}}{C}}H-\overset{\overset{R_2}{|}}{C}-\overset{\overset{O}{\|}}{X}$$

wherein X is a substituted imino or amino acid or ester.

Karanewsky in U.S. Pat. No. 4,460,579 discloses angiotensin converting enzyme inhibitors including those of the formula $$R_7-\underset{\underset{OR_8}{|}}{\overset{\overset{O}{\|}}{P}}-NH-X-\overset{\overset{R_1}{|}}{C}H-\overset{\overset{O}{\|}}{C}-OR_2$$

and in U.S. Pat. No. 4,711,884 discloses angiotensin converting enzyme inhibitors including those of the formula $$R_3-\overset{\overset{O}{\|}}{C}-\underset{\underset{R_4}{|}}{C}H-NH-X-\overset{\overset{R_1}{|}}{C}H-\overset{\overset{O}{\|}}{C}-OR_2$$

wherein X is a thiazine or thiazepine.

SUMMARY OF THE INVENTION

This invention is directed to novel compounds containing a fused bicyclic ring which are useful as angiotensin converting enzyme inhibitors. Some of these compounds also possess neutral endopeptidase inhibitory activity. This invention is also directed to pharmaceutical compositions containing such selective or dual action inhibitors and the method of using such compositions. This invention is also directed to the process for preparing such novel compounds, novel intermediates, and processes for preparing such intermediates.

The novel fused bicyclic inhibitors of this invention include those compounds of the formula (I)

[Structure showing A—NH—C(O)—N cycle with (CH₂)ₙ—X group, (CH₂)ₘ—COOR₃ group]

and pharmaceutically acceptable salts thereof wherein:

A is $R_2-S-(CH_2)_r-\overset{R_{12}}{\underset{R_1}{C}}-\overset{\overset{O}{\|}}{C}-$, $R_7OOC-(CH_2)_q-\overset{R_{12}}{\underset{R_1}{C}}-\overset{\overset{O}{\|}}{C}-$, $R_7OOC-\underset{R_1}{CH}-$, or $R_4-\overset{\overset{O}{\|}}{\underset{\underset{OR_5}{|}}{P}}-$;

X is O or S—(O)ₜ; $R_1$ and $R_{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen, $$R_6-\overset{\overset{O}{\|}}{C}-,$$

or $R_{11}-S-$;

$R_3$, $R_5$ and $R_7$ are independently selected from hydrogen, alkyl, substituted alkyl, aryl-$(CH_2)_p-$, substituted aryl-$(CH_2)_p-$, heteroaryl-$(CH_2)_p-$, $-\underset{\underset{R_8}{|}}{C}H-O-\overset{\overset{O}{\|}}{C}-R_9,$ and $-CH_2-\text{[dioxolenyl with }R_{10}\text{]}$;

$R_4$ is alkyl, cycloalkyl-$(CH_2)_p-$, substituted alkyl, aryl-$(CH_2)_p-$, substituted aryl-$(CH_2)_p-$, or heteroaryl-$(CH_2)_p-$;

$R_6$ is alkyl, substituted alkyl, cycloalkyl-$(CH_2)_p-$, aryl-$(CH_2)_p-$, substituted aryl-$(CH_2)_p-$, or heteroaryl-$(CH_2)_p-$;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl-$(CH_2)_p-$;

$R_{11}$ is hydrogen, alkyl, substituted alkyl, cycloalkyl-$(CH_2)_p-$, aryl-$(CH_2)_p-$, substituted aryl-$(CH_2)_p-$, heteroaryl-$(CH_2)_p-$, or $-S-R_{11}$ completes a symmetrical disulfide wherein $R_{11}$ is

[Structure showing $-(CH_2)_r-C(R_{12})(R_1)-C(O)-N-$ attached to cyclic system with (CH₂)ₙ—X and (CH₂)ₘ—COOR₃]

m is zero or one;

Y is $CH_2$, S—(O)ₜ or O provided that Y is S—(O)ₜ or O only when m is one;

n is one or two;

p is zero or an integer from 1 to 6;

q is zero or an integer from 1 to 3;

r is zero or one; and t is zero, one, or two.

DETAILED DESCRIPTION OF THE INVENTION

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)₂, lower alkoxy, lower alkylthio, or carboxy.

The terms "lower alkoxy" and "lower alkylthio" refer to such lower alkyl groups as defined above attached to an oxygen or sulfur.

The term "cycloalkyl" refers to saturated rings of 3 to 7 carbon atoms with cyclopropyl, cyclobutyl, cyclopentyl, and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbons having one double bond.

The term "substituted alkenyl" refers to such straight or branched radicals of 3 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy.

The term "alkylene" refers to straight or branched chain radicals having up to seven carbon atoms, i.e. —CH$_2$—, —(CH$_2$)$_2$—, —(CH$_2$)$_3$—, —(CH$_2$)$_4$—,

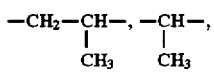

etc.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as

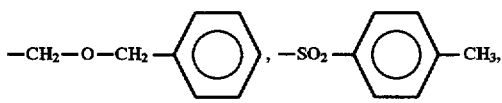

2,4-dinitrophenyl, lower alkyl, benzyl, or benzhydryl.

The compounds of formula I wherein

A is

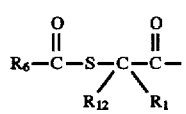

X, is O or S, and Y is CH$_2$, O, or S can be prepared by coupling the acylmercapto containing sidechain of the formula (II)

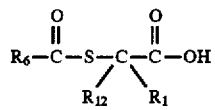

with a fused bicyclic ring compound of the formula

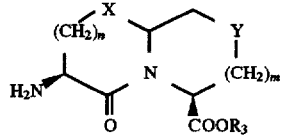

to give the product of the formula (IV)

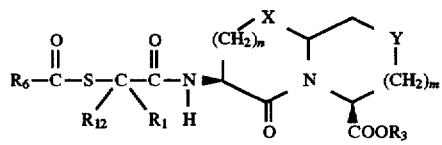

wherein R$_3$ is hydrogen or an acid protecting group such as methyl, ethyl, t-butyl, or benzyl. The above reaction can be performed in an organic solvent such as methylene chloride and in the presence of a coupling reagent such as 1-ethyl-3-(3-dimethylaminopropyl)carbodiimide, dicylcohexylcarbodiimide, benzotriazol-1-yloxytris(dimethylamino)phosphonium hexafluorophosphate, or carbonyldiimidazole. Alternatively, the acylmercapto carboxylic acid of formula II can be converted to an activated form prior to coupling such as an acid chloride, mixed anhydride, symmetrical anhydride, activated ester, etc.

The product of formula IV can be converted to the mercaptan product of formula I wherein R$_2$ is hydrogen and R$_3$ is hydrogen by methods known in the art. For example, when R$_6$ is methyl and R$_3$ is methyl or ethyl treatment with methanolic sodium hydroxide followed by aqueous acid yields the products wherein R$_2$ and R$_3$ are hydrogen.

The products of formula I wherein R$_2$ is hydrogen can be acylated with an acyl halide of the formula (V)

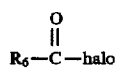

wherein halo is F, Cl or Br or acylated with an anhydride of the formula (VI)

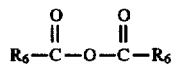

to give other products of formula I wherein R$_2$ is

The products of formula I wherein R$_2$ is —S—R$_{11}$ and R$_{11}$ is alkyl, substituted alkyl, cycloalkyl-(CH$_2$)$_p$—, aryl-(CH$_2$)$_p$—, substituted aryl-(CH$_2$)$_p$—, or heteroaryl-(CH$_2$)$_p$— can be prepared by reacting the products of formula I wherein R$_2$ is hydrogen with a sulfonyl compound of the formula

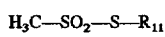  (VII)

in an aqueous alcohol solvent to yield the desired products. The compounds of formula VII are known in the literature or can be prepared by known methods, see for example, Smith et al., Biochemistry, 14, p 766–771 (1975).

The product of formula I wherein $R_2$ is SH can be prepared by reacting the product of formula I wherein $R_2$ is hydrogen with a compound of formula VII wherein $R_{11}$ is triphenylmethyl or trialkylsilyl followed by removal of the triphenylmethyl or trialkylsilyl group under acidic conditions.

The symmetrical disulfide products of formula I can be prepared by direct oxidation of the product of formula I wherein R2 is hydrogen with iodine according to known procedures, see, for example, Ondetti et al. U.S. Pat. No. 4,105,776.

The acylmercapto sidechain compounds of formula II wherein $R_{12}$ is hydrogen are described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, etc.

The acylmercapto sidechain compounds of formula II wherein $R_1$ and $R_{12}$ are both other than hydrogen and r is zero can be prepared by reacting the substituted carboxylic acid of the formula (VIII)

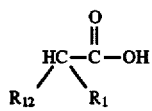

with bis[[(4-methoxy)phenyl]methyldisulfide in the presence of lithium diisopropylamide to give the compound of the formula (IX)

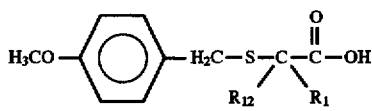

Treatment of the compound of formula IX with strong acid such as trifluoromethanesulfonic acid removes the methoxybenzyl protecting group and is followed by acylation with the acyl halide of formula V or anhydride of formula VI to give the compound of formula II wherein $R_1$ and $R_{12}$ are both other than hydrogen and r is zero.

Alternatively, the substituted carboxylic acid of formula VIII can be reacted with lithium diisopropyl amide and sulfur to give the mercaptan of the formula (X)

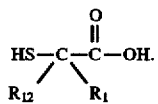

The mercaptan of formula X can then be acylated with the acyl halide of formula V or the anhydride of formula VI to give the compound of formula II wherein $R_1$ and $R_{12}$ are both other than hydrogen and r is zero.

The acylmercapto sidechain compounds of formula II wherein $R_1$ and $R_{12}$ are both other than hydrogen and r is one can be prepared by reacting the substituted carboxylic acid of the formula (XI)

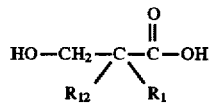

with para-toluenesulfonyl chloride in pyridine to give the lactam of the formula (XII)

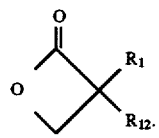

Treatment of the lactam of formula XII with a cesium thioacid of the formula (XIII)

in the presence of dimethylformamide yields the desired acylmercapto sidechain of formula II wherein $R_1$ and $R_{12}$ are both other than hydrogen and r is one. The compounds of formula I wherein A is

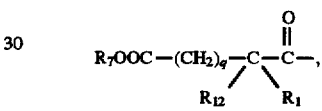

X is O or S, and Y is $CH_2$, O, or S can be prepared by coupling the acid of the formula (XIV)

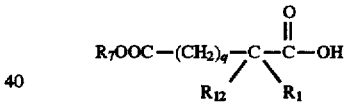

wherein $R_7$ is an acid protecting group with the fused bicyclic ring compound of formula III in the presence of a coupling reagent as defined above to give the product of the formula (XV)

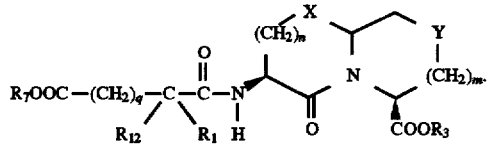

Alternatively, the acid of formula XIV can be converted to an activated form such as an acid chloride prior to the coupling reaction.

The acids of formula XIV are described by Warshawsky et al. in European Patent Application 534,396 and 534,492.

The compounds of formula I wherein A is

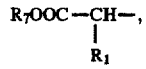

X is O or S, and Y is $CH_2$, O, or S can be prepared by reacting a keto acid or ester of the formula (XVI)

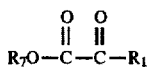

with a fused bicyclic ring compound of formula III under reducing conditions to give the product of the formula (XVII)

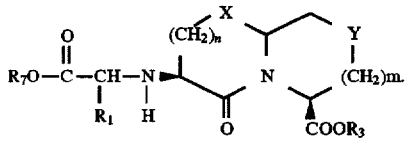

The keto acids and esters of formula XVI are described in the literature. See, for example, Ruyle U.S. Pat. No. 4,584,294 and Parsons et al. U.S. Pat. No. 4,873,235.

Alternatively, the fused bicyclic ring compound formula III can be reacted with a triflate of the formula (XVIII)

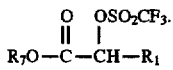

to give the product of formula XVII.

The compounds of formula I wherein A is

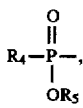

X is O or S, and Y is $CH_2$, O or S can be prepared by coupling a phosphonochloridate of the formula (XIX)

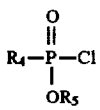

wherein $R_5$ is lower alkyl or benzyl with a fused bicyclic ring compound of formula III to give the product of the formula (XX)

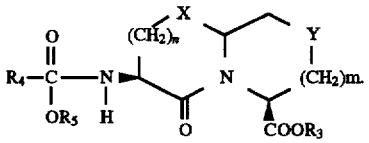

Preferably, $R_3$ in the compound of formula III is lower alkyl or benzyl. The $R_3$ and $R_5$ acid protecting groups can then be removed, for example, by hydrogenation to give the corresponding products of formula I wherein $R_3$ and $R_5$ are hydrogen.

The phosphonochloridates of formula XIX are known in the literature. See, for example, Karanewsky et al. U.S. Pat. Nos. 4,432,971 and 4,432,972 and Karanewsky U.S. Pat. No. 4,460,579.

The products of formula I wherein either X or Y or both are S—(O)$_t$ and t is one or two can be prepared by oxidation of the compounds of formulas IV, XV, XVII, or XX with a known oxidizing reagent such as meta chloroperbenzoic acid, peracetic acid, monoperoxyphthalic acid, magnesium salt hexahydrate, etc. By controlling the amount of oxidizing reagent and the time of the reaction, the products are obtained wherein t is one or two.

The ester products of formula I wherein $R_5$ or $R_7$ is

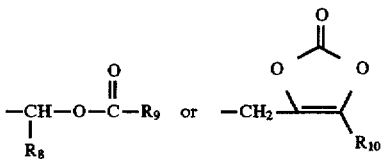

can be prepared by treating the corresponding compounds of formula I wherein $R_5$ or $R_7$ is hydrogen and $R_3$ is an acid protecting group with a compound of the formula (XXI)

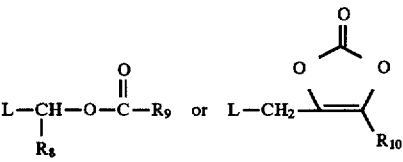

wherein L is a leaving group such as chloro, bromo, or tolylsulfonyloxy followed by removal of the $R_3$ ester protecting group.

The ester products of formula I wherein $R_3$ is

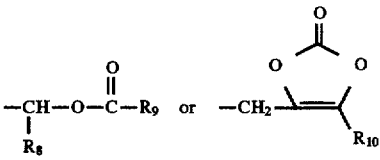

can be prepared by treating the corresponding compounds of formula I wherein $R_3$ is hydrogen and $R_2$ is

with a compound of formula XXI.

The fused bicyclic ring compounds of formula III can be prepared according to the following processes which also form part of this invention. For example, when Y is $CH_2$ an N-protected amino acid of the formula (XXII)

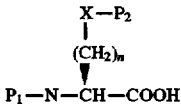

can be coupled with the amino acid ester of the formula (XXIII)

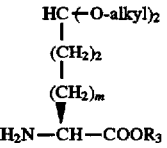

to give the dipeptide of the formula (XXIV)

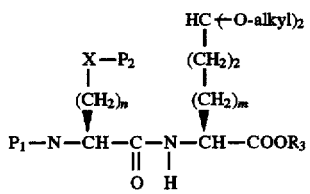

wherein $P_1$ is an amino protecting group such as benzyloxycarbonyl or t-butyloxycarbonyl or a group which together with the N-atom forms a protecting group such as phthalimido, $P_2$ is a hydroxy or mercapto protecting group, and $R_3$ is an easily removable ester protecting group. Preferred $P_2$ protecting groups when X is S are acyl groups such as acetyl or benzoyl, especially acetyl. Preferred $P_2$ protecting groups when X is O are acyl groups, tetrahydropyrans, hindered silyl groups and trityls, especially triphenylmethyl and 1,1-dimethylethyldimethylsilyl. This coupling reaction is preferably performed in the presence of a coupling reagent such as benzotriazol-1-yloxytris-(dimethylamino) phosphonium hexafluorophosphate, ethyl-3-(3-dimethylamino)propyl carbodiimide, or methanesulfonyloxybenzotriazole.

The $P_2$ protecting group can be selectively removed from the intermediate of formula XXIV such as by treatment with sodium methoxide in methanol when $P_2$ is acetyl or benzoyl or treatment with an acid such as p-toluenesulfonic acid in methanol when $P_2$ is acetyl, benzoyl, trityl, tetrahydropyranyl, or 1,1-dimethylethyldimethylsilyl. The resulting product is then subjected to an acid catalyzed cyclization reaction preferably by treating with a strong acid such as trifluoroacetic acid, para-toluenesulfonic acid or a commercially available polystyrene sulfonate polymer type ion exchange resin such as Amberlyst 15®. This cyclization reaction can be performed in a non-protic solvent such as methylene chloride or chloroform to give the intermediate of the formula (XXV)

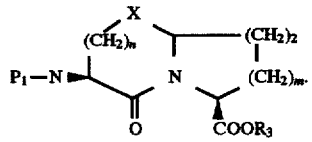

The compounds of formula XXIV after removal of the $P_2$ protecting group and prior to cyclization wherein X is O can be converted to the corresponding compounds wherein X is S. This can be done by various methods. For example, the compound of formula XXIV after removal of the $P_2$ group can be treated with triphenylphosphine, diisopropyl azodicarboxylate and thioacetic acid. The resulting thioacetate is then treated with sodium methoxide in methanol to give the corresponding mercaptan which can then be cyclized as described above.

In another method, the compound of formula XXIV after removal of the $P_2$ group is treated by known methods to give the compound of the formula (XXVI)

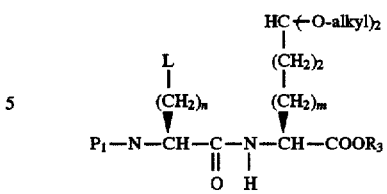

wherein L is a leaving group such as methanesulfonyloxy, para-toluenesulfonyloxy, iodo, or bromo. For example, treatment of the compound of formula XXIV after removal of the $P_2$ protecting group with methanesulfonyl chloride gives the compound of formula XXVI wherein L is methanesulfonyloxy.

The compound of formula XXVI is then treated with cesium thioacetate to give the correspopnding thioacetate. Treatment with sodium methoxide in methanol gives the corresponding mercaptan which can then be cyclized as described above.

Alternatively, the compound of formula XXIV wherein X is O can be converted directly to the intermediate of formula XXV by treatment with a strong acid such as trifluoroacetic acid, paratoluenesulfonic acid, or a commercially available polystyrene sulfonate polymer type ion exchange resin such as Amberlyst 15® in a suitable solvent such as methylene chloride or chloroform.

The N-protecting group is then removed from the compound of formula XXV, for example, by treatment with hydrazine monohydrate when $P_1$ together with N atom forms a phthalimido group or by treatment with iodotrimethylsilane or palladium on carbon and ammonium formate or hydrogen when $P_1$ is benzyloxycarbonyl or by treatment with hydrochloric acid in dioxane or other strong acid when $P_1$ is t-butoxycarbonyl to give the fused bicyclic ring compound of formula III.

In still another method when Y is $CH_2$, the N-protected amino acid of formula XXII can be coupled with the hydroxy amino acid ester of the formula (XXVII)

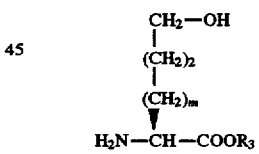

to give the dipeptide of the formula (XXVIII)

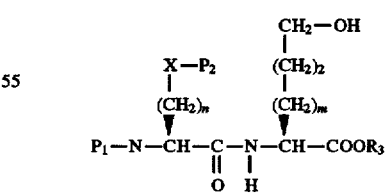

wherein $P_1$ and $P_2$ are as defined above. This coupling reaction is preferably performed in the presence of a coupling reagent such as methanesulfonyloxybenzotriazole or ethyl-3-(dimethylamino)propyl carbodiimide.

Hydroxy compound XXVIII is then oxidized to the aldehyde of the formula (XXIX)

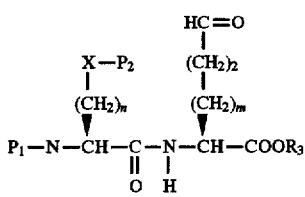

by treating with oxalyl chloride/dimethylsulfoxide followed by a tertiary amine in a non-protic solvent such as methylene chloride. The aldehyde of formula XXIX is then treated as described above to remove the $P_2$ protecting group and then subjected to an acid catalyzed cyclization reaction as described above to give the intermediate of formula XXV.

The starting material of formula XXIII wherein m is one can be prepared by selective protection of the N-atom of L-ε-hydroxynorleucine to give

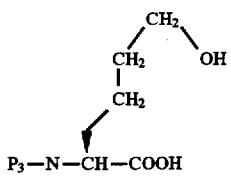

wherein $P_3$ is an N-protecting group. For example, $P_3$ and the N-atom can form a phthalimido moiety. The N-protected L-ε-hydroxynorleucine of formula XXX is then treated to introduce the $R_3$ acid protecting group such as by treatment with methyl iodide in the presence of base or by treatment with a strong acid in methanol wherein $R_3$ is methyl. This ester is then oxidized to give the aldehyde of the formula (XXXI)

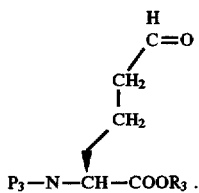

The aldehyde of formula XXXI is then treated with the orthoformate of the formula (XXXII)

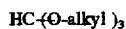

in the presence of a strong acid catalyst and the corresponding alcohol, i.e. HO-alkyl wherein alkyl is the same as in the orthoformate of formula XXXII, to give (XXXIII)

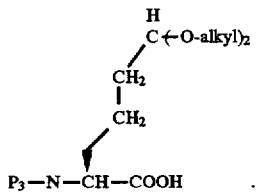

Removal of N-protecting group $P_3$ such as by treatment with hydrazine hydrate when $P_3$ and the N-atom forms a phthalimido moiety yields the starting material of formula XXIII wherein m is one.

The starting material of formula XXIII wherein m is zero can be prepared by protecting the N-atom of γ-benzyl glutamate to give (XXXIV)

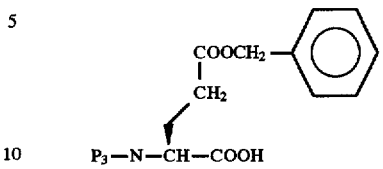

wherein $P_3$ is an N-protecting group such as t-butyloxycarbonyl or where $P_3$ and the N-atom can form a phthalimido moiety. The N-protected glutamic acid of formula XXXIV is then treated to introduce the $R_3$ acid protecting group, as described above, to give (XXXV)

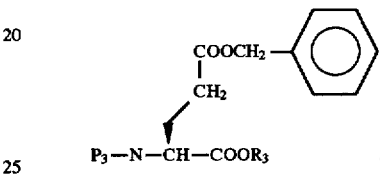

Hydrogenolysis when $R_3$ is lower alkyl removes the benzyl ester group from compound XXXV to give (XXXVI)

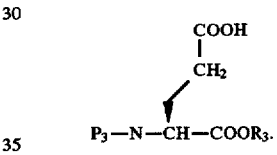

Selective reduction of compound XXXVI such as by treatment with ethanethiol, ethyl-3-(3-dimethlamino)propyl carbodiimide, and dimethylaminopyridine followed by triethylsilane, palladium on carbon, and acetonitrile gives the aldehyde of the formula (XXXVII)

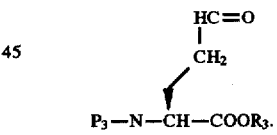

The aldehyde of formula XXXVII is then treated with the orthoformate of formula XXXII as described above and the N-protecting group $P_3$ is removed as described above to give the starting material of formula XXIII wherein m is zero.

The hydroxy amino acid ester starting material of formula XXVII can be prepared by reacting a solution of diethyl acetamidomalonate with a stirred suspension of sodium hydride followed by reaction with a haloalkylacetate of the formula (XXXVIII)

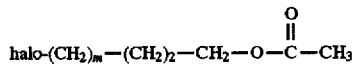

wherein halo is Br, I, or Cl to give the compound of the formula (XXXIX)

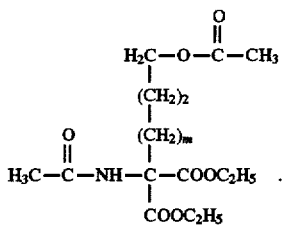

A solution of the diethyl ester of formula XXXIX is treated with sodium hydroxide and heat and then acidified and heated again to give the hydroxy amino acid of the formula (XL)

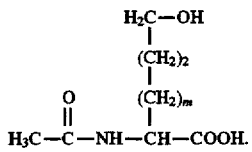

The hydroxy amino acid of formula XL is then treated with porcine kidney acylase or other suitable hydrolyzing enzyme to give the resolved hydroxy amino acid of the formula (XLI)

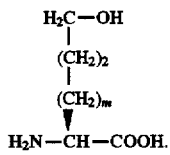

The hydroxy amino acid of formula XLI is then converted to the ester of formula XXVII by conventional means. For example, the hydroxy amino acid of formula XLI can be treated in methanol with trimethylsilyl chloride to give the hydrochloride salt of the methyl ester of formula XXVII.

The starting materials of formula XXII can be prepared as follows. When X is O, the hydroxy α-amino acid of the formula (XLII)

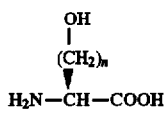

is reacted to introduce the $P_1$ and $P_2$ protecting groups. For example, treatment of the acid of formula XLII with N-carbethoxyphthalimide in the presence of sodium carbonate followed by treatment with chlorotriphenylmethane and triethylamine gives the starting material of formula XXII wherein X is O, $P_1$ together with N-atom forms a phthalimido, and $P_2$ is trityl. Alternatively, treatment of the acid of formula XLII with N-(benzyloxycarbonyloxy) succinimide in aqueous sodium carbonate and acetone followed by treatment with t-butyldimethylsilyl chloride or an acylating agent of formula V or VI gives the starting material of formula XXII wherein X is O, $P_1$ is benzyloxycarbonyl, and $P_2$ is t-butyldimethylsilyl or an acyl group such as acetyl.

When X is S and n is one, N,N'-bis[(phenylmethoxy) carbonyl]-L-cystine can be treated with zinc dust and aqueous sulfuric acid to give the mercaptan of the formula (XLIII)

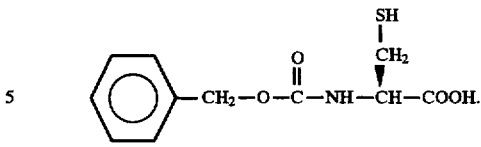

The mercaptan of formula XLIII is then treated to introduce the $P_2$ protecting group. For example, treatment of the mercaptan of formula XLIII with acetic anhydride gives the starting material of formula XXII wherein X is S, n is one, $P_2$ is acetyl, and $P_1$ is benzyloxycarbonyl.

When X is S and n is two, L-methionine can be protected on the N-atom. For example, reaction with benzyl chloroformate or N-(benzyloxycarbonyloxy)succinimide gives N-[(phenylmethoxy)carbonyl]-L-methionine which is then esterified by treatment with an alcohol, alkyl-OH, in the presence of an acid catalyst such as p-toluenesulfonic acid. Treatment with an oxidizing agent such as N-chlorosuccinimide in aqueous solvent gives the sulfoxide of the formula (XLIV)

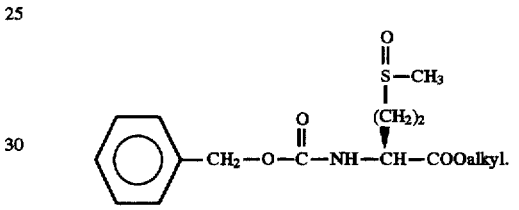

The sulfoxide of formula XLIV is then treated with an acid anhydride such as acetic anhydride to give the compound of the formula (XLV)

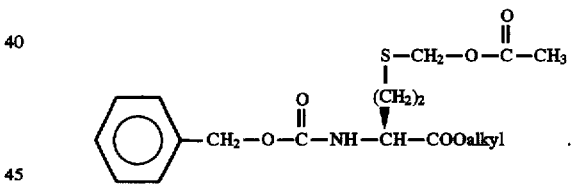

Treatment with alkali metal hydroxide, followed by the removal of formaldehyde such as by treatment with a reducing agent, for example, sodium borohydride, followed by treatment with an acid anhydride such as acetic anhydride gives the starting material of formula XXII wherein X is S, n is two, $P_2$ is acetyl, and $P_1$ is benzyloxycarbonyl.

The fused bicyclic ring compounds of formula III wherein Y is S or O and m is one can be prepared by coupling the N-protected amino acid of formula XXII with the amino acid ester of the formula (XLVI)

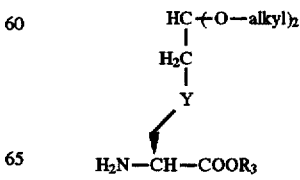

to give the dipeptide of the formula (XLVII)

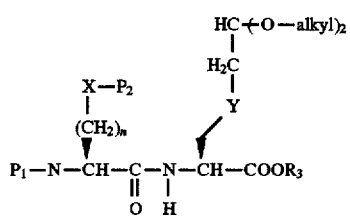

wherein $P_1$ and $P_2$ are as defined previously and $R_3$ is an acid protecting group. This coupling reaction is preferably performed in the presence of a coupling reagent such as benzotriazol-1-yloxytris(dimethylamino)phosphonium hexafluorophosphate or ethyl-3-(3-dimethylamino)propyl carbodiimide.

The $P_2$ protecting group can be selectively removed from the intermediate of formula XLVII such as by treatment with sodium methoxide in methanol when $P_2$ is an acyl group such as acetyl or benzoyl and treatment with an acid such as p-toluenesulfonic acid in methanol when $P_2$ is a trityl, tetrahydropyranyl, or a hindered silyl group. The resulting product is then subjected to an acid catalyzed cyclization reaction as described above to give the intermediate of the formula (XLVIII)

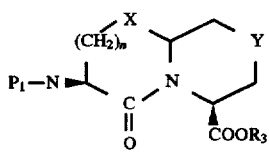

The intermediate of formula XLVIII wherein X is S and n is two can also be prepared by treating the compound of formula XLVII wherein X is O and n is two to selectively remove the $P_2$ group and convert the hydroxy to a mercaptan as described above followed by acid catalyzed cyclization.

The N-protecting group is then removed from the compound of formula XLVIII for example, by treatment with hydrazine monohydrate when $P_1$ together with N atom forms a phthalimido group or by treatment with iodotrimethylsilane or palladium on carbon and ammonium formate or hydrogen when $P_1$ is benzyloxycarbonyl to give the fused bicyclic ring compounds of formula III.

The starting material of formula XLVI wherein Y is O can be prepared by reacting the N-phthalimino protected amino acid ester of the formula (XLIX)

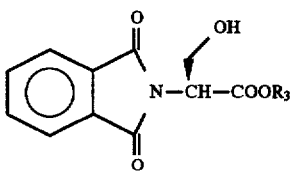

with allyl trichloroacetimidate in the presence of trifluoromethanesulfonic acid to give the compound of the formula (L)

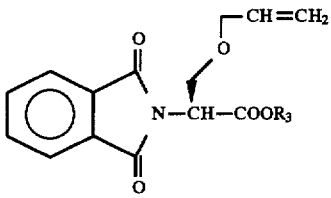

Treatment of the compound of formula L with ozone in methanol then dimethylsulfide followed by the orthoformate of formula XXXII in the presence of p-toluenesulfonic acid yields the protected compound of the formula (LI)

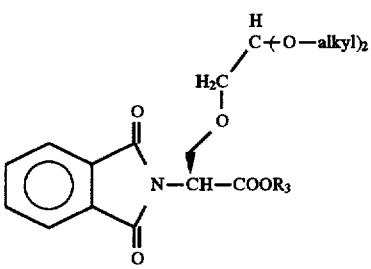

Removal of the N-protecting group such as by treatment with hydrazine hydrate yields the starting material of formula XLVI wherein Y is O.

The starting material of formula XLVI wherein Y is S can be prepared by reacting the cysteine ester of the formula (LII)

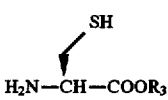

with the bromoacetal of the formula $$BR-CH_2-CH-(O\text{-alkyl})_2 \qquad (LIII)$$

in the presence of sodium hydride and potassium iodide to give the amino acid ester of the formula (LIV)

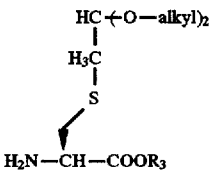

The compounds of formula I contain three asymmetric centers in the fused bicyclic portion of the structure with additional centers possible in the side chain. While the optically pure form of the fused bicyclic products described above is preferred, all such forms are within the scope of this invention. The above described processes can utilize racemates, enantiomers, or diastereomers as starting materials. When diastereomeric compounds are prepared, they can be separated by conventional chromatographic or fractional crystallization methods. Preferably, the hydrogen attached to the bridgehead carbon is in the orientation shown below

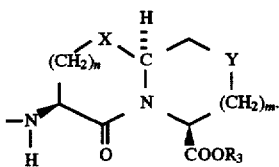

The compounds of formula I wherein $R_3$, $R_5$ and/or $R_7$ are hydrogen can be isolated in the form of a pharmaceutically acceptable salt. Suitable salts for this purpose are alkali metal salts such as sodium and potassium, alkaline earth metal salts such as calcium and magnesium, salts derived from amino acids such as arginine, lysine, etc. and salts derived from amines such as alkylamines, e.g. t-butylamine, t-amylamine, etc., substituted alkylamines, e.g. benzylamine, dialkylamines, substituted dialkylamines, e.g. N-methyl glucamine, trialkylamines, substituted trialkylamines, and quaternary ammonium salts. These salts can be obtained by reacting the acid form of the compound with a base supplying the desired ion in a medium in which the salt precipitates or in aqueous medium and then lyophilizing.

Preferred compounds of this invention are those wherein:

A is

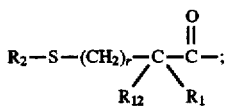

$R_2$ is hydrogen,

or $R_{11}$—S—;

$R_3$ is hydrogen or lower alkyl of 1 to 4 carbons;

r is zero or one;

$R_{11}$ is lower alkyl of 1 to 4 carbons;

$R_1$ is aryl-$CH_2$—, substituted aryl-$CH_2$—, heteroaryl-$CH_2$—, cycloalkyl-$CH_2$— wherein the cycloalkyl is of 3 to 7 carbons, or straight or branched chain alkyl of 1 to 7 carbons and $R_{12}$ is hydrogen; or $R_1$ and $R_{12}$ taken together with the carbon to which they are attached complete a cycloalkyl ring of 5 to 7 carbons;

$R_6$ is lower alkyl of 1 to 4 carbons or phenyl;

n is one or two;

m is zero or one;

X is O or S; and

Y is $CH_2$, O, or S provided that Y is O or S only when m is one.

Most preferred are the above compounds wherein:

$R_2$ is hydrogen or

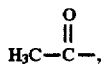

especially hydrogen;

$R_3$ is hydrogen;

r is zero or one; especially one;

$R_1$ is benzyl, cyclopropylmethyl, or straight or branched chain alkyl of 3 to 5 carbons, especially benzyl;

$R_{12}$ is hydrogen;

n is one or two;

m is zero or one;

X is O or S; and

Y is $CH_2$, O, or S provided that Y is O or S only when m is one.

The single most preferred compound is [4S-[4α(R*),7α,10aβ]]-octahydro-4-[(2-mercapto-1-oxo-3-phenylpropyl)amino]-5-oxo-7H-pyrido[2,1-b]-[1,3]thiazepine-7-carboxylic acid, i.e. the compound of the formula

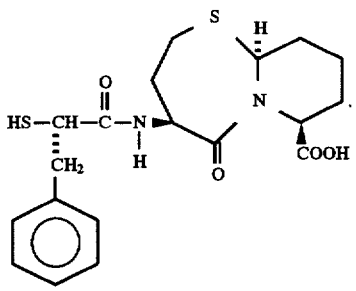

The compounds of formula I wherein A is

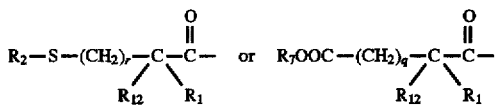

are dual inhibitors possessing the ability to inhibit angiotensin converting enzyme and neutral endopeptidase. The compounds of formula I wherein A is

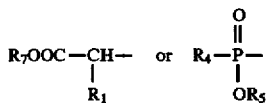
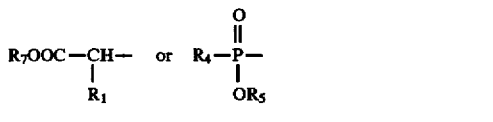

are selective inhibitors possessing the ability to inhibit the angiotensin converting enzyme. Thus, the compounds of formula I including their pharmaceutically acceptable salts are useful in the treatment of physiological conditions in which angiotensin converting enzyme inhibitors have been shown to be useful. Such conditions include disease states characterized by abnormalities in blood pressure, intraocular pressure, and renin including cardiovascular diseases particularly hypertension and congestive heart failure, glaucoma, and renal diseases such as renal failure, diabetic nephropathy, and renal impairment following treatment with cyclosporine or other immunosuppressants. Other conditions in which angiotensin converting enzyme inhibitors have been reported to be useful include hepatic cirrhosis, inhibiting the progression of atherosclerosis, preventing or treating hypertensive or diabetic retinopathy, improving myocardial dysfunction during or following a myocardial infarction, and preventing restinosis after angioplasty. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases, glaucoma, as well as the relief of acute or chronic pain. Thus, the compounds of formula I are useful in reducing blood pressure and the dual inhibitors of formula I are additionally useful for this purpose due to their diuresis and natriuresis properties. The dual inhibitors are particularly useful in the treatment of congestive heart failure.

The compounds of formula I including pharmaceutically acceptable salts thereof can be administered for these effects in amounts similar to those employed previously for angiotensin converting enzyme inhibitors. For example, the compounds of formula I can be administered to a mammalian host such as man at from about 0.1 mg. to about 100 mg. per kg. of body weight per day, preferably from about 0.5 mg. to about 25 mg. per kg. of body weight per day. The compounds of formula I are preferably administered orally but parenteral routes such as subcutaneous, intramuscular, and intravenous can also be employed as can topical routes of administration. The daily dose can be administered singly or can be divided into two to four doses administered throughout the day.

The inhibitors of formula I can be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The inhibitors of formula I can be administered in combination with other classes of pharmaceutically active compounds. For example, a diuretic, a calcium channel blocker, a potassium channel activator, a cholesterol reducing agent, a β-blocker, etc.

The inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

[4S-[4α(R*),7α,10aβ]]-Octahydro-4-[(2-mercapto-1-oxo-3-phenylpropyl)amino]-5-oxo-7H-pyrido[2,1-b][1,3]oxazepine-7-carboxylic acid a) (S)-2-Phthalimido-4-hydroxybutanoic acid, triethylamine salt

A solution of L-homoserine (3.0 g., 25.2 mmol.) and sodium carbonate (2.670 g., 25.2 mmol.) in water (60 ml.) was treated with N-carbethoxyphthalimide (5.570 g., 25.4 mmol.). After stirring at room temperature for 2 hours, the solution was acidified with 6N hydrochloric acid and extracted into ethyl acetate. The ethyl acetate extract was washed with brine, dried (sodium sulfate), and filtered into a solution of triethylamine (4.0 ml.) in methylene chloride (40 ml.). The cloudy solution was concentrated and triturated with ethyl acetate and ethyl ether to afford 5.11 g. of the title compound as a white solid; m.p. 142°–144° C. TLC (5% acetic acid in ethyl acetate) $R_f$=0.36; $[\alpha]_D$=–6.2° (c=0.8, chloroform).

Anal. calc'd. for $C_{18}H_{26}N_2O_5$: C 61.70; H 7.48; N 7.99 Found: C 61.45; H 7.47; N 7.84.

b) (S)-2-Phthalimido-4-(triphenylmethoxy)butanoic acid, triethylamine salt

A homogeneous solution of the product from part (a) (1.890 g., 5.4 mmol.) in chloroform (20 ml.) was treated with triethylamine (80 μL) followed by solid chlorotriphenylmethane (1.590 g., 5.70 mmol.). After stirring at room temperature for 2.5 hours, the solution was partitioned between ethyl acetate and 0.1N hydrochloric acid (150 ml.). The organic layer was washed with water and brine, then dried (sodium sulfate) and filtered into a solution of triethylamine (1.0 ml.) in methylene chloride (30 ml.). The solution was concentrated to an oil, redissolved in a small amount of methylene chloride and ethyl acetate and triturated with ethyl ether until the solution became turbid. The mixture was seeded and let stand at room temperature. The resulting precipitate was collected by filtration, washed with ethyl acetate and ethyl ether, and dried in vacuo to afford 2.538 g. of the title compound as a white solid; m.p.=165°–170° C. (decomp.). TLC (10% methanol in chloroform) $R_f$=0.23; $[\alpha]_D$=+7.0° (c=1.2, chloroform).

c) (S)-2-Phthalimido-6-hydroxyhexanoic acid

A solution of (+)-L-ε-hydroxynorleucine [prepared according to the procedure of Bodanszky et al., J. Med Chem., 1978, 21, 1030–1035] (1.030 g., 7.0 mmol.) and sodium carbonate (745 mg., 7.0 mmol.) in water (12 ml.) was treated with N-carbethoxyphthalimide (1.495 g., 7.0 mmol.) and the mixture was stirred at room temperature for 2 hours. The solution was filtered, cooled to 0° C., and acidified with 6N hydrochloric acid to afford a white precipitate. The solid was collected by filtration and dried in vacuo at 80° C. for one hour to give 1.297 g. of the title compound; m.p. 162°–163° C.; $[\alpha]_D$=–35.7° (c=1.3, methanol).

d) (S)-2-Phthalimido-6,6-dimethoxyhexanoic acid, methyl ester

A slurry of the product from part (c) (3.752 g., 13.5 mmol.) and cesium carbonate (2.178 g., 6.7 mmol.) in dimethylformamide (44 ml.) was treated with methyl iodide (3.0 ml., 6.84 g., 48.2 mmol.). After stirring at room temperature for 2 hours, the mixture was diluted with ethyl acetate and washed successively with water containing a small amount of sodium bisulfite, water, 50% saturated sodium bicarbonate, and brine, then dried (sodium sulfate), filtered and stripped to give the intermediate ester as a colorless oil (3.825 g.). The oil was homogeneous by TLC (1:1-acetone:hexanes) $R_f$=0.37.

A –78° C. solution of oxalyl chloride (1.37 ml., 2.00 g., 15.7 mmol.) in dry methylene chloride (58 ml.) was treated dropwise with a solution of dry dimethylsulfoxide (2.24 ml., 2.47 g., 31.6 mmol.) in methylene chloride (2 ml.). After 10 minutes, a solution of the above alcohol-ester (3.825 g., 13.1 mmol.) in methylene chloride (10 ml.) was added. After an additional 15 minutes, triethylamine (8.0 ml.) was added and the mixture was stirred at –78° C. for 5 minutes, then warmed to 0° C. The mixture was diluted with ethyl acetate/ethyl ether and was subsequently washed with 1N hydrochloric acid, water, and brine, then dried (sodium sulfate), filtered and stripped to give the crude desired aldehyde. The oil was homogeneous by TLC (1:1-acetone:hexanes) $R_f$=0.48.

A solution of the above aldehyde in methanol (17 ml.) and methylene chloride (17 ml.) was treated with trimethyl orthoformate (1.7 ml.) followed by p-toluenesulfonic acid monohydrate (180 mg.). The mixture was stirred at room temperature for 1.5 hours, then partitioned between ethyl acetate and 50% saturated sodium bicarbonate. The organic layer was washed with water and brine, then dried (sodium sulfate), flitered and stripped. The residue was flash chromatographed (Merck silica gel, 1:1-ethyl acetate:hexanes) and the pure product fractions were crystallized from ethyl acetate/hexanes to give the analytically pure title product (3.452 g., first crop and 215 mg., second crop) as white needles; m.p. 69°–70° C. TLC (1:1-ethyl acetate:hexanes) $R_f$=0.35; $[\alpha]_D$=–27.4° (c=1.5, chloroform).

Anal. calc'd. for $C_{17}H_{21}NO_6$: C 60.89; H 6.31; N 4.18 Found C 60.80; H 6.32; N 4.16.

e) [S-(R*,R*)]-2-[[2-Phthalimido-4-(triphenylmethoxy)-1-oxobutyl]amino]-6,6-dimethoxyhexanoic acid, methyl ester A slurry of the product from part (d) (2.540 g., 7.57 mmol.) in methanol (18 ml.) was treated with hydrazine monohydrate (378 µL, 390 mg, 7.80 mmol.). The mixture became homogeneous within 10 minutes. After stirring at room temperature for 3 days, the resulting slurry was filtered, stripped, slurried in methylene chloride, filtered and stripped again to afford the crude intermediate amine as a colorless oil. Meanwhile a solution of the triethylamine salt product from part (b) (4.622 g., 7.80 mmol.) in methylene chloride (50 ml.) at 0° C. was treated with benzotriazol-1-yloxytris(dimethylamino)phosphonium hexafluorophosphate (3.519 g., 7.95 mmol.). The mixture was stirred for 35 minutes, then treated with a solution of the above amine in methylene chloride (15 ml.). After 10 minutes at 0° C. and 2 hours at room temperature, the solution was partitioned between ethyl ether and water. The organic layer was washed with 50% saturated sodium bicarbonate and brine, then dried (sodium sulfate), filtered and stripped. The residue was flash chromatographed (Merck silica gel, 6:4-ethyl acetate:hexanes) to give 3.580 g. of pure title compound as a white foam. TLC (6:4-ethyl acetate:hexanes) $R_f$=0.32; $[\alpha]_D$=+26.2° (c=0.6, chloroform).

f) [S-(R*,R*)]-2-[(2-Phthalimido-4-hydroxy-1-oxobutyl)amino]-6,6-dimethoxyhexanoic acid, methyl ester A solution of the product from part (e) (5.420 g., 8.0 mmol.) in methanol (60 ml.) was treated with p-toluenesulfonic acid monohydrate (520 mg.). After stirring at room temperature for 1.5 hours, the mixture was partitioned between ethyl acetate and dilute sodium bicarbonate. The phases were separated and the aqueous layer was extracted again with ethyl acetate. The pooled organic extracts were washed with brine, dried (sodium sulfate), filtered and stripped. The residue was flash chromatographed (Merck silica gel, 8:2-ethyl acetate:hexanes followed by 5% methanol in ethyl acetate) to afford 2.860 g. of the title product as a colorless oil. TLC (7:3-ethyl acetate:hexanes) $R_f$=0.26; $[\alpha]_D$=+18.7° (c=1.3, chloroform).

g) [4S-(4α,7α,10aβ)]-Octahydro-4-phthalimido-5-oxo-7H-pyrido[2,1-b][1,3]oxazepine-7-carboxylic acid, methyl ester A solution of the product from part (f) (2.10 g., 4.95 mmol.) in methylene chloride (100 ml.) was treated with Amberlyst® 15 ion exchange resin (240 mg., pre-washed successively with 6N hydrochloric acid, water, tetrahydrofuran, then methylene chloride). After stirring at room temperature for 2.5 hours, the solution was filtered, stripped and flash chromatographed (Merck silica gel, 6:4-ethyl acetate:hexanes followed by 100% ethyl acetate) to give 1.40 g. of title product as a white foam.

h) (S)-2-(Acetylthio)benzenepropanoic acid

Sodium nitrite (10.3 g., 280 mmol.) was added to a solution of D-phenylalanine (30.0 g., 181 mmol.) and potassium bromide (73.5 g.) in sulfuric acid (2.5N, 365 ml.) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g. of (R)-2-bromo-3-benzenepropanoic acid; b.p. 141° C. (0.55 mm. of $[\alpha]_D$=+14.5° (c=2.4, chloroform).

A mixture of thioacetic acid (7 ml., 97.9 mmol.) and potassium hydroxide (5.48 g., 97.9 mmol.) in acetonitrile (180.5 ml.) was stirred under argon at room temperature for 1¾ hours. The mixture was cooled in an ice-bath, and a solution of (R)-2-bromo-3-benzenepropanoic acid (20.4 g., 89 mmol.) in acetonitrile (20 ml.) was added over a ten minute period. The reaction was stirred under argon at room temperature for 5 hours, filtered, and the acetonitrile was removed in vacuo. The oily residue was redissolved in ethyl acetate and washed with 10% potassium bisulfate and water. Removal of the ethyl acetate in vacuo afforded 19.6 g. of crude product. The crude product was purified via its dicyclohexylamine salt using isopropyl ether as solvent for crystallization. An analytical sample of (S)-2-(acetylthio)benzenepropanoic acid, dicyclohexylamine salt was prepared by recrystallization from ethyl acetate; m.p. 146°–147° C.; $[\alpha]_D$=–39.6° C. (c=1.39, chloroform).

Anal. calc'd. for $C_{11}H_{12}O_3S \cdot C_{12}H_{23}N$: C,68.11; H,8.70; N,3.45; S,7.91 Found: C,67.93; H,8.71; N,3.37; S,7.94.

The free acid was regenerated by partitioning the dicyclohexylamine salt between 5% potasssium bisulfate and ethyl acetate to yield (S)-2-(acetylthio)benzenepropanoic acid; $[\alpha]_D$=–70.1° C. (c=1.91, chloroform).

Anal. calc'd. for $C_{11}H_{12}O_3S$: C,58.91; H,5.39; S,14.30 Found: C,58.73; H,5.41; S,14.53.

i) [4S-[4α(R*),7α,10aβ]]-Octahydro-4-[[2-(acetylthio)-1-oxo-3-phenylpropyl]amino]-5-oxo-7H-pyrido[2,1-b][1,3]oxazepine-7-carboxylic acid, methyl ester The product from part (g) (620 mg., 1.66 mmol.) in methanol (10 ml.) was treated with hydrazine monohydrate (85 µL, 88 mg., 1.75 mmol.) and the solution was stirred at room temperature for 44 hours. The mixture was filtered and the solid was washed with methanol. The filtrate was stripped, triturated with methylene chloride, filtered again and stripped to give the crude amine as a cloudy oil (about 400 mg.).

A cold (0° C.) solution of (S)-2-(acetylthio)benzenepropanoic acid (410 mg., 1.83 mmol.) and triethylamine (250 µL, 182 mg., 1.80 mmol.) in methylene chloride (10 ml.) was treated with the above amine (as a solution in 8 ml. methylene chloride) followed by benzotriazol-1-yloxytris(dimethylamino)phosphonium hexafluorophosphate (808 mg, 1.83 mmol.). The clear, nearly colorless solution was stirred at 0° C. for 40 minutes and then at room temperature for 2 hours. The mixture was partitioned between ethyl acetate/ethyl ether and water. The organic layer was washed successively with 50% saturated sodium bicarbonate and brine, then dried (sodium sulfate), filtered and stripped. The residue was flash chromatographed (Merck silica gel, 60–70% ethyl acetate in hexanes) to give 602 mg., of pure title product as a white foam; TLC (6:4-ethyl acetate:hexanes) $R_f$=0.27.

j) [4S-[4α(R*),7α,10aβ]]-Octahydro-4-[(2-mercapto-1-oxo-3-phenylpropyl)amino]-5-oxo-7H-pyrido[2,1-b][1,3]oxazepine-7-carboxylic acid A 0° C. solution of the product from part (i) (590 mg., 1.32 mmol.) in methanol (10 ml., de-oxygenated via argon bubbling) was treated with 1N sodium hydroxide (7 ml., de-oxygenated via argon bubbling). After stirring for 15 minutes, the solution was warmed to room temperature and stirring under argon was continued for an additional 4.5 hours. The mixture was acidified with 5% potassium bisulfate, diluted with water and extracted with ethyl acetate. The ethyl acetate extract was washed with water and brine, then dried (sodium sulfate), filtered and concentrated to approximately 3 ml. The residue was slurried in ethyl acetate and a little hexane and the resulting solid was collected by filtration and dried in vacuo to give 413 mg. of the title product; m.p. 180.5° C. (decomp.). TLC (2% acetic acid in ethyl acetate) $R_f$=0.39; $[\alpha]_D$=−37.6° (c=0.36, methanol).

HPLC: YMC S3 ODS column (6.0×150 mm); eluted with 40% A: 90% water–10% methanol–0.2% phosphoric acid and 60% B: 10% water–90% methanol–0.2% phosphoric acid; flow rate 1.5 ml/min detecting at 220 nm; $t_R$=6.73 min (95.7%).

Anal. calc'd. for $C_{20}H_{28}N_2O_4S$·0.12 ethyl acetate: C, 58.05; H, 6.24; N, 6.95; S, 7.96 Found C, 58.23; H, 6.34; N, 6.83; S, 7.81.

EXAMPLE 2

[3R-[3α(S*), 6α,9aβ]]-Hexahydro-3-[(2-mercapto-1-oxo-3-phenylpropyl)amino]-4-oxo-2H,6H-pyrido[2,1-b][1,3]thiazine-6-carboxylic acid a) N-[(Phenylmethoxy)carbonyl]-L-cysteine A solution of N,N'-bis[(phenylmethoxy)carbonyl]-L-cystine (4.658 g., 9.16 mmol.) in methanol (35 ml.) was treated with 2N sulfuric acid (23 ml.) followed by portionwise treatment with zinc dust (2.442 g., 37.3 mmol.). The mixture was heated at 70° C. for 1.5 hours, filtered while still warm, and concentrated on the rotovap. The residual solution was extracted with ethyl ether and the ethereal extract was washed with water and brine, then dried (sodium sulfate), filtered and stripped. The residue (oil) was dissolved in carbon tetrachloride, cooled to 0° C., and seeded to slowly afford a precipitate. The solid was collected by filtration and washed with cold carbon tetrachloride to give 2.648 g. of product. The mother liquor was stripped, flash chromatographed (Merck silica gel, ethyl acetate followed by 4% acetic acid in ethyl acetate) to give additional product after crystallization (246 mg.). The total yield of product was 2.894 g. TLC (5% acetic acid in ethyl acetate) $R_f$=0.58.

b) S-Acetyl-N-r(Phenylmethoxy)carbonyl]-L-cysteine

A homogeneous solution of the product from part (a) (2.70 g., 10.6 mmol.) in water (30 ml., de-oxygenated via argon bubbling) containing potassium bicarbonate (2.140 g., 21.4 mmol.) was treated with acetic anhydride (8.0 ml., 8.66 g, 84.8 mmol.). After 10 minutes at room temperature, the mixture was acidified with 10% hydrochloric acid and extracted with ethyl ether. The ethyl ether extract was washed twice with water and brine, then dried (sodium sulfate), filtered and stripped to give an oil. The residue was azeotroped three times with toluene and twice with ethyl ether/hexane, after which time the oil crystallized. The residue was triturated with ethyl ether/hexane and the solid was collected by filtration to give 2.19 g., of pure title product. TLC (5% acetic acid in ethyl acetate) $R_f$=0.56.

c) (S)-2-[[N-[(Phenylmethoxy)carbonyl-S-acetyl-L-cysteinyl]amino]-6,6-dimethoxyhexanoic acid, methyl ester A slurry of (S)-2-phthalimido-6,6-dimethoxyhexanoic acid, methyl ester [prepared as described in Example 1(d), 1.158 g., 3.45 mmol.) in methanol (12 ml.) was treated with hydrazine monohydrate (176 μl., 182 mg., 3.63 mmol.). The mixture became homogeneous within 10 minutes. After stirring at room temperature for 67 hours, the resulting slurry was filtered, stripped, slurried in methylene chloride, filtered and stripped again to afford the crude intermediate amine as a colorless oil. Meanwhile a partial slurry of the product from part (b) (1.185 g., 3.98 mmol.) in methylene chloride (14 ml.) was treated with triethylamine (555 μl., 403 mg., 3.98 mmol.). The now homogeneous solution was cooled to 0° C., treated with the above amine as a solution in methylene chloride (7 mL), then treated with benzotriazol-1-yloxytris(dimethylamino)phosphonium hexafluorophosphate (1.762 g., 3.98 mmol.). The mixture was stirred at 0° C. for 2.5 hours, then at room temperature for 45 minutes. The solvent was removed and the residue was partitioned between ethyl acetate and water. The organic layer was washed with 50% saturated sodium bicarbonate and brine, then dried (sodium sulfate), filtered and stripped. The residue was flash chromatographed (Merck silica gel, 65:35-ethyl acetate:hexanes) to give 1.15 g., of the pure title product as a white foam. TLC (75:25-ethyl acetate:hexanes) $R_f$=0.42.

Analysis Calc'd. for $C_{22}H_{32}N_2O_8S$: C, 54.53; H, 6.66; N, 5.78; S, 6.62; Found C, 54.79; H, 6.72; N, 5.77; S, 6.95.

d) [3R-(3α,6α,9aβ)]-Hexahydro-3-[[(phenylmethoxy)carbonyl]amino]-4-oxo-2H,6H-pyrido[2,1-b][1,3]thiazine-6-carboxylic acid, methyl ester A de-oxygenated (argon bubbling) solution of the product from part (c) (1.040 g., 2.15 mmol.) in methanol (12 ml.) at 0° C. was treated with sodium methoxide (25% by weight in methanol, 490 μl., 463 mg., 2.14 mmol.). After 20 minutes, the mixture was quenched with saturated ammonium chloride, diluted with water, and extracted with ethyl acetate. The ethyl acetate extract was washed with water and brine, then dried (sodium sulfate), filtered and stripped. The residue was redissolved in methylene chloride (200 ml.) and stirred at room temperature with Amberlyst® 15 ion exchange resin (820 mg., pre-washed successively with 6N hydrochloric acid, water, tetrahydrofuran, then methylene chloride). After 3 hours, the solution was filtered, stripped and flash chromatographed (Merck silica gel, 65:35-ethyl acetate:hexanes) to give 757 mg. of the title product as a colorless oil. TLC (75:25-ethyl acetate:hexanes) $R_f$=0.58.

e) [3R-(3α,6α,9aβ)]-Hexahydro-3-amino-4-oxo-2H, 6H-pyrido[2,1-b][1,3]thiazine-6-carboxylic acid, methyl ester A solution of the product from part (d) (752 mg., 1.99 mmol.) in dry methylene chloride (15 ml.) was treated at

27 room temperature with iodotrimethylsilane (620 μL, 872 mg., 4.36 mmol.). After stirring for 3 hours, the mixture was quenched with water, treated with a small amount 10% hydrochloric acid, and extracted with ethyl ether. The layers were separated and the ethereal layer was back-extracted with water. The pooled aqueous layers were made basic (pH 13) with 10% sodium hydroxide and extracted twice with methylene chloride. The pooled methylene chloride extracts were dried (sodium sulfate), filtered and stripped to give 290 mg. of crude title product as a colorless oil. TLC (10% methanol in methylene chloride) $R_f$=0.38.

f) [3R-[3α(S*),6α,9aβ]]-Hexahydro-3-[[2-(acetylthio)-1-oxo-3-phenylpropyl]amino]-4-oxo-2H,6H-pyrido[2,1-b][1,3]thiazine-6-carboxylic acid, methyl ester A cold (0° C.) solution of (S)-2-(acetylthio)benzenepropanoic acid (294 mg., 1.31 mmol.) and triethylamine (180 μL, 131 mg., 1.29 mmol.) in methylene chloride (8 ml.) was treated with the product from part (e) (287 mg., 1.17 mmol.) as a solution in 6 ml. methylene chloride. Benzotriazol-1-yloxytris(dimethylamino)phosphonium hexafluorophosphate (575 mg., 1.30 mmol.) was then added. The clear, nearly colorless solution was stirred at 0° C. for 1 hour and then at room temperature for 1 hour. The solvent was removed by rotary evaporation and the residue was partitioned between ethyl acetate and 5% potassium bisulfate. The organic layer was washed successively with water, 50% saturated sodium bicarbonate and brine, then dried (sodium sulfate), filtered and stripped. The residue was flash chromatographed (Merck silica gel, 1:1-ethyl acetate:hexanes) to give 412 mg. of the pure title product as a white foam. TLC (1:1-ethyl acetate:hexanes) $R_f$=0.27; $[\alpha]_D$=−107.0° C. (c=0.6, chloroform).

g) [3R-[3α(S*),6α,9aβ]]-Hexahydro-3-[(2-mercapto-1-oxo-3-phenylpropyl)amino]-4-oxo-2H,6H-pyrido[2,1-b][1,3]thiazine-6-carboxylic acid A 0° C. solution of the product from part (f) (406 mg, 0.90 mmol) in methanol (5 ml., de-oxygenated via argon bubbling) was treated with 1N sodium hydroxide (5 ml., deoxygenated via argon bubbling). After stirring for one hour, the solution was warmed to room temperature and stirring under argon was continued for an additional 1.25 hours. The mixture was acidified with 5% potassium bisulfate, diluted with water and extracted with ethyl acetate. The ethyl acetate extract was washed with water and brine, then dried (sodium sulfate), filtered and stripped. The residue was flash chromatographed twice (Merck silica gel, 2% acetic acid in ethyl acetate). Product fractions were checked by HPLC. The desired fractions were pooled, stripped, and azeotroped twice with ethyl acetate. The residue was taken up in a small amount of ethyl acetate and triturated with hexanes. The solvent was stripped and the residue was slurried in hexanes, stripped and dried in vacuo to give 98.3 mg. of the title product as a hard white foam. TLC (2% acetic acid in ethyl acetate) $R_f$=0.46; $[\alpha]_D$=−57.0° (c=0.4, chloroform).

HPLC: YMC S3 ODS column (6.0×150 mm); eluted with 40% A: 90% water–10% methanol–0.2% phosphoric acid and 60% B: 10% water–90% methanol–0.2% phosphoric acid; flow rate 1.5 mL/min detecting at 220 nm; $t_R$=8.33 min. (95.0%).

Anal. calc'd. for $C_{18}H_{22}N_2O_4S_2 \cdot 0.2$ ethyl acetate: C, 54.79; H, 5.77; N, 6.80; S, 15.56. Found C, 54.59; H, 6.04; N, 6.59; S, 15.16.

28

EXAMPLE 3

[4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid a) [S-(R*,R*)]-2-[[2-Phthalimido-4-(acetylthio)-1-oxobutyl]amino]-6,6-dimethoxyhexanoic acid, methyl ester A cold (0° C.) solution of triphenylphosphine (1.143 g., 4.36 mmol.) in tetrahydrofuran (20 ml.) was treated with diisopropyl azidodicarboxylate (860 μL, 883 mg., 4.37 mmol.). Within 5 minutes a white slurry developed. After 30 minutes, a solution of [S-(R*,R*)]-2-[(2-phthalimido-4-hydroxy-1-oxobutyl)-amino]-6,6-dimethoxyhexanoic acid, methyl ester [prepared as described in Example 1(f), 928 mg., 2.19 mmol.] in tetrahydrofuran (8 ml.) was added followed by neat thioacetic acid (312 μL, 332 mg., 4.36 mmol.). The mixture was stirred at 0° C. for 1.25 hours, then partitioned between 50% saturated sodium bicarbonate and ethyl acetate. The ethyl acetate extract was washed with brine, dried (sodium sulfate), filtered and stripped. The residue was redissolved in ethyl acetate and treated with a small amount of hexane to precipitate triphenylphosphine oxide. The mixture was filtered and the filtrate was flash chromatographed (Merck silica gel, 65:35-ethyl acetate:hexanes) to give 894 mg. of the title product as a colorless oil. TLC (75:25-ethyl acetate:hexanes) $R_f$=0.43.

b) [4S-(4α,7α,10aβ)]-Octahydro-4-phthalimido-5-oxo-7H-pyrido[2,1-b][1,3]thiazepine-7-carboxylic acid, methyl ester A de-oxygenated (argon bubbling) solution of the product from part (a) (814 mg., 1.65 mmol.) in methanol (15 ml.) at 0° C. was treated with sodium methoxide (25% by weight in methanol, 1.05 ml., 4.6 mmol.). After 5 minutes, the mixture was quenched with saturated ammonium chloride, diluted with water, and extracted with ethyl acetate. The ethyl acetate extract was washed with water and brine, then dried (sodium sulfate), filtered and stripped. The residue was redissolved in methylene chloride (180 ml.) and stirred at room temperature with Amberlyst® 15 ion exchange resin (285 mg., pre-washed successively with 6N hydrochloric acid, water, tetrahydrofuran, then methylene chloride). After 46 hours, the solution was filtered, stripped and flash chromatographed (Merck silica gel, 1:1-ethyl acetate:hexanes) to give 314 mg. of the title product as a white foam. Trituration of the foam with ethyl ether produced the title product as a white solid; m.p.=147°–148° C. TLC (75:25- ethyl acetate:hexanes) $R_f$=0.56; $[\alpha]_D$=−143.2° (c=0.6, chloroform).

c) [4S-[4α(R*),7α,10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl ester The product from part (b) (280 mg., 0.72 mmol.) in methanol (8 ml.) was treated with hydrazine monohydrate (42 μL, 43.3 mg., 0.86 mmol.) and the solution was stirred at room temperature for 67 hours. The mixture was filtered and the solid was washed with methanol. The filtrate was stripped, triturated with methylene chloride, filtered again and stripped to give the crude amine as a yellow oil (about 205 mg.).

A cold (0° C.) solution of (S)-2-(acetylthio)benzenepropanoic acid (178 mg., 0.79 mmol.) and triethylamine (111 μL., 80 mg., 0.80 mmol.) in methylene chloride (3 ml.) was treated with the above amine (as a solution in 7 ml. methylene chloride) followed by benzotriazol-1-yloxytris(dimethylamino)phosphonium hexafluorophosphate (353 mg., 0.80 mmol.). The solution was stirred at 0° C. for 1 hour and then at room temperature for 2 hours. The solvent was stripped and the residue was partitioned between ethyl acetate and 5% potassium bisulfate. The organic layer was washed successively with water, 50% saturated sodium bicarbonate and brine, then dried (sodium sulfate), filtered and stripped. The residue was flash chromatographed (Merck silica gel, 1:1-ethyl acetate:hexanes) to give 272 mg. of the pure title product as a white foam.

d) [4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid A room temperature solution of the product from part (c) (227 mg., 0.49 mmol.) in methanol (5 ml., de-oxygenated via argon bubbling) was treated with 1N sodium hydroxide (8 ml. deoxygenated via argon bubbling). After stirring for 1 hour, the mixture was acidified with 10% hydrochloric acid, diluted with water and extracted with ethyl acetate. The ethyl acetate extract was washed with water and brine, then dried (sodium sulfate), filtered and concentrated. The resulting solid was slurried in ethyl acetate and collected by filtration. The filtrate was flash chromatographed (Merck silica gel, 1% acetic acid in ethyl acetate) and the desired fractions were pooled, stripped, and triturated with ethyl acetate/ethyl ether to give additional solid. The solids were pooled to give a total of 150 mg. of the title product; m.p. 216°–217° C. (decomp.). TLC (2% acetic acid in ethyl acetate) $R_f$=0.56; $[\alpha]_D$=−72.6° (c=0.28, dimethylformamide).

HPLC YMC S3 ODS column (6.0×150 mm); eluted with 40% A: 90% water–10% methanol–0.2% phosphoric acid and 60% B: 10% water–90% methanol–0.2% phosphoric acid; flow rate 1.5 ml/min detecting at 220 nm; $t_R$=9.48 min. (97.4%).

Anal. calc'd. for $C_{19}H_{24}N_2O_4S_2$·0.14 ethyl acetate: C, 55.82; H, 6.02; N, 6.66; S, 15.24; Found C, 55.53; H, 6.01; N, 6.63; S, 14.91.

EXAMPLE 4

[4S-[4α(R*),7α,9αβ]]-Octahydro-4-[(2-mercapto-1-oxo-3-phenylpropyl)amino]-5-oxopyrrolo[2,1-b][1,3]oxazepine-7-carboxylic acid a) (S)-2-Phthalimido-5-oxo-5-(phenylmethoxy) pentanoic acid To a solution of 7-benzyl-L-glutamate (17.49 g., 73.70 mmol.) in aqueous (180 ml.) sodium carbonate (7.81 g., 73.70 mmol.) and dioxane (120 ml.) was added N-carbethoxyphthalimide (16.50 g., 75.27 mmol., 1.02 eq.). After stirring at room temperature for 4.5 hours, The reaction mixture was acidified with 6N hydrochloric acid (30 ml.) and extracted into ethyl acetate (2×400 ml.). The combined ethyl acetate extracts were washed with 50% brine (200 ml.), and brine (200 ml.), dried over sodium sulfate, filtered, concentrated and dried in vacuo to yield a crude oil (41.4 g.). To a solution of the crude residue in ethyl ether (100 ml.) was added dicyclohexylamine (14 ml.). After standing in the refrigerator overnight, the ethyl ether was removed by rotary evaporation and the oily residue was crystallized from ethyl acetate/hexane. The resulting precipitate was collected by filtration, washed with hexane and dried in vacuo to yield 21.21 g. of the title product as the dicyclohexyl amine salt. A suspension of this dicyclohexylamine salt in ethyl acetate (200 ml.) was washed with 5% potassium bisulfate (3×50 ml.), brine (50 ml.) and dried over magnesium sulfate, filtered and concentrated to yield 13.5 g. of the title product as a white foam. TLC: (3% acetic acid in 9:1 ethyl acetate:heptane) $R_f$=0.30.

b) (S)-2-Phthalimido-5-oxo-5-(phenylmethoxy) pentanoic acid, methyl ester

To a solution of the product from part (a) (13.22 g., 36.0 mmol.) and cesium carbonate (5.86 g., 18.0 mmol.) in dimethylformamide (100 ml.) was added iodomethane (8.1 ml., 129.6 mmol., 3.6 eq.). The yellow solution was stirred for 2.5 hours, and was then partitioned between ethyl acetate (300 ml.) and water (250 ml.). The ethyl acetate extract washed with 5% sodium bicarbonate (200 ml.) and brine, dried over magnesium sulfate, filtered and concentrated to yield 13.68 g. a yellow oil. The residue was purified by chromatography on a 5×20 cm. silica gel column eluting with 30% ethyl acetate/hexane. The desired fractions were combined and concentrated to yield 10.0 g of the title product. TLC (1:1, ethyl acetate:hexane) $R_f$=0.45.

c) (S)-2-Phthalimido-4-(carboxy)butanoic acid, methyl ester

To a solution of the product from part (b) (10.0 g., 26.22 mmol.) in ethyl acetate (115 ml.) was added 20% palladium hydroxide on carbon catalyst (1.90 g.) and the resulting suspension was stirred under hydrogen atmosphere (balloon) for 2.5 hours. The mixture was filtered, washed thoroughly with ethyl acetate, concentrated and dried in vacuo to yield 7.29 g. of crude title product as a white solid; m.p. 137°–138° C. TLC (10% methanol/methylene chloride) $R_f$=0.43.

d) (S]-2-Phthalimido-5-oxo-5-(ethylthio)pentanoic acid, methyl ester

To a solution of the product from part (c) (7.27 g., 24.95 mmol.) in methylene chloride (125 ml.) at 0° C. under argon was added ethanethiol (4.81 ml., 64.92 mmol., 2.6 eq), 4-dimethylaminopyridine (609 mg., 4.99 mmol., 0.2 eq.) and ethyl-3-(3-dimethylamino)propyl carbodiimide, hydrochloride salt (5.27 g., 27.47 mmol., 1.1 eq.). After stirring at 0° C. for 2 hours and at room temperature for 1 hour the reaction was concentrated, diluted with ethyl acetate (400 ml.) and washed with 5% potassium bisulfate (200 ml.), saturated sodium bicarbonate (200 ml.), and brine (200 ml.), dried over sodium sulfate, filtered, concentrated and dried in vacuo to yield 8.30 g. of title product as a crude oil. TLC (1:1, ethyl acetate:hexane) $R_f$=0.47.

e) (S)-2-Phthalimido-5-oxopentanoic acid, methyl ester

A suspension of the product from part (d) (8.30 g., 24.75 mmol.) and 10% palladium on carbon (1.24 g.) in acetonitrile (150 ml.) under argon was treated dropwise with triethylsilane (7.91 ml., 49.5 mmol., 2 eq.). After stirring at room temperature for 45 minutes, the mixture was filtered, concentrated and dried in vacuo. The crude residue was purified by chromatography on a 5×25 cm silica gel column eluting with 25% ethyl acetate/hexane (41.) followed by 35% ethyl acetate/hexane (21.). The desired fractions were combined to yield 5.60 g. of title product. TLC (1:1, ethyl acetate:hexane) $R_f$=0.32.

f) (S)-2-phthalimido-5,5-dimethoxyoentanoic acid, methyl ester

A solution of the product from part (e) (5.60 g., 20.34 mmol.) in methanol (60 ml.) and methylene chloride (40 ml.) was treated with trimethylorthoformate (3.8 ml., 34.59 mmol., 1.7 eq.) and p-toluenesulfonic acid monohydrate (280 mg.). After stirring at room temperature for 1.5 hours the reaction was quenched with 2 ml. of saturated sodium bicarbonate, concentrated, and partitioned between ethyl acetate (400 ml.) and water (100 ml.). The ethyl acetate extract was washed with saturated sodium bicarbonate (100 ml.), brine (100 ml.), dried over magnesium sulfate, filtered and concentrated to a crude oil. The crude residue was purified by chromatography on a 5×20 cm silica gel column eluting with 30% ethyl aceatate/hexane (2l.). The desired fractions were combined, concentrated and dried in vacuo to yield 6.20 g. of title product. TLC (1:1, ethyl acetate:hexane) $R_f=0.40$.

g) (S)-2-Amino-5,5-dimethoxypentanoic acid, methyl

A solution of the product from part (f) (6.16 g., 19.18 mmol.) in methanol (125 ml.) was treated with hydrazine monohydrate (0.98 ml., 20.14 mmol., 1.05 eq). After stirring at room temperature for 6 days, the resulting slurry was filtered, concentrated, triturated in methylene chloride, filtered, concentrated and dried in vacuo to afford 3.57 g. of title product as a cloudy oil. TLC (10% methanol in methylene chloride) $R_f=0.41$.

h) [S-(R*,R*)]-2-[[2-Phthalimido-4-(triphenylmethoxy)-1-oxobutyl]amino]-5,5-dimethoxypentanoic acid, methyl ester A solution of (S)-2-phthalimido-4-(triphenylmethoxy) butanoic acid, triethylamine salt [prepared as described in Example 1(b), 11.62 g., 19.60 mmol., 1.05 eq.] in methylene chloride (100 ml.) at 0° C. was treated with benzotriazol-1-yloxytris(dimethylamino)phosphonium hexafluorophosphate reagent (8.67 g., 19.60 mmol., 1.05 eq.). The mixture was stirred for 45 minutes at 0° C., then treated with a solution of the product from part (g) (3.57 g., 18.67 mmol.) in methylene chloride (50 ml.). After 10 minutes at 0° C. and 2 hours at room temperature, the solution was partitioned between ethyl acetate (300 ml.) and water (100 ml.). The ethyl acetate layer was washed with 50% saturated sodium bicarbonate (100 ml.) and brine (100 ml.), dried over magnesium sulfate, filtered and concentrated. The residue was purified by chromatography on a 5×25 cm silica gel column eluting with 1:1 ethyl acetate/hexane affording 8.58 g. of title product. TLC (1:1, ethyl acetate:hexane) $R_f=0.20$.

i) [S-(R*,R*)]-2-[[2-Phthalimido-4-hydroxy-1-oxobutyl)amino]-5,5-dimethoxypentanoic acid, ester A solution of the product from part (h) (8.58 g., 12.91 mmol.) in methanol (100 ml.) was treated with p-toluensulfonic acid monohydrate (850 mg.). After stirring at room temperature for 3.5 hours, the mixture was partitioned between ethyl acetate (200 ml.) and 10% saturated sodium bicarbonate (100 ml.). The phases were separated and the aqueous layer was extracted again with ethyl acetate (100 ml.). The combined ethyl acetate extracts were washed with brine, dried over magnesium sulfate, filtered and concentrated. The residue was purified by chromatography on a 5×20 cm silica gel column eluting with 8:2 ethyl acetate:hexane (1l.) followed by 1% methanol in ethyl acetate (2l.). The desired fractions were combined, concentrated and dried in vacuo to yield 4.33 g. of title product. TLC (8:2 ethyl acetate:hexane) $R_f=0.21$.

j) [4S-[4α,7α,9aβ]]-Octahydro-4-phthalimido-5-oxopyrrolo[2,1-b][1,3]oxazepine-7-carboxylic acid, methyl ester A solution of the product from part (i) (1.89 g., 4.48 mmol.) in methylene chloride (90 ml.) was treated with Amberlyst® 15 ion exchange resin (400 mg., pre-washed successively with 6N hydrochloric acid, water, tetrahydrofuran and methylene chloride). After stirring at room temperature for 3 hours the solution was filtered, concentrated and flash chromatographed on a 5×15 cm silica gel column eluting with 6:4 ethyl acetate:hexane to afford 1.51 g. of title product as a white foam. TLC (8:2 ethyl acetate:hexane) $R_f=0.32$.

k) [4S-(4α,7α,9aβ)]-4-Amino-octahydro-5-oxopyrrolo[2,1-b][1,3]oxazepine-7-carboxylic methyl ester The product from part (j) (764 mg., 2.13 mmol.) in methanol (15 ml.) was treated with hydrazine monohydrate (109 μL., 2.24 mmol., 1.05 eq.) and the solution was stirred at room temperature for 4 days. The mixture was filtered and the solid was washed with methanol. The filtrate was concentrated, triturated with methylene chloride, filtered again and concentrated. The residue was purified by chromatography on a 2×15 cm silica gel column eluting with 3% methanol in methylene chloride (3l.) followed by 10% methanol in methylene chloride (1l.). The desired fractions were combined and concentrated to afford 451 mg. of title product as an oil. TLC (10 % methanol in methylene chloride) $R_f=0.18$.

l) [4S-[4α(R*),7α,9aβ]]-Octahydro-4-[[2-(acetylthio)-1-oxo-3-phenylpropyl]amino]-5-oxopyrrolo[2,1-b][1,3]oxazepine-7-carboxylic acid, methyl ester A suspension of the dicyclohexylamine salt of (S)-2-acetylthio-3-benzenepropanoic acid [prepared as described in Example 1(h), 870 mg., 2.14 mmol., 1.14 eq.] in ethyl acetate (70 ml.) was washed with 5% potassium bisulfate (5×20 ml.), 50% brine (20 ml.), and brine (20 ml.), dried (anhydrous sodium sulfate), filtered, concentrated and dried in vacuo overnight to give (S)-2-(acetylthio) benzenepropanoic acid, This free acid was dissolved in dry methylene chloride (10 ml.), cooled to 0° C. (ice-salt bath) and treated with triethylamine (298 μl, 2.14 mmol.) followed by a solution of the product from part (k) (430 mg., 1.88 mmol.) in methylene chloride (10 ml.) and benzotriazol-1-yloxytris (dimethylamino) phosphonium hexafluorophosphate (947 mg., 2.14 mmol., 1.14 eq.). The resultant solution was stirred at 0° C. for 50 minutes then at room temperature for 3 hours. The reaction mixture was concentrated, diluted with ethyl acetate (150 ml.), washed with 0.5N hydrochloric acid (50 ml.), water (50 ml.), saturated sodium bicarbonate (50 ml.), water (50 ml.) and brine (50 ml.), dried (anhydrous magnesium sulfate), filtered, and evaporated to dryness. The crude product was adsorbed onto Celite® and chromatographed on a silica gel column (5×10 cm), eluting with 60% ethyl acetate/hexane (3l.). The desired fractions were combined and concentrated, affording 779 mg. of pure title product. TLC (6:4, ethyl acetate:hexane) $R_f=0.17$.

m) [4S-[4α(R*),7α,9a,β]]-Octahydro-4-[(2-mercapto-1-oxo-3-phenylpropyl)amino]-5-oxopyrrolo[2,1-b][1,3]oxazepine-7-carboxylic acid A solution of the product from part (1) (754 mg., 1.74 mmol.) in methanol (15 ml.) was purged with argon for 30 minutes, cooled to 0° C. (ice-salt bath) then treated dropwise with a previously purged (argon, 30 minutes) solution of 1.0N sodium hydroxide (12 ml.) maintaining the bubbling of argon throughout the addition and length of the reaction. The reaction mixture was stirred at 0° C. for 3 hours, acidified at 0° C. with 5% potassium bisulfate to pH 1 then extracted with ethyl acetate (3×100 ml.). The combined organic extracts were washed with 50% brine (100 ml.), brine (100 ml.), dried (anhydrous sodium sulfate), filtered, evaporated to dryness and dried in vacuo to yield a white foam. The residue was purified by chromatography on a 2.5×15 cm silica gel column eluting with ethyl acetate (500 ml.) and 0.3% acetic acid in ethyl acetate (1 l.). The desired fractions were concentrated, stripped with chloroform and dried in vacuo overnight at 50° C. over phosphorus pentoxide to yield the title product as a white foam; m.p. 88°–92° C.; $[\alpha]_D = -63.8°$ (c=1.0, methanol). TLC (1% acetic acid in ethyl acetate) $R_f = 0.24$.

$^1$H-NMR: 400 MHz; CDCl$_3$: δ 1.80–2.31 (m's, 7H), 3.10 (m, 1H), 3.27 (m, 1H), 3.63 (m, 1H), 4.0 (m, 1H), 4.20 (m, 1H), 4.49 (m, 1H), 4.75 (m, 1H), 5.23 (m, 1H), 7.19–7.30 (m's, 5H), 7.52 (d, 1H, J=6 Hz).

$^{13}$C-NMR: 100 MHz; CDCl$_3$: δ 26.4, 32.0, 32.6, 41.2, 44.2, 53.0, 59.4, 70.6, 89.47, 126.9, 128.4, 129.3, 137.4, 171.2, 171.6, 174.8.

Anal. calc'd. for C$_{18}$H$_{22}$N$_2$O$_5$S•0.85 H$_2$O: C, 54.91; H, 6.07; N, 7.12; S, 8.14 Found: C, 54.85; H, 5.68; N, 7.18, S, 8.14.

HPLC: t$_R$=13.5 min (96.7%, UV 220); YMC S-3 ODS (C-18) 6.0×150 mm; 30% B:A-100% B:A, 25 minute linear gradient (A=90% water/methanol+0.2% phosphoric acid B=90% methanol/water+0.2% phosphoric acid) flow rate at 1.5 ml./min.

EXAMPLE 5

[4S-[4α(R*),7α,9aβ]]-Octahydro-4-[(2-mercapto-1-oxo-3-phenylpropyl)amino]-5-oxopyrrolo[2,1-b][1,3]thiazepine-7-carboxylic acid a) [S-(R*,R*)]-2-[[2-Phthalimido-4-(acetylthio)-1-oxobutyl]amino]-5,5-dimethoxypentanoic acid, methyl ester A 0° C. solution of triphenylphosphine (1.26 g., 4.79 mmol., 1.5 eq.) in dry tetrahydrofuran (15 ml.) was treated with diisopropyl azodicarboxylate (943 µl., 4.79 mmol.). The resultant white slurry was stirred for 30 minutes and then treated with a solution of [S-(R*,R*)]-2-[(2-phthalimido-4-hydroxy-1-oxobutyl)amino]-5,5-dimethoxypentanoic acid, methyl ester [prepared as described in Example 4(i), 1.35 g., 3.20 mmol.]in dry tetrahydrofuran (15 ml.) followed by neat thiolacetic acid (343 µl., 4.79 mmol.). The mixture was stirred at 0° C. for 1.5 hours and then partitioned between ethyl acetate (150 ml.) and 50% sodium bicarbonate (100 ml.). The ethyl acetate layer was washed with brine, dried over magnesium sulfate, filtered, concentrated, adsorbed onto Celite® and dried in vacuo. The crude material was purified by chromatography on a 2.5×15 cm silica gel column eluting with 1:1 ethyl acetate:hexane (1 l.) and 6:4 ethyl acetate:hexane (1 l.). The desired fractions were combined, concentrated and dried in vacuo affording 1.35 g. of title produce as an oil. TLC (8:2, ethyl acetate:hexane) $R_f$=0.42.

b) [S-(R*,R*)]-2-[(3-Phthalimido-4-mercapto-1-oxobutyl)amino]-5,5-dimethoxypentanoic acid, methyl ester A de-oxygenated (argon bubbling) solution of the product from part (a) (1.33 g., 2.76 mmol.) in methanol (25 ml.) at 0° C. was treated with sodium methoxide (25% by weight in methanol, 1.52 ml., 6.63 mmol., 2.4 eq.). After 3 minutes, the mixture was quenched with saturated ammonium chloride (3 ml.), diluted with water, and extracted with ethyl acetate (100 ml.). The ethyl acetate extract was washed with water (50 ml.) and brine (50 ml.), dried over sodium sulfate, filtered and concentrated. The residue was purified by chromatography on a 5×15 cm silica gel column eluting with 1:1 (3 l.) followed by 8:2 (2 l.) ethyl acetate:hexane. The desired product containing fractions were combined and concentrated to yield 853 mg. of title compound as an oil. TLC (8:2, ethyl acetate:hexane) $R_f$=0.43.

c) [4S-(4α,7α,9aβ)]-Octahydro-4-phthalimido-5-oxopyrrolo[2,1-b][1,3]thiazepine-7-carboxylic acid, methyl ester A solution of product from part (b) (847 mg., 1.93 mmol.) in methylene chloride (20 ml.) was treated with Amberlyst® 15 ion exchange resin (700 mg., pre-washed successively with 6N hydrochloric acid, water, tetrahydrofuran and methylene chloride). After stirring at room temperature for 17 hours the solution was filtered, concentrated and flash chromatographed on a 2.5×15 cm silica gel column eluting with 1:1 ethyl acetate:hexane to afford 691 mg. of title product as a white foam. TLC (8:2 ethyl acetate:hexane) $R_f$=0.48.

d) [4S-(4α,7α,9aβ)]-4-Amino-octahydro-5-oxopyrrolo[2,1-b][1,3]thiazepine-7-carboxylic acid, methyl ester The product from part (c) (899 mg., 2.40 mmol.) in methanol (17 ml.) was treated with hydrazine monohydrate (122 µl., 2.52 mmol., 1.05 eq.) and the solution was stirred at room temperature for days. The mixture was filtered and the solid was washed with methanol. The filtrate was concentrated, triturated with methylene chloride, filtered again, concentrated, and dried in vacuo to yield 572 mg. of title product as a cloudy oil. TLC (10% methanol in methylene chloride) $R_f$=0.13.

e) [4S-[4α(R*),7α,9aβ]]-Octahydro-4-[[2-(acetylthio)-1-oxo-3-phenylpropyl]amino]-5-oxopyrrolo[2,1-b][1,3]thiazepine-7-carboxylic acid, methyl ester A suspension of the dicyclohexylamine salt of (S)-2-(acetylthio)benzenepropanoic acid [prepared as described in Example 1 (h), 1.045 g., 2.58 mmol., 1.1 eq] in ethyl acetate (100 ml.) was washed with 5% potassium bisulfate (5×25 ml.), 50% brine (25 ml.), and brine (25 ml.), dried (anhydrous sodium sulfate), filtered, concentrated and dried in vacuo for one hour to give (S)-2-(acetylthio)-benzenepropanoic acid.

This free acid was dissolved in dry methylene chloride (10 ml.), cooled to 0° C. (ice-salt bath) and treated with triethylamine (360 µl., 2.58 mmol.), benzotriazol-1-yloxytris(dimethylamino)phosphonium hexafluorophosphate (1.141 g., 2.58 mmol.) and then a solution of the product from part (d) (572 mg., 2.34 mmol.) in methylene chloride (10 ml.). The resultant solution was stirred at 0° C. for 30 minutes then at room temperature for 2.5 hours. The reaction mixture was concentrated, diluted with ethyl acetate (100 ml.) washed with 0.5N hydrochloric acid (50 ml.), water (50 ml.), saturated sodium bicarbonate (50 ml.), water (50 ml.) and brine (50 ml.), dried (anhydrous magnesium sulfate), filtered, and evaporated to dryness. The crude product was adsorbed onto Celite® and chromatographed on a silica gel column (5×10 cm), eluting with 25%(5 l.), 30%

(2l.), 35% (2l.), and 40% (2l.) ethyl acetate/hexane. The mixed fractions were combined and rechromatographed eluting with the same gradient. The desired fractions were combined and concentrated, affording 490 mg. of pure title product. TLC (1:1, ethyl acetate:hexane) $R_f$=0.16.

f) [4S-[4α(R*),7α,9aβ]]-Octahydro-4-[(2-mercapto-1-oxo-3-phenylpropyl)amino]-5-oxopyrrolo[2,1-b][1,3]thiazepine-7-carboxylic acid A solution of the product from part (e) (490 mg., 1.09 mmol.) in methanol:tetrahydrofuran (8 ml.: 4 ml.) was purged with argon for 30 minutes, cooled to 0° C. (ice-salt bath) then treated dropwise with a previously purged (argon, 30 minutes) solution of 1.0N sodium hydroxide (10 ml.) maintaining the bubbling of argon throughout the addition and length of the reaction. The reaction mixture was stirred at 0° C. for 3 hours, acidified at 0° C. with 5% potassium bisulfate to pH 2 then extracted with ethyl acetate (3×75 ml.). The combined organic extracts were washed with brine (75 ml.), dried (anhydrous sodium sulfate), filtered, evaporated to dryness and dried in vacuo to yield a white foam (489 mg.). The residue was purified by chromatography on a 2.5×15 cm silica gel column eluting with 9:1 ethyl acetate:heptane (400 ml.) and 0.5% acetic acid in 9:1 ethyl acetate:heptane (1l.). The desired fractions were concentrated, stripped with methylene chloride/heptane and dried in vacuo to yield 428 mg. of product. The pure material was recrystallized from a mixture of ethyl acetate/methanol/hexane. The crystals were collected by filtration, washing thoroughly with ethyl ether, and dried in vacuo overnight at 40° C. over phosphorus pentoxide to yield 305 mg. of title product as white crystals; m.p. 206°–208° C.; $[\alpha]_D$=−96.3° (c=1.0, methanol). TLC (5% acetic acid in 9:1 ethyl acetate:heptane) $R_f$=0.29.

$^1$H-NMR: 400 MHz; CDCl$_3$ w/2 drops CD$_3$OD: δ 1.94(m, 1H), 2.02(d, 1H, J=9 Hz), 2.08(m, 1H), 2.20–2.55 (m's, 4H), 2.95(m, 1H), 3.08(m, 1H), 3.23 (m, 1H), 3.27 (m, 1H), 3.59 (m, 1H), 4.54 (t, 1H, J=7.3 Hz), 4.60 (m, 1H), 5.23 (m, 1H), 7.18–7.34 (m's, 5H), 7.63 (d, 1H, J=6 Hz).

$^{13}$C-NMR: 100 MHz; CDCl$_3$ w/2 drops CD$_3$OD: δ 27.6, 31.1, 32.1, 32.9, 41.1, 44.0, 52.8, 60.4, 62.2, 126.77, 128.3, 129.0, 137.4, 170.2, 171.4, 172.6.

Anal. calc'd. for $C_{18}H_{22}N_2O_4S_2\cdot0.08$ H$_2$O: C, 54.60; H, 5.64; N, 7.07; S, 16.19 Found: C, 54.65; H, 5.54; N, 7.02, S, 15.80.

HPLC: $t_R$=13.0 min (98.8%, UV 220); YMC S-3 ODS (C-18) 6.0×150 mm; 40% B:A-100% B:A, 25 minute linear gradient (A=90% water/methanol+0.2% phosphoric acid; B=90% methanol/water+0.2% phosphoric acid); flow rate at 1.5 ml/min.

EXAMPLE 6

[4S-[4α(R*),7α,9aβ)]]-Octahydro-4-[(2-mercapto-1-oxo-3-phenylpropyl)amino]-5-oxopyrrolo[2,1-b][1,3]thiazepine-7-carboxylic acid The product of Example 5 was also prepared as follows:

a) N-[(phenylmethoxy)carbonyl]-L-homoserine

N-(Benzyloxycarbonyloxy)succinimide (23.57 g., 94.58 mmol.) was added to a solution of L-homoserine (10.24 g., 85.98 mmol.) and sodium bicarbonate (7.95 g., 94.58 mmol., 1.1 eq.) in a mixture of water (100 ml.) and acetone (100 ml.). The mixture was stirred at room temperature overnight. The acetone was removed under reduced pressure (rotovap) and the aqueous solution was washed with methylene chloride (2×75 ml.). The aqueous layer was then acidified to pH 2 by addition of 6N hydrochloric acid and extracted with ethyl acetate (2×250 ml.). The combined ethyl acetate layers were washed with water (2×100 ml.) and brine, dried over sodium sulfate, filtered, concentrated and dried in vacuo to afford 19.54 g. of title product as a white solid. TLC (ethyl acetate:n-butanol:acetic acid:water; 2:1:1:1) $R_f$=0.74 b) N-[(phenylmethoxy)carbonyl]-O-(triohenylmethyl)-L-homoserine

To a suspension of the product from part (a) (19.51 g., 77.04 mmol.) in chloroform (250 ml.) was added triethylamine (12.35 ml., 88.59 mmol., 1.15 eq.). The homogeneous mixture was treated with triphenylmethyl chloride (24.70 g., 88.59 mmol.) and the reaction was stirred for 3 hours. The reaction mixture was concentrated under reduced pressure (rotovap), partitioned between ethyl acetate (400 ml.) and 5% potassium bisulfate (200 ml.). The ethyl acetate layer was washed with 5% potassium bisulfate (200 ml.), water (2×200 ml.), and brine (200 ml.), dried over sodium sulfate, filtered, and concentrated to yield 45.4 g. material. The residue was chromatographed on a 10×30 cm silica gel column eluting with 6:4 ethyl acetate:hexane (2l.) followed by 1% acetic acid in 8:2 ethyl acetate:hexane to give 8.76 g. of pure title compound.

c) (S)-2-Amino-5,5-dimethoxypentanoic acid, methyl ester (S)-2-Phthalimido-5,5-dimethoxypentanoic acid, methyl ester [prepared as described in Example 4 (f), 3.35 g., 10.43 mmol.) in methanol (70 ml.) was treated with hydrazine monohydrate (531 μl., 10.95 mmol., 1.05 eq.) and the solution was stirred at room temperature for 6 days. The mixture was filtered and the solid was washed with methanol. The filtrate was concentrated, triturated with methylene chloride, filtered again, concentrated, and dried in vacuo to yield 1.89 g. of title product as a cloudy oil. TLC (10% methanol in methylene chloride) $R_f$=0.39.

d) [S-(R*,R*)]-2-[[2-[[(Phenylmethoxy)carbonyl]amino]-4-(triphenylmethoxy)-1-oxobutyl]-amino]-5,5-dimethoxypentanoic acid, methyl ester A solution of the product from part (b) (5.28 g., 10.65 mmol., 1.1 eq.) in dry methylene chloride (50 ml.) at 0° C. was treated with triethylamine (1.48 ml., 10.65 mmol.), followed by the product from part (c) (1.85 g., 9.68 mmol.) in dry methylene chloride (30 ml.) and benzotriazol-1-yloxytris(dimethylamino)phosphonium hexafluorophosphate (4.71 g., 10.65 mmol., 1.1 eq.). The mixture was stirred for 1 hour at 0° C. and then stirred at room temperature for 2 hours. The reaction mixture was partitioned between ethyl acetate (300 ml.) and water (150 ml.). The ethyl acetate layer was washed with 50% saturated sodium bicarbonate (200 ml.) and brine (2×200 ml.), dried over magnesium sulfate, filtered, concentrated, adsorbed onto Celite® and purified on a 7×20 cm silica gel column eluting with 40% ethyl acetate/hexane (3l.), followed by 50% (2l.) ethyl acetate/hexane affording 4.84 g. of title product. TLC (ethyl acetate: hexane, 1:1) $R_f$=0.22.

e) [S-(R*,R*)]-2-[[2-[[(Phenylmethoxy)carbonyl]amino]-4-hydroxy-1-oxobutyl]amino]-5,5-dimethoxypentanoic acid, methyl ester A solution of the product from part (d) (4.80 g., 7.18 mmol.) in methanol (70 ml.) was treated with p-toluenesulfonic acid monohydrate (300 mg.). After stirring at room temperature for 2 hours, the mixture was partitioned between ethyl acetate (400 ml.) and 25% saturated sodium bicarbonate (200 ml.). The phases were separated and the aqueous layer was extracted again with ethyl acetate (100 ml.). The combined ethyl acetate extracts were washed with brine, dried over magnesium sulfate, filtered and concentrated. The residue was purified by chromatography on a 5×20 cm silica gel column eluting with 7:3 (1l.), 8:2 (1l.) ethyl acetate:hexane followed by 10% methanol in ethyl acetate (2l.). The desired fractions were combined, concentrated and dried in vacuo to yield 2.92 g. of title product. TLC (ethyl acetate:hexane, 8:2) $R_f$=0.09.

f) [S-(R*,R*)]-2-[[2-[[(Phenylmethoxy)carbonyl]-amino]-4-(acetylthio)-1-oxobutyl]amino]-5,5-dimethoxypentanoic acid, methyl ester A 0° C. solution of triphenylphosphine (3.06 g., 11.65 mmol., 1.7 eq.) in dry tetrahydrofuran (40 ml.) was treated with diisopropyl azodicarboxylate (2.29 ml., 11.65 mmol.). The resultant white slurry was stirred for 30 minutes and then treated with a solution of the product from part (e) (2.92 g., 6.85 mmol.) in dry tetrahydrofuran followed by neat thiolacetic acid (833 μL, 11.65 mmol.). The mixture was stirred at 0° C. for 2 hours and then partitioned between ethyl acetate (300 ml.) and 50% sodium bicarbonate (200 ml.). The ethyl acetate layer was washed with brine, dried over magnesium sulfate, filtered, concentrated, adsorbed onto Celite® and dried in vacuo. The crude material was purified by chromatography on a 5×20 cm silica gel column eluting with 1:1 ethyl acetate:hexane (3l.). The desired fractions were combined, concentrated and dried in vacuo affording 2.58 g. of title product as an off-white solid. TLC (ethyl acetate:hexane, 8:2) $R_f$=0.40.

g) [S-(R*,R*)]-2-[[2-[[(Phenylmethoxy)carbonyl]-amino]-4-mercapto-1-oxobutyl]amino]-5,5-dimethoxyoentanoic acid, methyl ester A de-oxygenated (argon bubbling) solution of the product from part (f) (2.56 g., 5.28 mmol.) in methanol (50 ml.) at 0° C. was treated with sodium methoxide (25% by weight in methanol, 3.62 ml., 15.84 mmol., 3 eq.). After 10 minutes, the mixture was quenched with saturated ammonium chloride (40 ml.), diluted with water (100 ml.), and extracted with ethyl acetate (300 ml.). The ethyl acetate extract was washed with water (100 ml.) and brine (150 ml.), dried over magnesium sulfate, filtered and concentrated. The residue was purified by chromatography on a 5×20 cm silica gel column eluting with 1:1 (3l.) ethyl acetate:hexane. The desired compound was combined and concentrated to yield 1.99 g. of title product as an oil. TLC (ethyl acetate:hexane, 8:2) $R_f$=0.43.

h) [4S-(4α,7α,9aβ)]-Octahydro-4-[[(phenylmethoxy)carbonyl]amino]-5-oxopyrrolo[2,1-b][1,3]thiazepine-7-carboxylic acid, methyl ester A solution of the product from part (g) (2.16 g., 4.88 mmol.) in methylene chloride (50 ml.) was treated with Amberlyst® 15 ion exchange resin (620 mg., pre-washed successively with 6N hydrochloric acid, water, tetrahydrofuran and methylene chloride). After stirring at room temperature for 3 hours the solution was filtered, concentrated and flash chromatographed on a 5×20 cm silica gel column eluting with 6:4 ethyl acetate:hexane to afford 1.34 g. of title product as a white foam. TLC (ethyl acetate:hexane, 8:2) $R_f$=0.51.

i) [4S-(4α,7α,9aβ)]-4-Amino-octahydro-5-oxopyrrolo[2,1-b][1,3]thiazepine-7-carboxylic acid, methyl ester A solution of the product from part (h) (1.20 g., 3.17 mmol., stripped with toluene three times and dried in vacuo overnight] in dry methylene chloride (40 ml.) was treated with iodotrimethylsilane (632 μL, 4.44 mmol., 1.4 eq.) and stirred at room temperature under argon for 1.5 hours. The mixture was quenched with water (50 ml.), treated with 10% hydrochloric acid (5 ml., pH 1) and washed with ethyl acetate (50 ml.). The aqueous phase was treated with with 10% sodium hydroxide and extracted with methylene chloride (three times). The pooled extracts were dried over sodium sulfate, filtered, concentrated, and dried in vacuo to yield a 396 mg. of title product as a clear oil. TLC (10% methanol in methylene chloride) $R_f$=0.10.

j) [4S-[4α(R*),7α,9aβ]]-Octahydro-4-[(2-mercapto-1-oxo-3-phenylpropyl)amino]-5-oxopyrrolo[2,1-b][1,3]thiazepine-7-carboxylic acid A solution of (S)-2-(acetylthio)benzenepropanoic acid in dry methylene chloride was treated with triethylamine. A solution of the product from part (i) in methylene chloride was then added followed by benzotriazol-1-yloxytris(dimethylamino)phosphonium hexafluorophosphate. The resultant solution was worked-up as described in Example 5(e) to give [4S-[4α(R*),7α,9aβ]]-octahydro-4-[[2-(acetylthio)-1-oxo-3-phenylpropyl]amino]-5-oxopyrrolo[2,1-b][1,3]thiazepine-7-carboxylic acid, methyl ester.

A suspension of this methyl ester product in methanol:tetrahydrofuran, purged with argon, was cooled to 0° C. and treated with a previously purged solution of 1.0N sodium hydroxide. Work-up as described in Example 5(f) gave the title product.

EXAMPLE 7

[4S-[4α(R*),7α,9aβ]]-Octahydro-4-[(3-cyclohexyl-2-mercapto-1-oxopropyl)amino]-5-oxopyrrolo[2,1-b][1,3]thiazepine-7-carboxylic acid a) [4S-(4α,7α,9aβ)]-4-Amino-octahydro-5-oxopyrrolo-[2,1-b][1,3]thiazepine-7-carboxylic acid, methyl ester, p-toluenesulfonic acid salt A solution of [4S-(4α,7α,9aβ)]-octahydro-4-[[(phenylmethoxy)carbonyl]amino]-5-oxopyrrolo[2,1-b][1,3]thiazepine-7-carboxylic acid, methyl ester [prepared as described in Example 6(h), 738 mg., 1.95 mmol., stripped three times with toluene and dried in vacuo overnight) in dry methylene chloride (25 ml.) was treated with iodotrimethylsilane (389 μL, 2.73 mmol., 1.4 eq.) and stirred at room temperature under argon. After 2 hours the reaction was treated with additional amounts of iodotrimethyl silane (40 μL) and stirred for 30 minutes. The mixture was quenched with a 0.4M hydrochloric acid solution of methanol:dioxane (9:1; 9.7 ml.) and stirred for 5 minutes. The volatiles were removed in vacuo (Rotovap) and the residue was partitioned between water and ethyl acetate. The separated ethyl acetate layer was washed with water and the combined aqueous phase washed with ethyl acetate. The aqueous phase was cooled to 0° C. and the pH adjusted to 10.3 (monitored with pH meter) with 1.0N sodium hydroxide. The aqueous phase was extracted with methylene chloride (three times) and the aqueous phase was then saturated with salt and extracted again with methylene chloride (three times). The pooled extracts were dried over sodium sulfate, filtered, concentrated, and dried in vacuo to yield 455 mg. of the free amine as a clear oil. TLC (10% methanol in methylene chloride) R$_f$=0.28.

This free amine was dissolved in ethyl acetate (5 ml.) and treated with a solution of p-toluenesulfonic acid monohydrate (354 mg., 1 eq.) in ethyl acetate (1 ml.). White crystals immediately formed. The cystals were stored in refrigerator (5° C.) for 30 minutes and then collected by filtration washing well with ethyl ether and drying overnight in vacuo to yield 639 mg. of title product as a white solid.

b) (S)-2-(Acetylthio)-3-cyclohexylpropanoic acid, dicyclhexylamine salt

A solution of D-phenylalanine (5.20 g., 31.5 mmol.) in 2M hydrochloric acid (75 ml.) in a 500 ml. Parr hydrogenation flask was purged with nitrogen gas and treated with platinum oxide (640 mg., 2.82 mmol.). Hydrogenation was commenced at P$_o$=42.4 psi in the sealed flask, refilling as necessary. Total hydrogen uptake was 83.4 psi (theory 83.8 psi) over 6 hours. The reaction was purged with nitrogen gas and filtered through Celite®, washing the filter cake with hot water. The filtrate was concentrated to about 40 ml. and stored at 5° C. overnight. The resulting solids were collected, washed with a small amount of cold water and dried in vacuo at 60° C. to give 5.46 g. of (R)-2-amino-3-cyclohexylpropanoic acid, hydrochloride salt.

To a stirred solution of this hydrochloride salt (2.81 g., 13.5 mmol.) in 2.5N sulfuric acid (32 ml.) at room temperature was added potassium bromide (10.0 g., 84 mmol.). The reaction mixture was cooled to –4° C. and solid sodium nitrite (1.75 g., 25.4 mmol.) was added portionwise over one hour, maintaining the temperature below 0° C. The reaction foamed and an oil began to form. After addition was complete, the reaction was stirred for 1 hour and then warmed to room temperature and stirred for another hour. The reaction mixture was then extracted twice with ether, the extracts were dried (magnesium sulfate), filtered and evaporated to give 2.3 g. of (R)-2-bromo-3-cyclohexylpropanoic acid as a colorless oil.

To a stirred slurry of potassium thioacetate (1.07 g., 9.36 mmol.) in dry acetonitrile (15 ml.) at 0° C. under argon was added a solution of (R)-2-bromo-3-cyclohexylpropanoic acid (2.20 g., 9.36 mmol.) in acetonitrile (3 ml.) over 10 minutes. The reaction was warmed to room temperature and stirred 16 hours. The resulting slurry was filtered and evaporated. The residue was redissolved in ethyl acetate, washed once with 5% potassium bisulfate solution, dried (sodium sulfate) and evaporated. The oily yellow residue (2.21 g.) was dissolved in ether and treated with a solution of dicyclohexylamine (1.8 ml., 9.0 mmol.) in 5 ml. of ether. Scratching the flask surface with a glass rod provided 2.38 g. of white crystalline title product; m.p. 159°–161° C., [α]$_D$=–41.2° (c=1.0, chloroform).

Anal. calc'd. for C$_{23}$H$_{41}$NSO$_3$: C, 67.11; H, 10.04; N, 3.40; S, 7.79 Found: C, 66.95; H, 10.12; N, 3.25; S, 7.89.

c) [4S-[4α(R*),7α,9aβ]]-Octahydro-4-[[2-(acetylthio)-3-cyclohexyl-1-oxopropyl]amino]-5-oxopyrrolo[2,1-b][1,3]thiazepine-7-carboxylic acid, methyl ester A suspension of the compound (S)-2-(acetylthio)-3-cyclohexylpropanoic acid, dicyclohexylamine salt (285 mg., 0.69 mmol., 1.05 eq.) in ethyl acetate (15 ml.) was washed with 5% potassium bisulfate (3×10 ml.), 50% brine (10 ml.), and brine (10 ml.), dried (anhydrous magnesium sulfate), filtered, concentrated, stripped with methylene chloride (twice) and dried in vacuo for one hour to give (S)-2-(acetylthio)-3-cyclohexylpropanoic acid as an oil.

This free acid of was dissolved in dry methylene chloride (5 ml.), cooled to 0° C. (ice bath), and treated with triethylamine (96 μl., 0.69 mmol., 1.05 eq.), then the product from part (a) (275 mg., 0.66 mmol.), triethylamine (92 μl., 0.66 mmol.) and finally benzotriazol-1-yloxytris(dimethylamino) phosphonium hexafluorophosphate (305 mg., 0.69 mmol.). The resultant solution was stirred at 0° C. for 1 hour then at room temperature for 2 hours. The reaction mixture was concentrated, diluted with ethyl acetate, washed with 5% potassium bisulfate (20 ml.), 50% saturated sodium bicarbonate (20 ml.), brine (20 ml.), dried (anhydrous magnesium sulfate), filtered, and evaporated to dryness. The crude product was adsorbed onto Celite® and chromatographed on a silica gel column (2.5×10 cm), eluting with 40% (11.) ethyl acetate/hexane. The desired fractions were combined and concentrated, affording 246 mg. of pure title product. TLC (ethyl acetate:hexane, 8:2) R$_f$=0.53.

d) [4S-[4α(R*),7α,9aβ]]-Octahydro-4-[(3-Cyclohexyl-2-mercapto-1-oxopropyl)amino]-5-oxopyrrolo[2,1-b]-[1,3]thiazepine-7-carboxylic acid A solution of the product from part (c) (245 mg., 0.54 mmol.) in methanol (6 ml.), purged with argon for 30 minutes, cooled to 0° C. was treated dropwise with a previously purged (argon, 30 minutes) solution of 1.0N sodium hydroxide (5 ml.) maintaining the bubbling of argon throughout the addition and length of the reaction. The reaction mixture was stirred at 0° C. for 2 hours, acidified at 0° C. with 5% potassium bisulfate to pH 2 then extracted with ethyl acetate (3×20 ml.). The combined organic extracts were washed with 50% brine (20 ml.), and brine (20 ml.), dried (anhydrous magnesium sulfate), filtered, and evaporated to dryness. The residue was purified by chromatography on a 2.5×10 cm silica gel column eluting with 7:3 ethyl acetate:heptane (300 ml.) and 1% acetic acid in 7:3 ethyl acetate:heptane (500 ml.). The desired fractions were concentrated, stripped with methylene chloride and dried in vacuo to yield 172 mg. of title product as a white foam; [α]$_D$=–116.9° (c=0.5, methanol). TLC (1% acetic acid in ethyl acetate) R$_f$=0.35.

$^1$H-NMR: 400 MHz; CDCl$_3$: δ 0.91 (m, 2H), 1.22 (m, 3H), 1.44 (m, 1H), 1.55 (m, 1H), 1.68 (m's, 5H), 1.83 (m, 1H), 1.97 (m's, 2H), 2.12 (m, 1H), 2.19–2.40 (m's, 3H), 2.53 (m, 1H), 2.96 (m, 1H), 3.38 (m's, 2H), 4.62 (t, 1H, J=6.8 Hz), 4.70 (m, 1H), 5.25 (m, 1H), 7.55 (d, 1H, J=6.4 Hz).

$^{13}$C-NMR: 100 MHz; CDCl$_3$: δ 26.0, 26.1, 27.5, 31.5, 32.3, 33.0, 33.3, 35.2, 40.7, 43.0, 52.9, 60.6, 62.5, 170.9, 172.7, 175.3.

Anal. calc'd. for C$_{18}$H$_{28}$N$_2$O$_4$S$_2$: C, 53.98; H, 7.05; N, 6.99; S, 16.01 Found: C, 53.97; H, 7.18; N, 6.84, S, 15.75.

HPLC: t$_R$=16 min (>99%, UV 217); YMC S-3 ODS (C-18) 6.0×150 mm; 50% B:A-100% B:A, 25 minute linear gradient (A=90% water/methanol+0.2% phosphoric acid; B=90% methanol/water+0.2% phosphoric acid); flow rate at 1.5 ml/min.

EXAMPLE 8

[4S-[4α(R*),7α,9aβ]]-Octahydro-4-[(2-mercapto-1-oxohexyl)amino]-5-oxopyrrolo[2,1-b][1,3] thiazepine-7-carboxylic acid a) (S)-2-Bromohexanoic acid

Potassium bromide (15.9 g., 133 mmol.) was added to a stirred solution of D-norleucine (5.0 g., 38 mmol.) in 2.5N sulfuric acid (77 ml.) at room temperature. The reaction mixture was cooled to −10° C. and solid sodium nitrite (3.94 g., 57 mmol.) was added portionwise, maintaining the temperature between −10° and −5° C. After addition was complete, the foamy reaction was stirred for 1 hour and then warmed to room temperature and stirred for another hour. The reaction mixture was then extracted twice with ether, the ether extracts were washed once with water, dried (magnesium sulfate), filtered and evaporated to give 3.3 g. of crude title product.

b) (S)-2-(Acetylthio)hexanoic acid, dicyclohexylamine salt

To a stirred slurry of potassium thioacetate (2.11 g., 18.5 mmol.) in 50 ml. of dry acetonitrile at room temperature under argon was added a solution of the product from part (a) (3.27 g., 16.8 mmol.) in 26 ml. of acetonitrile. The reaction was stirred 5 hours. The resulting slurry was filtered and evaporated. The residue was redissolved in ethyl ether, washed once with 5% potassium bisulfate solution and once with brine, dried (magnesium sulfate) and evaporated. The residue was dissolved in ether (64 ml.) and treated with dicyclohexylamine (3.4 ml., 16.8 mmol.). The ethereal solution was concentrated in vacuo, and triturated from hexanes to give a white solid which was recrystallized from ethyl ether/hexanes to give the title product. The mother liquor was concentrated and recrystallized twice to provide a total yield of 2.2 g. of title product; m.p. 145°–147° C.; $[\alpha]_D$=−33.8° (c=1.08, chloroform).

c) [4S-[4α(R*),7α,9aβ]]-Octahydro-4-[[2-(acetylthio)-1-oxohexyl]amino]-5-oxopyrrolo-[2,1-b][1,3]thiazepine-7-carboxylic acid, methyl ester A suspension of the dicyclohexylamine salt product from part (b) (255 mg., 0.69 mmol., 1.05 eq.) in ethyl acetate (15 ml.) was washed with 5% potassium bisulfate (3×5 ml.), and brine (10 ml.), dried (anhydrous magnesium sulfate), filtered, concentrated, stripped with methylene chloride (twice), and dried in vacuo for one hour to give the free acid as a oil.

This oil was dissolved in dry methylene chloride (6 ml.), cooled to 0° C. (ice bath) and treated with triethylamine (96 µl., 0.69 mmol., 1.05 eq.), then [4S-(4α,7α,9aβ)]-4-amino-octahydro-5-oxopyrrolo[2,1-b][1,3]thiazepine-7-carboxylic acid, methyl ester, p-toluenesulfonic acid salt [prepared as described in Example 7(a), 275 mg., 0.66 mmol.], triethylamine (92 µl., 0.66 mmol.) and finally benzotriazol-1-yloxytris(dimethylamino)phosphonium hexafluorophosphate (305 mg., 0.69 mmol.). The resultant solution was stirred at 0° C. for one hour then at room temperature for 2 hours. The reaction mixture was concentrated, diluted with ethyl acetate, washed with 5% potassium bisulfate (20 ml.), 50% saturated sodium bicarbonate (20 ml.), brine (20 ml.), dried (anhydrous magnesium sulfate), filtered, and evaporated to dryness. The crude product was adsorbed onto Celite® and chromatographed on a silica gel column (2.5× 10 cm), eluting with 40% (11.) ethyl acetate/hexane. The desired fractions were combined and concentrated, affording 258 mg of pure title product. TLC (ethyl acetate:hexane, 8:2) $R_f$=0.54.

d) [4S-[4α(R*),7α,9aβ]]-Octahydro-4-[(2-mercapto-1-oxohexyl)amino]-5-oxopyrrolo[2,1-b][1,3]thiazepine-7-carboxylic acid A solution of the product from part (c) (255 mg., 0.54 mmol.) in methanol (5 ml.), purged with argon for 30 minutes, cooled to 0° C. was treated dropwise with a previously purged (argon, 30 minutes) solution of 1.0N sodium hydroxide (5 ml.) maintaining the bubbling of argon throughout the addition and length of the reaction. The reaction mixture was stirred at 0° C. for 2 hours, acidified at 0° C. with 5% potassium bisulfate to pH 2 then extracted with ethyl acetate (3×20 ml.). The combined organic extracts were washed with 50% brine (20 ml.) and brine (20 ml.), dried (anhydrous magnesium sulfate), filtered, and evaporated to dryness. The residue was purified by chromatography on a 2.5×10 cm silica gel column eluting with 7:3 ethyl acetate:heptane (300 ml.) and 1% acetic acid in 7:3 ethyl acetate:heptane (500 ml.). The desired fractions were concentrated, stripped with methylene chloride and dried in vacuo to yield 170 mg. of title product as a white foam; $[\alpha]_D$=−135.1° (c=0.5, methanol). TLC (1% acetic acid in ethyl acetate) $R_f$=0.32.

$^1$H-NMR: 400 MHz; CDCl$_3$: δ 0.89(t, 3H, J=7 Hz), 1.32(m, 4H), 1.73(m, 1H), 1.96(m, 2H), 2.00(d, 1H, J=8.6 Hz), 2.11(m, 1H), 2.32 (m's, 3H), 2.52(m, 1H), 2.98(m, 1H), 3.32(m's, 2H), 4.61 (t, 1H, J=7.1 Hz), 4.72 (m, 1H), 5.25 (m, 1H), 7.63 (d, 1H, J=6.4 Hz).

$^{13}$C-NMR: 100 MHz; CDCl$_3$: δ 13.8, 22.2, 27.6, 29.2, 31.4, 32.6, 33.1, 35.3, 43.0, 52.8, 60.5, 62.42, 170.7, 172.5, 174.0.

Anal. calc'd for $C_{15}H_{24}O_4N_4S_2O$•0.08 $H_2O$: C, 49.79; H, 6.73; N, 7.74; S, 17.72 Found: C, 49.90; H, 6.92; N, 7.63, S, 17.57.

HPLC: $t_R$=9.4 min (>99%, UV 220); YMC S-3 ODS (C-18) 6.0×150 mm; 50% B:A-100% B:A, 25 minute linear gradient (A=90% water/methanol+0.2% phosphoric acid); B=90% methanol/water+0.2% phosphoric acid); flow rate at 1.5 ml/min.

EXAMPLE 9

[4S-[4α(R*),7α,9aβ]]-Octahydro-4-[(2-mercapto-1-oxo-4-methylpentyl)amino]-5-oxopyrrolo[2,1-b][1,3]thiazepine-7-carboxylic acid a) (S)-2-Bromo-4-methylpentanoic acid

Potassium bromide (9.5 g., 80 mmol.) was added to a stirred solution of D-leucine (3.0 g., 23 mmol.) in 2.5N sulfuric acid (47 ml.) at room temperature. The reaction mixture was cooled to −10° C. and solid sodium nitrite (2.4 g., 34 mmol.) was added portionwise, maintaining the temperature between −10° and −5° C. After addition was complete, the reaction was stirred for 1 hour and then warmed to room temperature and stirred for another hour. The reaction mixture was then extracted twice with ether, the ether extracts were washed once with water, dried (magnesium sulfate), filtered and evaporated to give 2.7 g. of crude title product.

b) (S)-2-(Acetylthio)-4-methylpentanoic acid, dicyclohexylamine salt

To a stirred slurry of potassium thioacetate (1.7 g., 15.0 mmol.) in 50 ml. of dry acetonitrile at room temperature under argon was added a solution of the product from part (a) (2.6 g., 13 mmol.) in 17 ml. of acetonitrile. The reaction was stirred 4 hours. The resulting slurry was filtered and evaporated. The residue was redissolved in ethyl ether, washed once with 5% potassium hydrogen sulfate solution and once with brine, dried (magnesium sulfate) and evaporated. The residue was dissolved in ether (64 ml.) and treated with dicyclohexylamine (2.7 ml., 14 mmol.). A white solid immediately began precipitating from the solution. The solution was filtered and the white solid collected to give 2.0 g. of title product; m.p. 153°–158° C.; $[\alpha]_D=-54.5°$ C. (c=0.61, chloroform).

c) [4S-[4α(R*),7α,9aβ]]-Octahydro-4-[[2-(acetylthio)-1-oxo-4-methylpentyl]amino]-5-oxopyrrolo[2,1-b][1,3]thiazepine-7-carboxylic acid, methyl ester A stirred suspension of the dicyclohexylamine salt product from part (b) (234 mg., 0.63 mmol.) in ethyl acetate (15 ml.) was washed with 5% aqueous potassium bisulfate (3×5 ml.). The organic extract was dried (anhydrous magnesium sulfate), filtered and evaporated twice from hexane. The resulting oil was dissolved in methylene chloride (6 ml.) and stirred under nitrogen at 0° C. To this solution was added triethylamine (88 µl., 0.63 mmol.), then [4S-(4α,7α,9aβ)]-4-amino-octahydro-5-oxopyrrolo[2,1-b][1,3]thiazepine-7-carboxylic acid, methyl ester, p-toluenesulfonic acid salt [prepared as described in Example 7(a), 249 mg., 0.6 mmol.], an additional amount of triethylamine (84 µl., 0.60 mmol.) and, after 10 minutes, benzotriazol-1-yloxytris (dimethylamino)phosphonium hexafluorophosphate (279 mg., 0.63 mmol.). After one hour, the reaction was warmed to room temperature and stirred 2 hours. The resulting colorless solution was evaporated at less than 30° C. and the oily residue redissolved in ethyl acetate. The solution was washed once with 5% potassium bisulfate solution, once with saturated sodium bicarbonate solution and once with brine. The organic layer was dried (magnesium sulfate), filtered and evaporated onto 5 g. of silica gel. Purification by flash chromatography (2.5×15 cm column, eluting with 1:1 ethyl acetate/hexanes) provided 203 mg. of title product as a white solid; m.p. 101°–103° C. $[\alpha]_D=-157.5°$ (c=1.04, chloroform). TLC (ethyl acetate:hexane, 1:1) $R_f=0.19$.

d) [4S-[4α(R*),7α,9aβ]]-Octahydro-4-[(2-mercapto-1-oxo-4-methylpentyl)amino]-5-oxopyrrolo[2,1-b][1,3]thiazepine-7-carboxylic acid A solution of the product from part (c) (184 mg., 0.44 mmol.) in 5 ml. of methanol was purged with nitrogen for 10 minutes and cooled to 0° C. To this solution was added dropwise 5 ml. of nitrogen-purged 1M sodium hydroxide. Nitrogen was slowly bubbled through the solution during the reaction. After 2 hours, the reaction was acidified with 2 ml. of 6M hydrochloric acid, extracted twice with ethyl acetate and the extracts combined, dried (magnesium sulfate) and evaporated. Re-evaporation from hexanes and trituration of the residue in methanol/water provided 132 mg. of title product as a crystalline solid, m.p. 94°–96° C.; $[\alpha]_D=-158.6°$ (c=0.42, methanol). TLC (ethyl acetate:hexane:acetic acid, 4:4:0.1) $R_f=0.13$.

Anal. calc'd. for $C_{15}H_{24}N_2S_2O_4\cdot 0.75\ H_2O$: C, 48.17; H, 6.87; N, 7.49; S, 17.15 Found: C, 48.33; H, 6.51; N, 7.37; S, 16.82.

HPLC: $R_f=17.6$ min; (99.2%) YMC S-3 ODS (C-18) 6.0×150 mm; 0% to 100% B:A, 25 min linear gradient and 15 min hold, 1.5 mL/min;

A=90% water/methanol+0.2% phosphoric acid;
B=90% methanol/water+0.2% phosphoric acid; 220 nm.

EXAMPLE 10

[4S-[4α(R*),7α,10aβ]]-Octahydro-4-[(2-mercapto-1-oxo-3-phenylpropyl)amino]-5-oxo[1,4]oxazino[3,4-b][1,3]oxazepine-7-carboxylic acid a) 2,2,2-Trichloroacetimidoic acid, 2-propenyl ester A suspension of 80% sodium hydride (945 mg., 31.5 mmol.; washed twice with 25 ml. of hexane) in dry ether (30 ml.) was treated dropwise with a solution of 2-propen-1-ol (21.4 ml., 18.3 g., 315 mmol.), in dry ether (45 ml.), stirred for 20 minutes at room temperature under argon and then cooled to 0° C. (ice-salt bath). Trichloroacetonitrile (30 ml. or 42.3 g., 0.30 mole) was added over a period of 15 minutes and the brownish solution was stirred at 0° C. for 40 minutes, at 10° C. for 10 minutes and at room temperature for 10 minutes. The reaction mixture was concentrated to a syrup, treated with a solution of methanol (1.2 ml.) in pentane (30 ml.) and stirred vigorously for 5.0 minutes. The light brown precipitates were filtered off, washed with pentane (2×30 ml.) and the combined filtrates concentrated down to a light brown liquid. The liquid was re-dissolved in pentane (30 ml.), stirred for a few minutes, and the resulting suspension filtered, and the precipitates obtained washed with pentane (30 ml.), repeating the procedure at least one more time. The clear filtrate was concentrated and dried in vacuo to give 54.0 g. of title compound as a light red-colored liquid. This material was stored as a solution in hexane at 10° C.

b) N-Phthaloyl-L-serine, methyl ester

A suspension of L-serine, methyl ester, hydrochloride, (25 g., 161 mmol.) in water (350 ml.) was diluted with dioxane (250 ml.) and the resulting clear solution treated with solid sodium carbonate (17 g., 1.0 eq.) followed by N-carbethoxyphthalimide (37 g., 1.05 eq.). The reaction mixture was stirred at room temperature for 2.5 hours under argon. The mixture was extracted with ethyl acetate (3×500 ml.) and the combined organic extracts were washed successively with 5% sodium bicarbonate (250 ml.), 5% potassium bisulfate (250 ml.) and brine (250 ml.), dried (anhydrous sodium sulfate), filtered, evaporated to dryness and dried in vacuo. The product mixture was chromatographed on a silica gel column (Merck), eluting the column with ethyl acetate:hexane mixtures (1:3; 1:2) and the desired fractions were combined, evaporated to dryness and dried in vacuo to give 31 g. of title compound as a thick syrup. TLC (ethyl acetate:hexane, 1:1) $R_f=0.52$.

c) N-phthaloyl-O-(2-propenyl)-L-serine, methyl ester

A solution of the product from part (b) (7.37 g., 29.5 mmol.) in dry methylene chloride (30 ml.) was treated with a solution of the product from part (a) (11.97 g., 59.1 mmol., 2 eq.) in cyclohexane (60 ml.) followed by trifluoromethanesulfonic acid (0.37 ml.) and the reaction mixture was stirred at room temperature for 20 hours under argon. The precipitates were filtered off, washed with a minimal amount of methylene chloride and the combined filtrates were washed with 5% sodium bicarbonate (30 ml.) and water (30 ml.), dried (anhydrous sodium sulfate), filtered, evaporated to dryness and dried in vacuo. The crude product mixture was chromatographed on a silica gel column (Merck), eluting the column with ethyl acetate:hexane (1:9). The desired fractions were combined, evaporated to dryness and dried in vacuo to give 7.56 g. of title compound as a clear thick syrup. TLC (ethyl acetate: hexane, 1:1) $R_f=0.70$.

d) N-phthaloyl-O-(acetaldehyde)-L-serine, methyl ester

A solution of the product from part (c) (2.5 g., 8.64 mmol.) in a mixture of dry methylene chloride (46.4 ml.) and methanol (4.6 ml.) was cooled to −78° C. (dry ice-acetone bath) and treated with ozone until a blue color persisted (about 15 minutes). The mixture was then purged with nitrogen for 10 minutes (until the blue color disappeared), treated with dimethylsulfide (14.0 ml., 0.19 mole, 22.1 eq.), warmed to room temperature and stirred for 2.5 hours under nitrogen. The reaction mixture was evaporated to dryness and the residual syrup dissolved in ethyl acetate (50 ml.), washed with water (15 ml.) and brine (15 ml.), dried (anhydrous magnesium sulfate), filtered, evaporated to dryness and dried in vacuo.

The crude product was chromatographed on a silica gel column (Merck), eluting the column with ethyl acetate:hexane mixtures (1:9; 1:4; 1:2) to give 1.54 g. of title product. TLC (ethyl acetate:hexane, 1:1) $R_f$=0.33.

e) N-Phthaloyl-O-(2,2-dimethoxyethyl)-L-serine, methyl ester

A solution of the product from part (d) (1.54 g., 5.29 mmol.) in a mixture of dry methylene chloride (8.3 ml.) and dry methanol (8.3 ml.), was treated with trimethylorthoformate (0.84 ml., 7.68 mmol., 1.45 eq.) and p-toluenesulfonic acid monohydrate (92 mg.). The reaction mixture was stirred at room temperature under argon for 2.5 hours then partitioned between ethyl acetate (50 ml.) and saturated sodium bicarbonate (15 ml.). The organic phase was washed with water (15 ml.) and brine (15 ml.), dried (anhydrous sodium sulfate), filtered, evaporated to dryness and dried in vacuo. The crude product was chromatographed on a silica gel column (Merck), eluting the column with ethyl acetate:hexane (1:4) to give 1.35 g. of title product as a thick clear syrup. TLC (ethyl acetate:hexane, 1:1) $R_f$=0.58.

f) O-(2,2-Dimethoxyethyl)-L-serine, methyl ester

A solution of the product from part (e) (2.0 g., 5.93 mmol.) in dry methanol (14 ml.) was treated with hydrazine hydrate (0.30 ml., 6.1 mmol.) and stirred at room temperature for 4 days under argon. The resulting suspension was filtered, washing the precipitates with methanol (2×14 ml.) and the filtrate was concentrated to dryness. The syrup was re-dissolved in methylene chloride and filtered two more times until no more precipitates were obtained. The clear filtrate was concentrated to give 1.17 g. of title product as a light yellow syrup. TLC (methylene chloride:methanol, 9:1) $R_f$=0.54. g) N-[(Phenylmethoxy)carbonyl]-O-[(1,1-dimethylethyl)dimethlsilyl]-L-homoserine A solution of N-[(phenylmethoxy)carbonyl]-L-homoserine [prepared as described in Example 6(a), 3.0 g., 11.85 mmol.] in dry dimethylformamide (65 ml.) was treated with [(1,1-dimethylethyl)dimethylsilyl chloride (10.72 g., 71.1 mmol.) and imidazole (9.65 g, 0.14 mol.) and stirred at room temperature under argon for 24 hours. The reaction mixture was diluted with methanol (207 ml.), stirred for another 24 hours at room temperature and then concentrated to a syrup. The residual syrup was dissolved in ethyl acetate (200 ml.), washed with 10% citric acid (2×75 ml) and brine, dried (anhydrous sodium sulfate), filtered, evaporated to dryness and dried in vacuo. The crude product mixture was chromatographed on a silica gel column (Merck), eluting the column with ethyl acetate:hexane (1:1) followed by ethyl acetate:acetic acid (99.5: 0.5). The desired fractions were combined, concentrated and evaporated several times from toluene to give 3.56 g. of title compound as a waxy solid. TLC (ethyl acetate:acetic acid, 95:5) $R_f$=0.82.

h) N-[O-[(1,1-Dimethylethyl)dimethylsilyl]-N-[(phenylmethoxy)carbonyl]-L-homoseryl]-O-(2,2-dimethoxyethyl)-L-serine, methyl ester A solution of the product from part (g) (2.18 g., 5.93 mmol.) in dry methylene chloride was cooled to 0° C. (ice-salt bath) and treated sequentially with a solution of the product from part (f) (1.71 g., 5.65 mmol.) in dry methylene chloride (5 ml), triethylamine (0.78 ml., 5.65 mmol.) and benzotriazol-1-yloxytris(dimethylamino)phosphonium hexafluorophosphate (2.63 g., 6.0 mmol.). The reaction mixture was stirred at 0° C. for 30 minutes and at room temperature for one hour and 45 minutes. The reaction mixture was partitioned between ethyl ether (2×100 ml.) and water (30 ml.) and the combined organic extracts were washed with 50% saturated sodium bicarbonate (20 ml.) and brine (25 ml.), dried (anhydrous sodium sulfate), filtered, evaporated to dryness and dried in vacuo. The crude product mixture was chromatographed on a silica gel column (Merck), eluting the column with ethyl acetate:hexane mixtures (1:4; 1:3; 1:1) to give 2.38 g. of title product. TLC (ethyl acetate:hexane, 1:1) $R_f$=0.40.

i) [4S-(4α,7α,10aβ) ]-Octahydro-4-[[(phenylmethoxy)carbonyl]amino]-5-oxo[1,4]oxazino [3,4-b][1,3]oxazepine-7-carboxylic acid, methyl ester A solution of the product from part (h) (1.0 g., 1.8 mmol.) in dry methylene chloride (50 ml.) was treated with Amberlyst® 15 ion exchange resin (acid form) and methanol (0.1 ml.) and the resulting mixture was stirred at room temperature under argon for three days. The resin was filtered off, washed with a small amount of methylene chloride and the filtrate concentrated to a syrup. The crude product mixture was chromatographed on a silica gel column, eluting the column with ethyl acetate:hexane (1:1) to give 339 mg. of title product. TLC (ethyl acetate:hexane, 3:1) $R_f$=0.53.

j) [4S-(4α,7α,10aβ)]-Octahydro-4-amino-5-oxo[1,4] oxazino[3,4-b][1,3]oxazepine-7-carboxylic acid, methyl ester A solution of the product prepared as described part (i) (771 mg., 2.04 mmol.) in dry methanol (25 ml.) was treated with 10% palladium on carbon catalyst (125 mg.) and hydrogenated (balloon) at room temperature for 16 hours. The reaction mixture was filtered through a Celite® pad and the pad was washed with methanol (2×25 ml.). The clear filtrate was evaporated to dryness and dried in vacuo to give 448 mg. of title product as a syrup. TLC (methylene chloride:methanol, 9:1) $R_f$=0.22.

k) [4S-[4α(R*),7α,10aβ]]-Octahydro-4-[[2-(acetylthio)-1-oxo-3-phenylpropyl]amino]-5-oxo[1, 4]oxazino[3,4-b][1,3]oxazepine-7-carboxylic acid, methyl ester The dicyclohexylamine salt of (S)-2-(acetylthio) benzenepropanoic acid (813 mg., 2.01 mmol.) was suspended in ethyl acetate (70 ml.), washed with 5% potassium bisulfate (5×9.3 ml.) and brine (9.3 ml.), dried (anhydrous magnesium sulfate), filtered, evaporated to dryness and dried in vacuo.

This free acid was dissolved in dry methylene chloride (12 ml.), cooled to 0° C. (ice-salt bath) and treated sequentially with a solution of the product from part (j) (448 mg., 1.84 mmol.) in dry methylene chloride (4.0 ml.), triethylamine (0.25 ml., 1.80 mmol.) and benzotriazol-1-yloxytris (dimethylamino)phosphonium hexafluorophosphate (823 mg., 1.86 mmol.). The reaction mixture was stirred at 0° C. for one hour and at room temperature for 2 hours under argon. The reaction mixture was stripped to dryness and the syrup obtained was re-dissolved in ethyl acetate (60 ml.), washed with 0.5 hydrochloric acid (2×11 ml.), water (11 ml.) and brine (11 ml.), dried (anhydrous sodium sulfate), filtered, evaporated to dryness and dried in vacuo. The crude product mixture was chromatographed twice on a silica gel column (Merck), eluting each column with ethyl acetate- :hexane mixtures (1:1; 1:2) to give 665 mg. of title product as a syrup. TLC (ethyl acetate:hexane, 3:1) $R_f$=0.30.

l) [4S-[4α(R*),7α,10aβ]]-Octahydro-4-[(2-mercapto-1-oxo-3-phenylpropyl)amino]-5-oxo[1,4]oxazino[3,4-b][1,3]oxazepine-7-carboxylic acid A solution of the product from part (k)(650 mg., 1.44 mmol.) in methanol (13 ml.), was purged with argon for 30 minutes, cooled down to 0° C. (ice-salt bath) and treated dropwise with a solution of 1.0N sodium hydroxide (5.84 ml., previously purged with argon for 30 minutes), maintaining the bubbling of argon throughout the addition and length of the reaction. The reaction mixture was stirred at 0° C. for 5.0 hours and quenched at 0° C. with 5% potassium bisulfate (25.4 ml.). The mixture was warmed to room temperature, extracted with ethyl acetate (3×50 ml.) and the combined organic extracts were washed with brine (15 ml.), dried (anhydrous sodium sulfate), filtered, evaporated to dryness and dried in vacuo. The crude product was triturated with hexane:methylene chloride (130:7) and the solid obtained chromatographed on a silica gel column (Merck), eluting the column with ethyl acetate:hexane mixtures (1:2; 1:1) followed by methylene chloride:methanol:acetic acid (100:4:0.2). The desired fractions were combined, evaporated to dryness and evaporated several times from toluene to give 364 mg. of title product which was dried in vacuo for 9.0 hours. The resulting product was then triturated with methylene chloride:hexane (1:10), hexane (50 ml.) and pentane (2×50 ml.), stirring with the first 50 ml. for 4 hours and the next 50 ml. of pentane overnight under argon. The solvent was decanted and the solid dried in vacuo for 6.0 hours to give pure title product as a solid amorphous foam; $[\alpha]_D$=−49.1° (c=0.48, methanol). TLC (toluene:acetic acid, 5:1) $R_f$=0.17.

Anal. calc'd. for $C_{18}H_{22}N_2O_6S \cdot 0.56\ H_2O$: C, 53.45; H, 5.76; N, 6.93; S, 7.92 Found: C, 53.45; H, 5.53; N, 6.75; S, 7.48.

HPLC: $R_t$=10.45 min.; (98.3%); YMS S-3 ODS (c=18) 6.0×150 mm; 44% (10% water–90% methanol–0.2% phosphoric acid)/56% (90% water–10% methanol–0.2% phosphoric acid), isocratic; 1.5 ml/min. [4S-[4α(R*),7α,10aβ]]-Octahydro-4-[(2-mercapto-1-oxo- 3-phenylpropyl)amino]-5-oxo-7H-pyrido[2,1-b][1,3]thiazepine-7-carboxylic acid The product of Example 3 was also prepared as follows:

a) N-[(Phenylmethoxy)carbonyl]-O-[(1,1-dimethylethyl)dimethylsilyl]-L-homoserine

[(1,1-Dimethylethyl)dimethylsilyl]chloride (37.5 g., 249 mmol.) was added to a solution of N-[(phenylmethoxy)carbonyl]-L-homoserine [prepared as described in Example 6(a), 41.56 mmol.] in dimethylformamide (125 ml.), followed by imidazole (33.95 g., 498 mmol.). The resulting light yellow solution was stirred at room temperature for 22 hours. Methanol (500 ml.) was added, the reaction mixture was stirred for an additional 6 hours, and then the methanol and most of the dimethylformamide were removed in vacuo. The remaining residue was taken up into ethyl acetate (800 ml.), washed with 10% citric acid (2×300 ml.), and the combined aqueous phase was extracted with ethyl acetate (300 ml.). The combined ethyl acetate phase was washed with water and brine, dried (sodium sulfate), concentrated, and the residue was evaporated with hexane to form a white powder. This powder was dried in vacuo to give 12.942 g. of title product.

b) [S-(R*,R*)]-2-[[4-[[(1,1-Dimethylethyl)dimethylsilyl]oxy]-1-oxo-2-[[(phenylmethoxy)carbonyl]amino]butyl]amino]-6,6-dimethoxyhexanoic acid, methyl ester To a solution of the product from part (a) (22.78 g., 61.97 mmol.) in methylene chloride (100 ml.) cooled at 0° C. was added N-methylmorpholine (6.81 ml., 61.97 mmol.), followed by hydroxybenzotriazole (8.37 g., 61.97 mmol.), (S)-2-amino-6,6-dimethoxyhexanoic acid, methyl ester [prepared as described in Example 11e), 10.6 g., 51.64 mmol.] in methylene chloride (50 ml.), and then 1-ethyl-3-(3-dimethylaminopropyl) carbodiimide (11.88 g., 61.97 mmol.). The reaction mixture was stirred at 0° C. for one hour, then at room temperature overnight. The reaction mixture was concentrated in vacuo and the residue was diluted with ethyl acetate (600 ml.), washed with 5% potassium bisulfate (200 ml.), 0.5N sodium hydroxide (200 ml.), water, and brine, and dried (sodium sulfate). The filtrate was concentrated and the residue taken up in ethyl ether (150 ml.). The resulting suspension was filtered and the collected solid was washed thoroughly with ethyl ether. The filtrate was concentrated in vacuo to dryness to afford 30 g. of crude title product as an oily compound which was used in the next reaction without purification. TLC (8:2, ethyl acetate:hexane) $R_f$=0.55.

c) [S-(R*,R*)]-2-[[4-Hydroxy-1-oxo-2-[[(phenylmethoxy)carbonyl]amino]butyl]amino]-6,6-dimethoxyhexanoic acid, methyl ester To a solution of the product from part (b) (30 g.) in methanol (150 ml.) cooled at 0° C. was added para-toluenesulfonic acid monohydrate (1.96 g.). The reaction mixture was stirred at 0° C. for 2 hours before quenching with aqueous sodium bicarbonate solution (1,3 g. of sodium bicarbonate in 100 ml. of water). The mixture was concentrated in vacuo and the residue partitioned between ethyl acetate (400 ml.) and water (150 ml.). The separated aqueous phase was extracted with ethyl acetate (2×150 ml.). The combined ethyl acetate layers were washed with 10% sodium bicarbonate, brine (2 times), dried (sodium sulfate), filtered and evaporated to dryness. The residue was flash chromatographed on a 10×25 cm silica gel column eluting with 80% ethyl acetate in hexane (5l.), ethyl acetate (3 l.) and 2% methanol in ethyl acetate (5 l.). The desired fractions were combined and concentrated, and dried in vacuo to give 17.45 g. of title product as a pale yellow oil. TLC (8:2, ethyl acetate:hexane) $R_f$=0.17.

d) [S-(R*,R*)]-2-[[4-[(Methanesulfonyl)oxy]-1-oxo-2-[[(phenylmethoxy)carbonyl]amino]butyl]amino]-6,6-dimethoxyhexanoic acid, methyl ester To a solution of the product from part (c) (17.40 g., 39.50 mmol.) (stripped with toluene three times and dried in vacuo overnight) in dry methylene chloride (250 ml.) cooled at −15° C. (ice/acetone) was added triethylamine (8.26 ml., 59.28 mmol., freshly distilled), followed by methanesulfonyl chloride (3.67 ml., 47.4 mmol.) dropwise. The reaction mixture was stirred at −15° C. for 30 minutes, then quenched with saturated ammonium chloride solution (100 ml.). After stirring for 5 minutes, the mixture was diluted with ethyl acetate (600 ml.) and washed with 5% potassium bisulfate, brine, dried (sodium sulfate), filtered and evaporated to dryness. The residue was dried in vacuo to give 20.40 g. of title compound as a yellow oil which was used in the next reaction without purification. TLC (8:2, ethyl acetate: hexane) R$_f$=0.35.

e) [S-(R*,R*)]-2-[[4-(Acetylthio)-1-oxo-2-[[ (phenylmethoxy)carbonyl]amino]butyl]amino]-6,6-dimethoxyhexanoic acid, methyl ester To a solution of thioacetic acid (5.09 ml., 71.10 mmol.) in methanol (100 ml.) was added cesium carbonate (10.81 g., 33.18 mmol.). The resulting solution was concentrated in vacuo. The solid was triturated with dry acetone (3 times) and then dried in vacuo over phosphorus pentoxide overnight to give cesium thioacetate.

A solution of the product from part (d) (20.40 g., 39.50 mmol.) in dry dimethylformamide (150 ml.) was added via cannula to a suspension of cesium thioacetate (10.576 g., 50.85 mmol.) in dimethylformamide (50 ml.). The resulting yellow solution was stirred under argon at room temperature overnight, then concentrated at high vacuum to remove most of the dimethylformamide. The residue was taken into ethyl acetate (1 l.) and washed with 10% sodium bicarbonate (200 ml.), water (4×200 ml.), brine (400 ml.) and dried (sodium sulfate). The filtrate was concentrated and the residue evaporated with toluene (3 times), then dried in vacuo to afford 20 g. of title compound as a light yellow solid which was used for the next reaction without purification. TLC (8:2; ethyl acetate:hexane) R$_f$=0.47.

f) [S-(R*,R*)]-2-[[4-Mercapto-1-oxo-2-[[ (phenylmethoxy)carbonyl]amino]butyl]amino]-6,6-dimethoxyhexanoic acid, methyl ester A solution of the product from part (e) (20 g., (20 g., 39.50 mmol.) in methanol (250 ml.) cooled at 0° C. was purged with argon for 15 minutes. With continuous argon purging, a 25% (weight/weight, density= 0.945) sodium methoxide solution in methanol (9.17 ml., 40 mmol.) was added dropwise. After stirring for 5 minutes, the reaction was quenched with saturated ammonium chloride solution (200 ml.) and the mixture partitioned between ethyl acetate (1 l.) and water (200 ml.). The aqueous phase was extracted with ethyl acetate (200 ml.). The combined ethyl acetate extract was washed with saturated ammonium chloride solution (400 ml.), brine (400 ml.), dried (sodium sulfate), filtered and concentrated in vacuo to give 17.5 g. of title product as a yellow oil which was used for the next reaction without purification. TLC (8:2, ethyl acetate:hexane) R$_f$=0.45.

g) [4S-(4α,7α,10aβ)]-Octahydro-4-[[ (phenylmethoxy)carbonyl]amino]-5-oxo-7H-pyrido [2,1-b][1,3]thiazepine-7-carboxylic acid, methyl ester To a solution of the product from part (f) (17.5 g., 38.3 mmol.) in methylene chloride (600 ml.) was added Amberlyst® 15 ion exchange resin (6 g., pretreated with 6N hydrochloric acid, water, tetrahydrofuran, and methylene chloride and dried). The suspension was stirred under argon at room temperature for 18 hours and filtered. The filtrate was concentrated and the residue adsorbed on Celite®, purified on a 10×30 cm silica gel column eluting with 20–30% of ethyl acetate in hexane. The desired fractions were combined and evaporated in vacuo to dryness to afford 9.18 g. of title product as a yellow oil. TLC (1:1, ethyl acetate:hexane) R$_f$=0.32.

h) [4S-(4α,7α,10aβ)]-Octahydro-4-amino-5-oxo-7H-pyrido[2,1-b][1,3]thiazepine-7-carboxylic acid, methyl ester To a solution of solution of the product from part (g) (9.1 g., 23.19 mmol., evaporated with toluene three times and dried in vacuo overnight) in dry methylene chloride (150 ml.) was added iodotrimethylsilane (4.95 ml., 34.78 mmol.) dropwise. The resulting yellow solution was stirred under argon at room temperature for 1.5 hours, then quenched with 0.4N hydrochloric acid in methanol/dioxane (120 ml.). The volatiles were removed in vacuo and the residue partitioned between ether (500 ml.) and water (700 ml.). The organic phase was extracted with 0.1 N hydrochloric acid (150 ml.) and the combined acidic aqueous extract cooled to 0° C., basified with 1N sodium hydroxide to pH 10.5 (monitored with a pH meter), then extracted with methylene chloride (4×400 ml.). The combined organic extracts were washed with brine, dried (sodium sulfate), filtered and concentrated in vacuo to afford 6.45 g. of title product as a yellow oil, which was used for the next reaction without further purification. TLC (1:9, methanol:methylene chloride) R$_f$=0.20.

i) [4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid A cold (0° C.) solution of (S)-(2-acetylthio) benzenepropanoic acid and triethylamine in methylene chloride was treated with a solution of the product from part (h) in methylene chloride followed by benzotriazol-1-yloxytris (dimethylamino)phosphonium hexafluorophosphate. The reaction was worked up according to the procedure described in Example 3 (c) to afford [4S-[4α(R*),7α,10aβ] ]-octahydro-4-[[2-(acetylthio)-1-oxo-3-phenylpropyl] amino]-5-oxo-7H-pyrido[2,1-b][1,3]thiazepine-7-carboxylic acid, methyl ester.

A solution of this methyl ester product in deoxygenated methanol was treated with 1N sodium hydroxide according to the procedure of Example 3(d) to afford the title product.

EXAMPLE 12

[4S-[4α(R*),7α,10aβ]]-Octahydro-4-[[2-(mercaptomethyl)-1-oxo-3-phenylpropyl]amino]-5-oxo-7H-pyrido [2,1-b][1,3]thiazepine-7-carboxylic acid a) (S)-2-[(Acetylthio)methyl]benzenepropanoic acid, ephedrine salt A solution of (1R,2S)-(−)-ephedrine (17.3 g., 105 mmol.) in diethyl ether (175 ml.) was added in one portion to a solution of 2-[(acetylthio)methyl]benzenepropanoic acid (50.0 g., 210 mmol.) in diethyl ether (175 ml.). After standing at room temperature for 16 hours, the crystallized ephedrine salt was collected by filtration (19.7 g.); m.p. 114°–125°; [α]$_D$=−40.6° (c=1, methanol). An additional amount of solid [8.9 g, m.p. 121°–126°; [α]$_D$=−47.2° (c=1, methanol)] separated from the filtrate after remaining at room temperature for 20 hours. The solids were combined and recrystallized from acetonitrile (1500 ml.). After 16 hours at room temperature, 20.8 g. of solid was collected; m.p. 125°–130° C.; [α]$_D$=−48.9° (c=1, methanol). This material was recrystallized in the same manner from acetonitrile (300 ml.) to give 18.7 g., m.p. 128°–130°; [α]$_D$=−48.9° (c=1, methanol). A third recrystallization from acetonitrile (225 ml.) afforded 17.4 g of solid (S)-2-[(acetylthio) methyl]benzenepropanoic acid, ephedrine salt; m.p. 128°–129°; [α]$_D$=−50.1° (c=1, methanol).

Anal. calc'd. for $C_{12}H_{14}O_3S \cdot C_{10}H_{15}NO$: C, 65.48; H, 7.24; N, 3.47; S, 7.95 Found: C, 65.46; H, 7.34; N. 3.21; S, 8.00.

b) [4S-[4α(R*),7α,10aβ]]-Octahydro-4-[[2-[ (acetylthio)methyl]-1-oxo-3-phenylpropyl]amino]-5-oxo-7H-pyrido[2,1-b][1,3]thiazepine-7-carboxylic acid, methyl ester A stirred suspension of the ephedrine salt from part (a) (333.1 mg., 0.822 mmol.) in ethyl acetate (5 ml) was washed three times with 5 ml portions of 1N hydrochloric acid solution. The organic extracts were combined, washed with brine, dried (magnesium sulfate), filtered, concentrated and dried in vacuo for 30 minutes. The resulting oil was dissolved in methylene chloride (2 ml) and stirred under nitrogen at 0° C. To this solution was added a solution of [4S-(4α,7α,10aβ)]-octahydro-4-amino-5-oxo-7H-pyrido[2,1-b][1,3]thiazepine-7-carboxylic acid, methyl ester [200.0 mg, 0.774 mmol., prepared as described in Example 3(c)] in methylene chloride (6 ml), then triethylamine (0.113 ml, 0.813 mmol) and finally benzotriazol-1-yloxytris (dimethylamino)phosphonium hexafluorophosphate (360.0 mg., 0.813 mmol.) The reaction was stirred at 0° C. and allowed to slowly warm to room temperature. After 19 hours, the reaction was concentrated in vacuo and the residue was dissolved in ethyl acetate. The solution was washed once with a 5% solution of potassium bisulfate (20 ml), once with a saturated solution of sodium bicarbonate (20 ml), and once with brine. The organic layer was dried (magnesium sulfate), filtered and concentrated to a yellow foam. Purification by flash chromatography (silica gel, 230–400 mesh under 10–20 psi of nitrogen pressure) eluting with 4:3 ethyl acetate/hexane gave 303 mg of product as a clear oil.

c) [4S-[4α(R*),7α,10aβ]]-Octahydro-4-[[2-(mercaptomethyl)-1-oxo-3-phenylpropyl]amino]-5-oxo-7H-pyrido[2,1-b][1,3]thiazepine-7-carboxylic acid A solution of the product from part (b) (303.1 mg., 0.635 mmol) in methanol (6.5 ml, deoxygenated via nitrogen bubbling) was cooled to 0° C. and treated with 1N sodium hydroxide (6.5 ml, deoxygenated via nitrogen bubbling). After stirring for one hour at 0° C. while purging continuously with nitrogen, the reaction was warmed to room temperature. After a total of three hours, the reaction was acidified to pH 1 with 5% potassium bisulfate and extracted with ethyl acetate. The organic layers were combined, washed with water, brine, dried (sodium sulfate), filtered, and concentrated in vacuo to give 219 mg of title product as a white solid; m.p. 200° C. (decomp.). TLC (6:0.01:3.99 ethyl acetate/acetic acid/hexane) $R_f$=0.15.

HPLC: $t_R$=26.3 min, impurity at 27.0 min.; YMC S-3 ODS (C-18) 6.0×150 mm; 0% to 100% B: A, 30 min. linear gradient and 10 min. hold, 1.5 ml/min.; A=90% water:methanol+0.2% phosphoric acid, B=90% methanol:water+0.2% phosphoric acid; 220 nm.

Anal. calc'd for $C_{20}H_{26}O_4N_2S_2 \cdot 0.11 \ C_4H_8O_2 \cdot 0.07 \ CH_2Cl_2$: C, 56.22; H, 6.21; N, 6.39; S, 14.63. Found: C, 56.46; H, 6.28; N, 6.31; S, 14.59.

EXAMPLE 13

[4S-[4α(R*),7α,10aβ]]-Octahydro-4-[(2-mercapto-4-methyl-1-oxopentyl)amino]-5-oxo-7H-pyrido[2,1-b][1,3]thiazepine-7-carboxylic acid a) (R)-2-Bromo-4-methylpentanoic acid Potassium bromide (9.5 g., 80 mmol) was added to a stirred solution of D-leucine (3.0 g., 23 mmol) in 2.5N sulfuric acid (47 ml) at room temperature. The reaction mixture was cooled to −10° C. and solid sodium nitrite (2.4 g., 34 mmol) was added portionwise, maintaining the temperature between −10° and −5° C. After addition was complete, the reaction was stirred for 1 hour and then warmed to room temperature and stirred for another hour.

The reaction mixture was then extracted twice with ether, the ether extracts were washed once with water, dried (magnesium sulfate), filtered and evaporated to give 2.7 g of crude title product.

b) (S)-2-(Acetylthio)-4-methylpentanoic acid, dicyclohexylamine salt

To a stirred slurry of potassium thioacetate (1.7 g, 15.0 mmol) in 50 ml of dry acetonitrile at room temperature under argon was added a solution of the product from part (a) (2.6 g., 13 mmol) in 17 ml of acetonitrile. The reaction was stirred 4 hours. The resulting slurry was filtered and evaporated. The residue was redissolved in ethyl ether, washed once with 5% potassium bisulfate solution and once with brine, dried (magnesium sulfate) and evaporated. The residue was dissolved in ether (64 ml) and treated with dicyclohexylamine (2.7 ml, 14 mmol). A white solid immediately began precipitating from the solution. The solution was filtered and the white solid collected to give 2.0 g of title product; m.p. 153°–158° C.; $[\alpha]_D$=−54.5° (c=0.61, chloroform).

c) [4S-[4α(R*),7α,10aβ]]-Octahydro-4-[[2-(acetylthio)-4-methyl-1-oxopentyl]amino]-5-oxo-7H-pyrido[2,1-b][1,3]thiazepine-7-carboxylic acid, methyl ester A stirred suspension of the product from part (b) (403.3 mg, 1.09 mmol) in ethyl acetate (5 ml) was washed three times with 5 ml portions of 5% potassium bisulfate solution. The organic extracts were combined, washed with brine, dried (sodium sulfate), filtered, concentrated and dried in vacuo for 30 minutes. The resulting oil (179.4 mg, 0.943 mmol) was dissolved in methylene chloride (2 ml) and stirred under nitrogen at 0° C. To this solution was added a solution of [4S-(4α,7α,10aβ)]-octahydro-4-amino-5-oxo-7H-pyrido[2,1-b][1,3]thiazepine-7-carboxylic acid, methyl ester [232.0 mg, 0.898 mmol., prepared as described in Example 3(c)] in methylene chloride (6 ml), then triethylamine (0.131 ml., 0.943 mmol), and finally benzotriazol-1-yloxytris(dimethylamino)phosphonium hexafluorophosphate (417.1 mg, 0.943 mmol.). The reaction was stirred at 0° C. for one hour and 3.5 hours at room temperature. After a total of 4.5 hours, the reaction was concentrated in vacuo and the residue was dissolved in ethyl acetate. The solution was washed once with a 5% solution of potassium bisulfate (20 ml), once with a saturated solution of sodium bicarbonate (20 ml), and once with brine. The organic layer was dried (magnesium sulfate), filtered and concentrated to a yellow foam. Purification by flash chromatography (silica gel, 230–400 mesh under 10–20 psi of nitrogen pressure) eluting with 2:3 ethyl acetate/hexane gave 209.4 mg. of title product as a clear oil.

d) [4S-[4α(R*),7α,10aβ]]-Octahydro-4-[(2-mercapto-4-methyl-1-oxopentyl)amino]-5-oxo-7H-pyrido[2,1-b][1,3]thiazepine-7-carboxylic acid A solution of the product from part (c) (209.4 mg, 0.486 mmol) in methanol (5 ml, deoxygenated via nitrogen bubbling) was cooled to 0° C. and treated with 1N sodium hydroxide (5 ml, deoxygenated via nitrogen bubbling). After stirring for one hour at 0° C. while purging continuously with nitrogen, the reaction was warmed to room temperature. After a total of 2.5 hours, the reaction was acidified to pH 1 with 5% potassium bisulfate and extracted with ethyl acetate. The organic layers were combined, washed with water, brine, dried (sodium sulfate), filtered, and concentrated in vacuo. Purification by flash chromatography (silica gel, 230–400 mesh under 10–20 psi of nitrogen) eluting with nitrogen sparged 6:0.01:3.99 ethyl acetate/acetic acid/hexane gave 142.0 mg of title product as a white solid. TLC (6:0.1:3.9 ethyl acetate/acetic acid/hexane) $R_f$=0.20. $[\alpha]_D$= −103.0° (c=0.43, chloroform).

HPLC: $t_R$=26.7 min.; YMC S-3 ODS (C-18) 6.0×150 mm; 0% to 100% B: A, 30 min. linear gradient and 10 min. hold, 1.5 ml/min; A=90% water:methanol+0.2% phosphoric acid, B=90% methanol:water+0.2% phosphoric acid; 220 nm.

Anal. calc'd for $C_{16}H_{26}O_4N_2S_2$•0.19 $C_4H_8O_2$•0.18 $C_7H_{16}$•0.9 $H_2O$: C, 50.87; H, 7.63; N, 6.58; S, 15.07. Found: C, 50.57; H, 7.20; N, 6.83; S, 14.75.

EXAMPLE 14

[4S-[4α(R*),7α,9aβ]]-Octahydro-4-[(2-mercapto-1-oxybutyl)amino]-5-oxopyrrolo[2,1-b][1,3]thiazepine-7-carboxylic acid a) (R)-2-Bromobutanoic acid

Potassium bromide (7.85 g, 65.94 mmol) was added to a solution of (R)-2-aminobutanoic acid (2.0 g, 19.40 mmol) in 2.5N sulfuric acid (25 ml) and cooled to 0° C. Sodium nitrite (2.06 g, 29.87 mmol) was added slowly in several portions. The temperature was kept at less than 2° C. during this addition. The reaction was stirred at 0° C. for one hour and at room temperature for 16 hours, then extracted with 3–50 ml portions of ethyl acetate. The combined ethyl acetate layers were washed with 2–50 ml portions of water, 1–50 ml portion of brine, dried (magnesium sulfate) and concentrated in vacuo to give 2.86 g of title product as a crude oil.

b) (S)-2-(Acetylthio)butanoic acid, dicyclohexylamine salt

To a slurry of 2.14 g (18.77 mmol) of potassium thioacetate in 15 ml of acetonitrile, stirred at room temperature, was added dropwise over 15 minutes a solution of (R)-2-bromobutanoic acid (2.83 g, 17.07 mmol) in 15 ml of acetonitrile. The reaction was stirred at room temperature for 16 hours then filtered. The filtrate was concentrated in vacuo and the resulting oil was dissolved in 30 ml of ethyl ether. The ether layer was washed with 2–20 ml portions of 5% potassium bisulfate, 2–20 ml portions of water, 2–20 ml portions of brine, dried (magnesium sulfate) and filtered. To the filtrate was added 3.4 ml (17.07 mmol) of dicyclohexylamine. After stirring at room temperature for 2 hours, the slurry was filtered to give 1.24 g of the dicyclohexylamine salt product. A second crop of 724 mg of dicyclohexylamine salt product was obtained from the filtrate.

c) [4S-[4α(R*),7α,9aβ]]-Octahydro-4-[[2-[(acetylthio)-1-oxobutyl]amino]-5-oxopyrrolo[2,1-b][1,3]thiazepine-7-carboxylic acid, methyl ester The dicyclohexylamine salt product from part (b) (227 mg, 0.66 mmol) was dissolved in 15 ml of ethyl acetate and washed with three 10 ml portions of potassium bisulfate, one 10 ml portion of brine, dried (magnesium sulfate), and concentrated in vacuo to give 108 mg of (S)-2-(acetylthio)butanoic acid as a clear oil.

To a solution of this free acid (108 mg, 0.66 mmol) in 5 ml of dry methylene chloride, cooled to 0° C., was added triethylamine (90 μl, 0.66 mmol), followed by [4S-(4α,7α,9aβ)]-4-amino-octahydro-5-oxopyrrolo[2,1-b][1,3]thiazepine-7-carboxylic acid, methyl ester, p-toluenesulfonic acid salt [250.0 mg, 0.66 mmol, prepared from the material described in Example 5(d)] and a second portion of triethylamine (90 μl, 0.66 mmol). The reaction was stirred at 0° C. for 20 minutes, then benzotriazol-1-yloxytris(dimethylamino)phosphonium hexafluorophosphate (292 mg, 0.66 mmol) was added in one portion. The reaction was stirred at 0° C. for one hour, refrigerated for 56 hours, then stirred at room temperature for 3 hours. The reaction mixture was then concentrated in vacuo, redissolved in 30 ml ethyl acetate and washed with 20 ml of 5% potassium bisulfate, 20 ml saturated sodium bicarbonate, 20 ml of brine, dried (magnesium sulfate), and concentrated in vacuo to give a crude oil. The crude oil was flash chromatographed (Merck silica gel, 25×100 mm, 2:3 ethyl acetate/hexane) to give 208 mg of title product as a white foam.

d) [4S-[4α(R*),7α,9aβ]]-Octahydro-4-[(2-mercapto-1-oxobutyl)amino]-5-oxopyrrolo[2,1-b][1,3]thiazepine-7-carboxylic acid A solution of the product from part (c) (225 mg, 0.559 mmol) in methanol (5 ml) was purged with argon for 30 minutes and cooled to 0° C. To this solution was added dropwise 5 ml of 1M sodium hydroxide, also purged with argon for 30 minutes and cooled to 0° C. The reaction was stirred at 0° C. for 3 hours with continuous argon purging, then acidified to pH 2 with 5% potassium bisulfate solution. The mixture was extracted with 3–40 ml portions of ethyl acetate, and the combined ethyl acetate layers were dried (magnesium sulfate), and concentrated in vacuo to give a crude foam. The crude product was flash chromatographed (Merck silica gel, 25×180 mm, 3% acetic acid/ethyl acetate) to give a white foam, which was dissolved in methylene chloride and triturated with hexane to give 176 mg of title product as a compact white foam; $[\alpha]_D$=−125.4° (c= 1.0, chloroform). TLC (methanol/methylene chloride 1:9) $R_f$=0.16.

HPLC: $t_R$=15.5 min. (97% total area, UV 220 nM); YMC S-3 ODS (C-18, 120A) 6×150 mm; 0% B:A-100% B:A, linear 25 minute gradient (A=90% water/methanol+0.2% phosphoric acid) B=90% methanol/water+0.2% phosphoric acid); flow rate=1.5 ml/min.

Anal. calc'd for $C_{13}H_{20}N_2S_2O_4$•0.8 $H_2O$•0.2 $C_6H_{14}$•0.1 $CH_2Cl_2$: C, 46.10; H, 6.66; N, 7.52; S, 17.21. Found: C, 46.00; H, 6.17; N, 7.52; S, 16.82.

EXAMPLE 15

[4S-[4α(R*),7α,9aβ]]-Octahydro-4-[(2-mercapto-1-oxopentyl)amino]-5-oxopyrrolo[2,1-b][1,3]thiazepine-7-carboxylic acid a) (R)-2-Bromopentanoic acid

Following the procedure of Example 14(a) but employing D-norvaline in place of (R)-2-aminobutanoic acid, (R)-2-bromopentanoic acid was obtained as a clear liquid.

b) (S)-2-(Acetylthio)pentanoic acid, dicyclohexylamine salt

Reacting (R)-2-bromopentanoic acid with potassium thioacetate in acetonitrile followed by treatment with dicyclohexylamine according to the procedure of Example 14(b), (S)-2-(acetylthio)pentanoic acid, dicyclohexylamine salt was obtained as a white solid.

c) [4S-[4α(R*),7α,9aβ]]-Octahydro-4-[[2-(acetylthio)-1-oxopentyl]amino]-5-oxopyrrolo[2,1-b][1,3]thiazepine-7-carboxylic acid, methyl ester Reacting the free acid of the dicyclohexylamine salt from part (b) with [4S-(4α,7α,9aβ)]-4-amino-octahydro-5- oxopyrrolo[2,1-b][1,3]thiazepine-7-carboxylic acid, methyl ester according to the procedure of Example 14(c), the title product was obtained as a white foam.

d) [4S-[4α(R*),7α,9aβ]]-Octahydro-4-[(3-mercapto-
1-oxopentyl)amino]-5-oxopyrrolo[-2,1-b][1,3]
thiazepine-7-carboxylic acid A solution of the product from part (c) in methanol was treated with 1M sodium hydroxide according to the procedure of Example 14(d) and gave the title product as a compact white foam; [α]$_D$=–122.8° (c=1.0, CDCl$_3$). TLC (methanol/methylene chloride 1:9) R$_f$=0.15. HPLC: t$_r$=20.5 min.; (97% total area, UV 220 nM); YMC S-3 ODS (C-18, 120A) 6×150 mm; 0% B:A-100% B: A, linear 25 minute gradient (A=90% water:methanol+0.2% phosphoric acid); B=90% methanol:water+0.2% phosphoric acid; flow rate= 1.5 ml/min.

Anal. calc'd for $C_{14}H_{22}N_2S_2O_4$•0.65 $H_2O$•0.20 $C_6H_{14}$: C, 48.63; H, 7.01; N, 7.46; S, 17.08. Found: C, 48.86; H, 6.70; N, 7.24; S, 16.74.

EXAMPLE 16

[4S-[4α(R*),7α,9aβ]]-Octahydro-4-[(2-mercapto-4,
4-dimethyl-1-oxopentyl)]amino]-5-oxopyrrolo[2,1-
b][1,3]thiazepine-7-carboxylic acid a) (R) 2-Bromo-4,4-dimethyloentanoic acid A solution of (R)-2-amino-4,4-dimethylpentanoic acid (950 mg, 6.55 mmol) in 2.5N aqueous sulfuric acid (13 ml, 33 mmol) was cooled to −5° C. and treated with potassium bromide (2.72 g, 22.9 mmol) in one portion. The colorless solution was treated with sodium nitrite (680 mg, 9.86 mmol) portionwise, keeping the temperature between 0° and 3° C. over a period of 25 minutes. The reaction mixture was stirred at 0° C. for one hour and at room temperature for 1.5 hours. The reaction mixture was poured into water (10 ml). The product was extracted with ether (60 ml), washed with water (20 ml) and brine (20 ml), dried (magnesium sulfate), and concentrated in vacuo to give the title product as a colorless liquid.

b) (S)-2-(Acetylthio)-4,4-dimethylpentanoic acid

A slurry of potassium thioacetate (750 mg, 6.58 mmol) and acetonitrile (10 ml, molecular sieves dried) was cooled to 0° C. and treated with a solution of (R)-2-bromo-4,4-dimethylpentanoic acid from part (a) in acetonitrile (2 ml) over 5 minutes. The reaction mixture was allowed to warm to room temperature and stirred for 2.5 hours. The slurry was filtered. The filtrate was concentrated in vacuo. The residue was diluted in ether (50 ml), washed with two portions of 5% aqueous sodium thiosulfate (50 ml) and brine (25 ml), dried (magnesium sulfate), and concentrated in vacuo. The pale yellow oil was purified by flash chromatography (Merck silica gel, 12×3 cm., 10% methanol/methylene chloride) affording 575 mg of title product as a pale yellow oil.

c) [4S-[4α(R*),7α,9aβ]]-Octahydro-4-[[2-
(acetylthio)-4,4-dimethyl-1-oxopentyl]amino]-5-
oxopyrrolo[2,1-b][1,3]thiazepine-7-carboxylic acid,
methyl ester A clear solution of the product from part (b) (148 mg, 0.72 mmol) in methylene chloride (5 ml, distilled from calcium hydride) was cooled to 0° C. and treated with a solution of [4S-(4α,7α,9aβ)]-4-amino-octahydro-5-oxopyrrolo[2,1-b] [1,3]thiazepine-7-carboxylic acid, methyl ester, p-toluenesulfonic acid salt [250.0 mg, 0.60 mmol, prepared from the material described in Example 5(d)] in methylene chloride (3 ml, distilled from calcium hydroxide), triethylamine (122 mg, 1.2 mmol), followed by benzotriazol-1-yloxytris(dimethylamino)phosphonium hexafluorophosphate (319 mg, 0.72 mmol). The reaction mixture was stirred at 0° C. for 24 hours and at room temperature for 5 hours. The crude reaction mixture was concentrated in vacuo. The residue was diluted in ethyl acetate (50 ml), washed with 5% aqueous potassium bisulfate (50 ml), 50% saturated aqueous sodium bicarbonate solution (50 ml), and brine (50 ml), dried (sodium sulfate) and concentrated in vacuo. The crude product was purified by flash chromatography (20 g, Merck silica gel, ethyl acetate) to afford 244 mg of the title product as a white foam.

d) [4S-[4α(R*),7α,9aβ]]-Octahydro-4-[(2-mercapto-
4,4-dimethyl-1-oxopentyl)amino]-5-oxopyrrolo[2,1-
b][1,3]thiazepine-7-carboxylic acid A clear solution of the product from part (c) (240 mg, 0.56 mmol) in methanol (2 ml, nitrogen sparged) was cooled to 0° C. and treated dropwise with 1N sodium hydroxide (2.27 ml, 2.24 mmol, argon sparged) with continuous sparging at 0° C. The mixture was allowed to stir at 0° C. for 3 hours and at room temperature for 3 hours. The mixture was acidified to pH of 1 with a solution of 5% aqueous potassium bisulfate (argon sparged). The product was extracted with methylene chloride (50 ml, nitrogen sparged), washed with brine, dried (sodium sulfate) and concentrated in vacuo. The crude product was recrystallized from methylene chloride/hexane to afford 75 mg of title product as a white solid; m.p. 124°–126° C.; [α]$_D$=−175° (c=0.25, methanol). TLC (acetic acid/methanol/methylene chloride 1:5:94) R$_f$=0.65.

HPLC: t$_R$ (YMC, S-3 ODS (C-18) 6.0×150 mm; 1.5 ml/min. linear gradient 0–100% B over 30 min., Buffer A=methanol/water/phosphoric acid (10:90:0.2), Buffer B=methanol/water/phosphoric acid (90:10:0.2))=24.4 min., 95% of total peak area at 254 nm.

Analysis calc'd. for $C_{16}H_{26}N_2O_4S_2$•0.13 $C_6H_{14}$: C, 52.24; H,7.28; N, 7.26; S, 16.62 Found: C, 51.97; H,7.26; N, 7.09; S, 16.23.

EXAMPLE 17

[4S-[4α(R*),7α,9aβ]]-Octahydro-4-[(2-mercapto-1-
oxopropyl)amino]-5-oxopyrrolo[2,1-b]1,3]
thiazepine-7-carboxylic acid a) (R)-2-Bromopropanoic acid Following the procedure of Example 14(a) but employing D-alanine in place of (R)-aminobutanoic acid, (R)-2-bromopropanoic acid was obtained as a light yellow oil.

b) (S)-2-(Acetylthio)propanoic acid

To a light green solution of potassium thioacetate (3.94 g, 34.5 mmol) in acetonitrile (150 ml) was added a solution of (R)-2-bromopropanoic acid (4.8 g, 31 mmol) in acetonitrile (12 ml) at room temperature under an argon atomosphere. The resulting white slurry was stirred at room temperature for 2 hours then filtered. The filtrate was concentrated in vacuo. The residue was diluted in ethyl acetate (100 ml), washed with a 10% aqueous solution of potassium bisulfate (50 ml) and brine, dried (sodium sulfate), and concentrated in vacuo. The crude product (4.61 g) was purified by flash chromatography (60 g - Merck silica gel, 1:45:54 acetic acid/ethyl acetate/hexane) to afford 3.7 g of the title product as a light yellow oil; $[\alpha]_D=-114°$ (c=0.50, methanol).

c) [4S-[4α(R*),7α,9aβ]]-Octahydro-4-[[2-(acetylthio)-1-oxopropyl]amino]-5-oxopyrrolo[2,1-b][1,3]thiazepine-7-carboxylic acid, methyl ester A clear solution of (S)-2-(acetylthio)propanoic acid (86 mg, 0.58 mmol) in methylene chloride (5 ml, distilled from calcium hydride) was cooled to 0° C. and treated with a solution [4S-(4α,7α,9aβ)]-4-amino-octahydro-5-oxopyrrolo[2,1-b][1,3]thiazepine-7-carboxylic acid, methyl ester, p-toluenesulfonic acid salt [200.0 mg, 0.48 mmol, prepared from the material described in Example 5(d)] in methylene chloride (5 ml, distilled from calcium hydride), triethylamine (98 mg, 0.97 mmol), followed by benzotriazol-1-yloxytris(dimethylamino)phosphonium hexafluorophosphate (255 mg, 0.58 mmol). The reaction mixture was stirred at 0° C. for 22 hours and at room temperature for 2 hours. The crude reaction mixture was concentrated in vacuo. The residue was diluted in ethyl acetate (100 ml), washed with 5% aqueous potassium bisulfate (30 ml), 50% saturated aqueous sodium bicarbonate solution, and brine, dried (sodium sulfate), and concentrated in vacuo. The crude product was purified by flash chromatography (40 g., Merck silica gel, ethyl acetate) to afford 180 mg of title product as a white solid; m.p. 143°–145° C.

d) [4S-[4α(R*),7α,9aβ]]-Octahydro-4-[(2-mercapto-1-oxopropyl)amino]-5-oxopyrrolo[2,1-b][1,3]thiazepine-7-carboxylic acid A clear solution of the product from part (c) (180 mg, 0.48 mmol) in methanol (2 ml) under an argon atmosphere was cooled to −10° C. and treated dropwise with argon sparged 1N sodium hydroxide (1.95 ml, 1.95 mmol), keeping the temperature below 0° C. The mixture was allowed to stir with argon sparging at 0° C. for 3 hours. The mixture was acidified to pH of 1 with a solution of 5% aqueous potassium bisulfate under an argon atmosphere. The product was extracted with nitrogen sparged ethyl acetate (100 ml), washed with brine, dried (sodium sulfate), and concentrated in vacuo. The crude product was purified by flash chromatography (40 g, Merck silica gel, 1:5:94 acetic acid/methanol/methylene chloride) to afford 154 mg of title product as a white solid; m.p. 150°–152° C.; $[\alpha]_D=-156°$ (C=0.50, methanol). TLC (1:5:94 acetic acid/methanol/methylene chloride) $R_f=0.28$.

HPLC: $t_R$ (YMC, S-3 ODS (C-18) 6.0×150 mm; 1.5 ml/min. linear gradient 0–100% B over 30 minutes. Buffer A=methanol/water/phosphoric acid (10:90:0.2), Buffer B=methanol/water/phosphoric acid (90:10:0.2))=14.69 min., more than 95% of total peak area at 254 mM.

Anal. calc'd. for $C_{12}H_{18}N_2O_4S_2 \cdot 0.75CH_3CO_2H$: C, 44.61; H, 5.82; N, 7.71; S, 17.64 Found: C, 44.76; H, 5.71; N, 7.81; S, 17.76.

EXAMPLE 18

[4S-[4α(R*),7α,9aβ]]-Octahydro-4-[3-cyclopropyl-2-mercapto-1-oxopropyl)amino]-5-oxopyrrolo[2,1-b][1,3]thiazepine-7-carboxylic acid a) (R)-2-[[(Phenylmethoxy)carbonyl]amino]-4-pentenoic acid A mixture of D-allylglycine (2.8 g, 24.3 mmol), 1M aqueous sodium hydroxide solution (25 ml), and tetrahydrofuran (10 ml, distilled from ketyl) was stirred at room temperature until homogeneous then cooled in an ice-bath. To the resulting rapidly stirred solution was added about 5 mL of 1.0M aqueous sodium hydroxide solution then dropwise about 1 g of benzyl chloroformate. This was repeated 4 additional times until a total of 28 mL of 1.0M aqueous sodium hydroxide solution and 4.80 g (95%, 27 mmol) of benzyl chloroformate were added. The reaction mixture was stirred for 15 minutes at 0° C. then 30 minutes at room temperature and then extracted with 50 mL of ether. The aqueous layer was acidified (pH=1.5) the by addition of 6N hydrochloric acid solution (about 10 mL) then extracted with three-50 mL portions of ether. The three ether extracts were combined, dried (magnesium sulfate) and concentrated in vacuo to afford 6.01 g of title product as a colorless oil.

b) (R)-2-[[(Phenylmethoxy)carbonyl]amino]-4-pentenoic acid, phenylmethyl ester

Cesium carbonate (4.28 g, 13.1 mmol) was added to a solution of the product from part (a) (5.96 g, 23.9 mmol) in anhydrous dimethylformamide (25 ml) at room temperature. The reaction mixture was stirred for 20 minutes then benzyl bromide (4.5 g, 26.3 mmol) was added rapidly (mildly exothermic). The mixture was stirred for 30 minutes then partitioned between 100 ml of water and 100 ml of ether. The organic layer was separated, washed with three-100 mL portions of water, 50 mL of brine, dried (magnesium sulfate) and concentrated in vacuo to give an oil. The crude material was purified by flash chromatography (Merck silica gel, 24×5.0 cm, 1:10 ethyl acetate/hexane then 1:4 ethyl acetate/hexane) to afford 6.13 g of title product as a colorless oil.

c) (R)-α-[[(Phenylmethoxy)carbonyl]amino]cyclopropanepropanoic acid, phenylmethyl ester Palladium(II)acetate (65 mg, 0.29 mmol) was added to a solution of the product from part (b) (5.78 g, 17.1 mmol) in anhydrous ether (60 ml) and stirred for 10 minutes. The resulting mixture was cooled to 0° C. was excess ethereal diazomethane (prepared from 12 g N-methyl-N'-nitro-N-nitrosoguanidine/120 ml ether) was added in portions over about 15 minutes. The reaction mixture was stirred for 15 minutes then quenched by addition of 1 mL of glacial acetic acid. The solution was transferred to a separatory funnel, washed with 100 mL of saturated aqueous sodium bicarbonate solution, 50 mL of brine, dried (magnesium sulfate) and concentrated in vacuo to give a yellow oil. The crude material was purified by flash chromatography (Merck silica gel, 20×5.0 cm, 1:4 ethyl acetate/hexane) to afford 5.74 g of title product as a colorless oil.

d) (R)-(α-Amino)cyclopropanepropanoic acid

Palladium on carbon catalyst (10%, 1.14 g) was added to a solution of the product from part (c) (5.71 g, 16.2 mmol) in methanol (75 ml) and stirred under an atmosphere of hydrogen (balloon) at room temperature for 48 hours. The reaction mixture was filtered to remove the catalyst and the catalyst was rinsed with warm water. The filtrate was then passed through a 0.4 µM polycarbonate membrane filter. The filtrate was concentrated in vacuo to give 2.03 g of title product as a white solid.

e) (S)-α-(Acetylthio)cyclopropanepropanoic acid

A mixture of the product from part (d) (2.00 g, 15.5 mmol) in 2.5N aqueous sulfuric acid (30 ml) was stirred at room temperature until homogeneous and then cooled to −5° C. Potassium bromide (6.50 g, 54.6 mmol) was added to this solution in one portion. The mixture was stirred until homgeneous. Sodium nitrite (1.60 g, 23.2 mmol) was then added in small portions over about 25 minutes, maintaining the reaction temperature below 0° C. The reaction mixture was stirred for an additional 1 hour at 0° C. then at room temperature for 1.5 hours. The resulting mixture was diluted with 30 ml of water and extracted with three-30 mL portions of ether. The combined ether extracts were washed with 25 mL of brine, dried (magnesium sulfate) and concentrated in vacuo to give 2.82 g of crude (R)-(α-bromo) cyclopropanepropanoic acid as a pale yellow oil.

A solution of this crude (R)-(α-bromo) cyclopropanepropanoic acid was added in acetonitrile (10 ml) over 5 minutes to a stirred slurry of potassium thioacetate (1.83 g, 16.1 mmol) in acetonitrile (20 ml) while cooling in an ice-bath. The reaction mixture was stirred at 0° C. for 1 hour then at room temperature for 16 hours. The reaction mixture was filtered and the filtrate concentrated in vacuo to give an oil. The oil was partitioned between 50 mL of ether and 50 mL of 5% aqueous sodium thiosulfate solution. The organic layer was separated, washed with 25 mL of brine, dried (magnesium sulfate) and concentrated in vacuo to give a yellow oil. The crude material was purified by flash chromatography (Merck silica gel, 12×5.0 cm, 1:19 methanol/methylene chloride) to afford 1.52 g of title product as a yellow oil.

f) [4S-[4α(R*),7α,9aβ]]-Octahydro-4-[[2-(acetylthio)-3-cyclopropyl-1-oxopropyl]amino]-5-oxopyrrolo[2,1-b][1,3]thiazepine-7-carboxylic acid, methyl ester Benzotriazol-1-yloxytris(dimethylamino)phosphonium hexafluorophosphate (292 mg, 0.66 mmol) was added in one portion to a mixture of [4S-(4α,7α,9aβ)]-octahydro-4-amino-5-oxopyrrolo[2,1-b][1,3]thiazepine-7-carboxylic acid, methyl ester, p-toluenesulfonic acid salt [250 mg, 0.60 mmol, prepared from the material described in Example 5(d)] in methylene chloride (3 ml, distilled from calcium hydride), triethylamine (121 mg, 1.20 mmol), and the product from part (e) (122 mg, 0.65 mmol) in methylene chloride (3 ml, distilled from calcium hydride). The reaction mixture was stirred for 0° C. for 1 hour then at room temperature for 1.5 hours. The resulting mixture was partitioned between 20 ml of ethyl acetate and 20 ml of 1M aqueous potassium bisulfate solution. The organic layer was separated, washed with 20 ml of 5% aqueous sodium bicarbonate solution, 20 ml of brine, dried (magnesium sulfate) and concentrated in vacuo to give an oil. The crude material was purified by flash chromatography (Merck silica gel, 12×3.0 cm, 1:1 ethyl acetate/hexane) to afford 191 mg of title product as a solid white foam.

g) [4S-[4α(R*),7α,9aβ]]-Octahydro-4-[(3-cyclopropyl-2-mercapto-1-oxopropyl)amino]-5-oxopyrrolo[2,1-b][1,3]thiazepine-7-carboxylic acid A solution of the product from part (f) (185 mg, 0.45 mmol) in methanol (3 ml) was sparged with argon for 10 minutes at 0° C. and then 1M aqueous sodium hydroxide solution (3 ml, freshly sparged with argon for 10 minutes) was added. The reaction mixture was stirred for 2.5 hours at room temperature with continuous argon sparge then acidified by addition of 20 ml of 1M potassium bisulfate solution and extracted with 20 ml of ethyl acetate. The organic extract was washed with 20 ml of brine, dried (sodium sulfate) and concentrated in vacuo to give a gum. The gum was rinsed with anhydrous ether then concentrated under oil pump vacuum to afford 121 mg of the title product as a white foam; [α]$_D$=-103° (c=0.23, methanol). TLC (1:10:90 acetic acid/methanol/methylene chloride) R$_f$=0.46.

HPLC: t$_R$ (YMC S-3 ODS 6.0×150 mm; 1.5 mL/min, linear gradient 0–100% B over 30 minutes, Buffer A=methanol/water/phosphoric acid (10:90:0.2), Buffer B=methanol/water/phosphoric acid (90:10:0.2))=20.7 minutes greater than 97% of total peak area at 254 nm.

Anal. calc'd for $C_{15}H_{22}N_2O_4S_2 \cdot 0.20\ H_2O$: C, 49.77; H, 6.23; N, 7.74; S, 17.71 Found C, 50.01; H, 6.27; N, 7.50; S, 17.40.

EXAMPLE 19

[4S-(4α,7α,9aβ)]-Octahydro-4-[[(1-mercaptocyclopentyl)carbonyl]amino]-5-oxopyrrolo[2,1-b][1,3]thiazepine-7-carboxylic acid a) 1-Mercaptocyclopentanecarboxylic acid A solution of lithium diisopropylamide was prepared under nitrogen from diisopropylamine (5.4 ml, 38.5 mmol) and n-butyllithium (2.5M in hexanes, 15.4 ml, 38.5 mmol) in tetrahydrofuran (17.6 ml), maintaining the temperature between -3° C. to 0°. After stirring for 15 minutes, cyclopentanecarboxylic acid (2.0 g, 17.5 mmol) was added in tetrahydrofuran (2 ml) at 0° C. to 3° C. over 25 minutes. After 15 minutes at 0° C., the bath was removed and the reaction was stirred 15 minutes more, causing the temperature to rise to 15° C. The milky white solution was cooled to -78° C. and sulfur (S$_8$, 618.0 mg, 19.3 mmol) was added as a solid, maintaining the temperature at -78° C. The reaction was allowed to warm to room temperature in situ. After 70 hours, the reaction was cooled to 0° C., quenched with water (pH 8–9) and quickly acidified to pH 1 with 6 N hydrochloric acid. The aqueous solution was extracted with ethyl acetate (3×30 ml), washed with brine, dried (magnesium sulfate), filtered and concentrated to give 2.62 g of title product as a yellow oil.

b) 1-(Acetylthio)cyclopentanecarboxylic acid

To a solution of the product from part (a) (1.44 g, 9.89 mmol) in a nitrogen sparged solution of 1N sodium hydroxide (20 ml, 19.7 mmol) at 0° C. was added acetic anhydride (0.93 ml, 9.89 mmol). Tetrahydrofuran (13 ml) was added in order to solubilize the oil which formed. After stirring one hour at 0° C. (pH 7), the reaction was warmed to room temperature and additional acetic anhydride (0.47 ml, 4.9 mmol) was added, as well as solid potassium carbonate (2.04 g, 14.8 mmol) to pH 10 and tetrahydrofuran (4 ml). After stirring overnight at room temperature, the reaction mixture was acidified to pH 1 with 1N hydrochloric acid and extracted with ethyl acetate. The ethyl acetate extracts were combined, washed with brine, dried (magnesium sulfate) filtered and concentrated in vacuo to give a yellow solid (1.61 g). The solid was recrystallized twice from ethyl acetate/hexanes to give 614 mg of title product as a light brown solid; m.p. 119.5°–121.5° C.

c) [4S-(4α,7α,9aβ)]-Octahydro-4-[[1-[(acetylthio) cyclopentyl]carbonyl]amino]-5-oxopyrrolo[2,1-b][1,3]thiazepine-7-carboxylic acid, methyl ester To a solution of the product from part (b) (94.5, 0.502 mmol) in methylene chloride (3.6 ml) at 0° C. under nitrogen, was added triethylamine (70 µl, 0.502 mmol) followed by [4S-(4α,7α,9aβ)]-4-amino-octahydro-5-oxopyrrolo[2,1-b][1,3]thiazepine-7-carboxylic acid, methyl ester, p-toluenesulfonic acid salt [prepared from the material described in Example 5(d), 198.9 mg, 0.478 mmol] in one portion, followed by triethylamine (66.6 µl, 0.478 mmol). The reaction was stirred for 5 minutes at 0° C. Benzotriazol-1-yloxytris(dimethylamino)phosphonium hexafluorophosphate (222.0 mg, 0.502 mmol) was then added as a solid. The reaction was stirred at 0° C. for one hour and then at room temperature for 2.25 hours. The reaction was concentrated in vacuo and the residue partitioned between ethyl acetate and 5% potassium bisulfate (20 ml). The organic layer was washed with half saturated sodium bicarbonate and brine, dried (magnesium sulfate), filtered and concentrated to a clear oil. Purification by flash chromatography eluting with 11:9 ethyl acetate/hexane gave 169.3 mg. of title product as a clear oil.

d) [4S-(4α,7α,9aβ)]-Octahydro-4-[[(1-mercaptocyclopentyl)carbonyl]amino]-5-oxopyrrolo[2,1-b][1,3]thiazepine-7-carboxylic acid A solution of the product from part (c) (167.3 mg., 0.404 mmol) in methanol (4 ml, deoxygenated via nitrogen bubbling) was cooled to 0° C. and treated with 1N sodium hydroxide (4 ml, deoxygenated via nitrogen bubbling). After stirring for 1.5 hours at 0° C. while purging continuously with nitrogen, the reaction was warmed to room temperature. After a total of three hours, the reaction was acidified to pH 1 with 5% potassium bisulfate and extracted with ethyl acetate. The organic layers were combined, washed with water (20 ml), brine, dried (sodium sulfate), filtered, concentrated in vacuo and re-evaporated from hexanes to give a white solid. The compound was dissolved in dioxane (anhydrous) and lyophillized to give 110 mg, of title product as a white solid; $[\alpha]_D=-106.5°$ (c=0.68, chloroform). TLC (7:2.9:0.1, ethyl acetate/hexane/acetic acid) $R_f=0.12$.

HPLC: $t_R=21.5$ min; YMC S-3 ODS (C-18) 6.0×150 mm; 0% to 100% B: A, 30 minutes linear gradient and 10 minutes hold, 1.5 ml/min.; A=90% water/10% methanol+0.2% phosphoric acid, B=90% methanol/10% water+0.2% phosphoric acid; 220 nm.

Anal. calc'd for $C_{15}H_{22}N_2O_4S_2 \cdot 0.15$ $C_4H_8O_2 \cdot 0.7$ $H_2O \cdot 0.08 C_6H_{14}$: C, 49.37; H, 6.63; N, 7.16; S, 16.39 Found: C, 49.03; H, 6.37; N, 7.21; S, 16.65.

EXAMPLE 20

[4S-(4α,7α,10aβ)]-4-[(2-Carboxy-1-oxo-3-phenylpropyl)amino]octahydro-5-oxo-7H-pyrido[2,1-b][1,3]thiazepine-7-carboxylic acid a) 3-(Phenylmethyl)propanedioic acid, monoethyl ester 3-(Phenylmethyl)propanedioic acid, diethyl ester (2.5 g, 10 mmol) in 10 ml of tetrahydrofuran was stirred overnight with 10 ml of 1N lithium hydroxide. The reaction mixture was acidified with 11 ml of 1N hydrochloric acid and extracted with two 50 ml portions of ethyl acetate. The ethyl acetate extracts were washed with brine, dried (sodium sulfate), and concentrated in vacuo. The concentrate was chromatographed through silica gel (80 g) using a 5% methanol:chloroform solvent system. The appropriate fractions were combined and concentrated to yield 1.23 g of title product.

b) [4S-(4α,7α,10aβ)]-4-[[2-(Ethoxycarbonyl)-1-oxo-3-phenylpropyl]amino]octahydro-5-oxo-7H-pyrido[2,1-b][1,3]thiazepine-7-carboxylic acid, methyl ester The product from part (a) (0.222 g, 1 mmol) and [4S-(4α,7α,10aβ)]-octahydro-4-amino-5-oxo-7H-pyrido[2,1-b][1,3]thiazepine-7-carboxylic acid, methyl ester [0.258 g., 1 mmol, prepared as described in Example 3(c)] were dissolved in methylene chloride (5 ml) and cooled to 0° C. Triethylamine (0.14 ml, 1 mmol) was added and the reaction mixture was stirred for one hour. Benzotriazol-1-yloxytris (dimethylamino)phosphonium hexafluorophosphate (0.442 g, 1 mmol) was added and the solution was stirred at 0° C. for 1 hour and at room temperature for 2.5 hours. The reaction mixture was diluted with 50 ml of methylene chloride and washed with water, 10% sodium bisulfate, saturated aqueous sodium bicarbonate, dried (sodium sulfate), filtered and concentrated in vacuo. The residue was chromatogaphed through silica gel using 30% ethyl acetate in hexanes. The appropriate fractions were combined and concentrated in vacuo to yield 0.22 g of title product.

c) [4S-(4α,7α,10aβ)]-4-[(2-Carboxy-1-oxo-3-phenylpropyl)amino]octahydro-5-oxo-7H-pyrido[2,1-b][1,3]thiazepine-7-carboxylic acid The product from part (b) (0.22 g, 0.476 mmol) was stirred with 1N lithium hydroxide (5 ml) in tetrahydrofuran (5 ml) at room temperature for 3 hours. The reaction mixture was acidified to pH 2 with 1N hydrochloric acid and concentrated in vacuo. The residue was dissolved in ethyl acetate and washed with water, brine, dried (sodium sulfate), and concentrated in vacuo to 3 ml at which point product crystallized. After standing at 0° C. overnight, the solid was filtered and dried to yield 0.16 g of title product as a white solid; m.p. 159°–162° C.; $[\alpha]_D=-84.92°$ (c=0.7, methanol). TLC (chloroform:methanol, 9:1) $R_f=0.23$, 0.28.

HPLC: $t_R=16.15$, 16.35 min.; (UV 254 nm); YMC S-3 ODS (C-18) 6.0×150 mm, 3µ end capped column, linear gradient of 50–90% aqueous methanol containing 0.2% phosphoric acid, 20 min., 1.5 ml/min. (44.9%, 55.1% isomer mixture).

Anal. calc'd for $C_{20}H_{24}N_2SO_6 \cdot 0.1$ $H_2O$: C, 56.89; H, 5.78; N, 6.66; S, 7.59 Found: C, 56.98; H, 5.68; N, 6.58; S, 7.15.

EXAMPLE 21

[4S-[4α(R*),7α,10aβ]]-Octahydro-4-[(2-mercapto-1-oxo-3-phenylpropyl)amino]-5-oxo[1,4]oxazino[3,4-b][1,3]thiazepine-7-carboxylic acid a) O-(2,2-Dimethoxyethyl)-N-[N-[(phenylmethoxy)carbonyl]-L-homoseryl]-L-serine, methyl ester A solution of N-[O-[(1,1-dimethylethyl)dimethylsilyl]-N-[(phenylmethoxy)carbonyl]-L-homoseryl]-O-(2,2-dimethoxyethyl)-L-serine, methyl ester [5.56 g, 10 mmol, prepared as described in Example 10(h)] in methanol (65 ml) was cooled to 0° C. (ice salt bath), treated with p-toluenesulfonic acid monohydrate (386 mg, 2.0 mmol) and stirred at 0° C. for 1.5 hours. The reaction was quenched with sodium bicarbonate solution (198 mg. in 20 ml water), stirred for 5 minutes then evaporated to remove the methanol. The aqueous phase was extracted with ethyl acetate (2×200 ml) and the combined organic extract was washed with water (110 ml), 5% sodium bicarbonate (80 ml) and brine (80 ml), dried (anhydrous sodium sulfate), filtered, evaporated to dryness and dried in vacuo. The crude product was chromatographed on silica gel column (Merck), eluting the column with ethyl acetate:hexane (2:1) and ethyl acetate:methanol (98:2) to give 3.975 g of title product as a syrup. TLC (ethyl acetate:hexane, 4:1) $R_f=0.17$.

b) O-(2,2-Dimethyloxyethyl)-N-[O-(methylsulfonyl)-N-[(phenylmethoxy)carbonyl]-L-homoseryl]-L-serine, methyl ester A solution of the product from part (a) (3.975 g, 8.98 mmol) in dry methylene chloride (52 ml) was cooled to −15°

C., treated with triethylamine (1.82 ml, 13.1 mmoles) and methanesulfonyl chloride (0.82 ml, 10.6 mmoles) and stirred at −15° C. for 30 minutes. The reaction mixture was quenched with 25% ammonium chloride (19 ml), warmed to room temperature and diluted with ethyl acetate (750 ml). The organic phase was washed with 5% potassium bisulfate (100 ml), 50% saturated brine (100 ml) and saturated brine (100 ml), dried (anhydrous sodium sulfate), filtered, evaporated to dryness and dried in vacuo to give 4.9 g of title product as a waxy solid. TLC (ethyl acetate:hexane, 4:1) $R_f$=0.32.

c) N-[S-Acetyl-N-[(phenylmethoxy)carbonyl]-L-homocysteinyl]-O-(2,2-dimethoxyethyl)-L-serine, methyl ester Cesium carbonate (5.56 g, 17.04 mmoles) was added to a solution of thiolacetic acid (2.6 ml) in dry methanol (40 ml), stirred for 10 minutes then evaporated to dryness. The resulting solid was triturated with acetone (7×8 ml) and the off-white solids obtained were dried in vacuo to give 4.39 g cesium thiolacetic acid.

A suspension of cesium thiolacetic acid (2.43 g, 1.3 eq.) in dry dimethylformamide (8.0 ml) was treated with a solution of the product from part (b) (4.9 g, 8.98 mmol) in dry dimethylformamide (24 ml) and stirred for 16 hours at room temperature under argon. The mixture was diluted with ethyl acetate (1.0 L), washed successively with 5% sodium bicarbonate (2×150 ml), water (2×150 ml) and brine (150 ml), dried (anhydrous sodium sulfate), filtered, evaporated to dryness and dried in vacuo. The crude product was chromatographed on a silica gel column (Merck), eluting the column with ethyl acetate:hexane mixtures (1:1; 2:1) to give 3.93 g of the title product as a waxy solid. TLC (ethyl acetate:hexane, 4:1) $R_f$=0.63.

d) O-(2,2-Dimethoxyethyl)-N-[N-[(phenylmethoxy)carbonyl]-L-homocysteinyl]-L-serine, methyl ester A solution of the product from part (c) (200 mg, 0.49 mmol) in methanol (8.0 ml) was purged with argon for 30 minutes, cooled to 0° C. (ice-salt bath) and treated with 25% sodium methoxide in methanol (0.11 ml, 0.5 mmol), maintaining the bubbling of argon throughout the addition and length of the reaction. After 5 minutes at 0° C., the mixture was quenched with 25% ammonium chloride (2.3 ml) and partitioned between ethyl acetate (2×12 ml) and water (2.3 ml). The combined organic extracts were washed with 25% ammonium chloride (4.6 ml) and brine (4.6 ml), dried (anhydrous sodium sulfate), filtered, evaporated to dryness and dried in vacuo to give 183.2 mg of title product as a white solid. TLC (ethyl acetate:hexane, 4:1) $R_f$=0.62.

e) [4S-(4α,7α,10aβ)]-Octahydro-5-oxo-4-[[(phenylmethoxy)carbonyl]amino][1,4]oxazino[3,4-b][1,3]thiazepine-7-carboxylic acid A solution of the product from part (d) (50 mg, 0.11 mmol) in dry methylene chloride (2.0 ml) was treated with Amberlyst® 15 (H⁺ form; 13 mg), stirred for 3 days at room temperature under argon, treated with more Amberlyst® 15 (13 mg) and stirred for another 3 days. The solution was decanted and chromatographed on silica gel column (Merck), eluting the column with ethyl acetate:hexane mixtures (1:3; 1:1) to give 21.1 mg of title product as a syrup. TLC (ethyl acetate:hexane, 4:1) $R_f$=0.70.

f) [4S-(4α,7α,10aβ)]-Octahydro-4-amino-5-oxo[1,4]oxazino[3,4-b][1,3]thiazepine-7-carboxylic acid, methyl ester A solution of the product from part (e) (421 mg, 1.01 mmoles) in dry methylene chloride (25 ml) was treated with trimethylsilyl iodide (0.72 ml, 5.06 mmoles) and stirred at room temperature under argon for 1.75 hours. The mixture was evaporated to dryness and the syrup obtained was partitioned between ethyl ether (50 ml) and 0.2N hydrochloric acid (2×25 ml). The aqueous phase was brought to pH 10 with saturated sodium bicarbonate (25 ml), treated with solid sodium chloride (2.0 g) and extracted with methylene chloride (3×75 ml) to give 219 mg of title product as a syrup. A second treatment of the aqueous phase with sodium chloride (2.0 g) and reextraction with methylene chloride (2× 100 ml) gave an additional 37 mg of title product. TLC (methylene chloride:methanol, 9:1) $R_f$=0.23.

g) [4S-[4α(R*)7α,10aβ]]-Octahydro-4-[[2-(acetylthio)-1-oxo-3-phenylpropyl]amino]-5-oxo[1,4]oxazino[3,4-b][1,3]thiazepine-7-carboxylic acid, methyl ester (S)-2-(Acetylthio)benzenepropanoic acid, dicyclohexylamine salt (516 mg, 1.32 mmol, 1.2 eq.) was suspended in ethyl acetate (42 ml), washed with 5% potassium bisulfate (5×6.0 ml) and brine (6.0 ml), dried (anhydrous magnesium sulfate), filtered, evaporated to dryness and dried in vacuo.

The free acid was dissolved in dry methylene chloride (9.5 ml), cooled to 0° C. (ice-salt bath) and treated sequentially with a solution of the product from part (f) (285.5 mg, 1.09 mmol) in dry methylene chloride (4.2 ml), triethylamine (0.14 ml, 1.15 mmol) and benzotriazol-1-yloxytris(dimethylamino)phosphonium hexafluorophosphate (484 mg, 1.09 mmol). The reaction mixture was stirred at room temperature for 1.0 hour and at room temperature for 2.0 hours under argon, then stripped to dryness. The residual syrup was dissolved in ethyl acetate (40 ml), washed with 0.5N hydrochloric acid (2×6.6 ml), water (6.6 ml) and brine (6.6 ml), dried (anhydrous sodium sulfate), filtered, evaporated to dryness and dried in vacuo. The crude product was chromatographed on silica gel column (Merck), eluting with ethyl acetate:hexane mixtures (1:2; 1:1) to give 382.9 mg of title product as a syrup. TLC (ethyl acetate:hexane, 1:1) $R_f$=0.28.

h) [4S-[4α(R*),7α,10aβ]]-Octahydro-4-[(2-mercapto-1-oxo-3-phenylpropyl)amino]-5-oxo[1,4]oxazino[3,4-b][1,3]thiazepine-7-carboxylic acid A solution of the product from part (g) (382.9 mg, 0.82 mmol) in methanol (9.0 ml) was purged with argon for 30 minutes, cooled to 0° C. (ice-salt bath) then treated with 1.0 N sodium hydroxide (3.32 ml, 4.0 eq; previously purged with argon for 30 minutes), maintaining the bubbling of argon throughout the addition and length of the reaction. The reaction mixture was stirred at 0° C. for 5.0 hours and at room temperature for 1.0 hour, brought to pH 2.0 with 5% potassium bisulfate (14.5 ml), warmed to room temperature and extracted with ethyl acetate (2×50 ml). The combined organic extracts were washed with brine (10 ml), dried (anhydrous sodium sulfate), filtered, evaporated to dryness and dried in vacuo. The syrup obtained was evaporated twice from hexane (25 ml) and the solid foam obtained was chromatographed on a silica gel column (Merck), eluting the column with toluene:acetic acid mixtures (100:1; 50:1; 20:1) to give 212 mg of title product as a solid; m.p. 224°–226° C.; $[\alpha]_D$=−50.2° (c=0.45, methanol). TLC (toluene:acetic acid, 5:1) $R_f$=0.28.

HPLC: $t_{R}$=5.37 min. (UV 220 nm) (98.9%); YMS S-3 ODS (C-18) 6×150 mm; 60% (10% water–90% methanol–0.2% phosphoric acid)/40% (90% water–10% methanol–0.2% phosphoric acid), isocratic.

Anal. calc'd for $C_{18}H_{22}N_2O_5S_2 \cdot 0.14\ H_2O$: C, 52.34; H, 5.44; N, 6.78; S, 15.53 Found: C, 52.58; H, 5.57; N, 6.44; S, 15.16.

EXAMPLE 22

[4S-[4α(R*),7α,10aβ]]-Octahydro-4-[(2-mercapto-1-oxo-3-phenylpropyl)amino]-5-oxo-7H-pyrido[2,1-b][1,3]thiazeoine-7-carboxylic acid The product of Examples 3 and 11 was also prepared as follows:

a) [4S-(4α,7α,10aβ)]-Octahydro-4-amino-5-oxo-7H-pyrido[2,1-b][1,3]thiazepine-7-carboxylic acid, methyl ester, p-toluenesulfonic acid salt

[4S-(4α,7α,10aβ)]-Octahydro-4-amino-5-oxo-7H-pyrido[2,1-b][1,3]thiazepine-7-carboxylic acid, methyl ester (6.11 g) was dissolved in ethyl acetate (about 100 ml) and treated with a solution of p-toluenesulfonic acid monohydrate (4.52 g) in methanol (3 ml) and ethyl acetate (20 ml). A precipitate formed immediately. The mixture was diluted with additional ethyl acetate and the solid was collected by filtration. The solid was washed with ethyl ether and dried in vacuo to give 7.908 g of the title product as a pale yellow solid in 98% purity; m.p. 179°–181° C. (decomp.).

b) [4S-[4α(R*),7α,10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl ester A slurry of the product from part (a) (636 mg, 1.48 mmol) in methylene chloride (5 ml) and dimethylformamide (1 ml) was treated with N-methylmorpholine (163 µl, 150 mg, 1.48 mmol) followed by 1-hydroxy-7-azabenzotriazole (208 mg, 1.52 mmol). The bright yellow solution was then treated with (S)-2-(acetylthio)benzenepropanoic acid (333 mg, 1.48 mmol) in methylene chloride (5 ml) and cooled in an ice-bath. Ethyl-3-(dimethylamino)propyl carbodiimide, hydrochloride salt (2.88 mg, 1.50 mmol) was added and the mixture was stirred at 0° C. for 1 hour and at room temperature for 1.5 hours. The solvent was removed by rotary evaporation and the residue was partitioned between ethyl acetate and 0.5N hydrochloric acid, The ethyl acetate extract was washed successively with water (twice), 50% saturated sodium bicarbonate, and brine, then dried (sodium sulfate), filtered, and stripped to give 651.2 mg of title product as a white foam.

c) [4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid A solution of the methyl ester product from part (b) in deoxygenated methanol was treated with 1N sodium hydroxide according to the procedure of Example 3(d) to afford the title product.

EXAMPLE 23

[4S-[4α(R*),7α,10aβ]]-Octahydro-4-[(2-mercapto-1-oxo-3-phenylpropyl)amino]-5-oxo-7H-pyrido [2,1-b][1,3]thiazepine-7-carboxylic acid The product of Examples 3, 11 and 22 was also prepared as follows:

a) N-[(Phenylmethoxy)carbonyl]-L-methionine

In a 2 L flask equipped with a mechanical stirrer and internal thermometer, sodium hydroxide (61.65 g, 1.541 mol) was dissolved in distilled water (1000 ml). To this solution, L-methionine (100.0 g, 0.670 mol) was added at room temperature. The solution was cooled in an ice bath (internal temperature 3° C.) and benzyl chloroformate (110 ml, 0.737 mol) was added over 10 minutes. After a 15 minute induction period, the internal temperature rose from 3° C. to 12° C. over 30 minutes and then dropped to 0° C. over 15 minutes. The reaction was stirred at 0° C. for 2 hours, during which time the initially cloudy reaction mixture became homogeneous. The ice bath was removed, and the reaction was allowed to warm to room temperature over 1 hour. The reaction mixture was transferred into a separatory funnel and washed with hexane (2×300 ml). The aqueous layer was acidified with 6N hydrochloric acid to pH 5 and diluted with ethyl acetate (600 ml). The mixture was further acidified to pH 2. The organic layer was separated, and the aqueous layer was extracted with ethyl acetate (3×600 ml). The organic extracts were combined and washed with brine (750 ml), dried (magnesium sulfate), filtered and concentrated in vacuo to produce a light yellow oil. The crude product (oil) was dissolved in toluene (1500 ml), and the solution was concentrated to half of its volume. A second portion of toluene (750 ml) was added, and concentrated again such that 630 ml of toluene remained. This solution was stored at 5° C. overnight, during which time some of the product crystallized from solution. The solid was redissolved by warming to room temperature. Toluene (134 ml) was then added (a few seed crystals remained). With mechanical stirring, heptane (500 ml) was added in 30 ml portions at 10 minute intervals (approximately 3 hours total addition time). At this point, the product started to crystallize from solution. An additional portion of heptane (1020 ml) was added over 1.5 hours, and the resulting slurry was stirred for 2 hours. The product was collected by vacuum filtration, washed with 1:2 toluene:heptane (3×150 ml) and heptane (3×500 ml) and air-dried to give 158.6 g of title product as a white solid; m.p. 66° C.; $[α]_D = -1.5°$ (c=1, 95% ethanol). TLC (ethanol:water, 3:1) $R_f = 0.78$.

Anal. calc'd for $C_{13}H_{17}NO_4S$: C, 55.11; H, 6.05; N, 4.94 Found: C, 54.96; H, 6.20; N, 4.83.

b) N-[(Phenylmethoxy)carbonyl]-L-methionine, methyl ester

In a 3 L flask equipped with a mechanical stirrer and an argon inlet, the product from part (a) (100.0 g, 0.353 mol) was dissolved in methanol (2 L), and p-toluenesulfonic acid monohydrate (6.71 g, 0.035 mol) was added. The reaction mixture was stirred under argon for 21 hours. Triethylamine (4.9 ml, 0.035 mol) was added, and the reaction mixture was stirred for an additional 15 minutes. The reaction mixture was concentrated in vacuo to a pale yellow oil. The oil was dissolved in ethyl acetate (900 ml), and the solution was washed with 1N hydrochloric acid (740 ml), saturated sodium bicarbonate (2×740 ml) and brine (740 ml). The organic layer was dried (magnesium sulfate), filtered and concentrated in vacuo to a light yellow oil. The oil was concentrated from hexane (2×100 ml) to obtain 98.22 g of title product as a white solid.

c) N-[(Phenylmethoxy)carbonyl]-L-methionine, sulfoxide, methyl ester

In a 3 L flask equipped with mechanical stirrer, the product from part (b) (97.95 g, 0.329 mol) was dissolved in methanol (1675 ml) and distilled water (215 ml). The solution was cooled in an ice bath, and sodium bicarbonate (28.5 g, 0.339 mol) was added. N-Chlorosuccinimide (44.0 g, 0.329 mol) was added in small portions over 25 minutes so that the internal temperature did not exceed 7° C. The mixture was stirred in an ice bath for 1 hour and then was allowed to warm to room temperature over 1 hour. The mixture was concentrated in vacuo by about 75% to remove the methanol, diluted with ethyl acetate (1000 ml) and washed with brine (500 ml). The brine layer was back-extracted with ethyl acetate (2×200 ml). The organic extracts were combined, dried (magnesium sulfate), filtered, and concentrated in vacuo to a clear, viscous oil. The oil was concentrated from toluene (3×100 ml) and residual solvents were removed under high vacuum to produce crude title product as a clear oil, which solidified to a white solid (131.4 g). The crude product contained 12 weight percent succinimide and 9 weight percent toluene by NMR. The product was a mixture of sulfoxide diastereomers.

d) S-[(Acetyloxy)methyl]-N-[(phenylmethoxy)carbonyl]-L-homocysteine, methyl ester To a 1 liter flask containing the product from part (c) (102.8 g corrected weight, 0.328 mol) was added toluene (480 ml), sodium acetate (32.3 g, 0.394 mol) and acetic anhydride (186 ml, 1.970 mol). The resulting mixture was refluxed (118° C.) under argon for 18 hours. The dark brown reaction mixture was allowed to cool to room temperature. After an hour at room temperature the reaction mixture became very thick with solids. The solids were dissolved with ethyl acetate (100 ml), and the mixture was partially concentrated in vacuo to a viscous brown residue. The residue was concentrated from toluene (240 ml) to remove acetic anhydride, diluted with ethyl acetate (1000 ml), and carefully washed with saturated sodium bicarbonate (4×680 ml). The organic layer was washed with brine (450 ml), dried (magnesium sulfate), filtered and concentrated in vacuo. Residual solvents were removed under high vacuum to produce a light brown solid. The crude product was dissolved in n-butyl acetate (450 ml) with warming (35° C.) and stirring. After cooling to room temperature, hexane (200 ml) was added slowly to the solution with stirring over 15 minutes. At this point the product crystallized from the solution. An additional portion of hexane (700 ml) was added over 30 minutes, and the resulting slurry was stirred for 3 hours. The product was collected by filtration and washed with 1:2 n-butyl acetate:hexane (200 ml), 1:4 n-butyl acetate:hexane (2×240 ml), and hexane (2×50 ml). The product was air-dried, then dried under high vacuum to give 87.7 g of title product as a pale brown solid; m.p. 73° C.; $[\alpha]_D=-1.6°$ (c=1, 95% ethanol). TLC (5% methanol/methylene chloride) $R_f=0.80$.

Anal. calc'd for $C_{16}H_{21}NO_6S$: C, 54.07; H, 5.95; N, 3.94 Found: C, 53.48; H, 5.74; N, 3.82.

e) S-Acetyl-N-[(phenylmethoxy)carbonyl]-L-homocysteine

In a 1 L flask, a solution of the product from part (d) (83.0 g, 0.233 mol) in tetrahydrofuran (415 ml) was sparged with argon for 30 minutes. In a separate 2 L flasked equipped with a mechanical stirrer and an argon inlet, a solution of 86.8% potassium hydroxide (62.7 g, 0.969 mol) in distilled water (280 ml) was sparged with argon for 15 minutes.

The tetrahydrofuran solution was added to the potassium hydroxide solution (internal temperature 20° C.) rapidly, via cannula, with vigorous stirring under argon. The flask containing the product from part (d) was rinsed with 20 ml of tetrahydrofuran (sparged with argon for 15 minutes) and the rinse was added to the reaction mixture. After 30 minutes, the reaction was clear and biphasic, and an exotherm to 28° C. had occurred.

After an additional 2 hours, the reaction was cooled to 1° C. (internal) and sodium borohydride (2.75 g, 0.073 mol) was added in one portion (exotherm to 6.8° C.). The reaction mixture was stirred for an additional 20 minutes at 0° C. and then allowed to warm to 11° C. over 30 minutes. The reaction mixture was cooled to 1° C., and acetic anhydride (68.6 ml, 0.727 mol) was added over 10 minutes. An exotherm to 10° C. occurred during the addition. The internal temperature dropped back to 4° C. before the addition was complete. The cooling bath was removed, and the reaction was stirred at ambient temperature for 45 minutes.

The reaction mixture was concentrated in vacuo to approximately half of its volume, acidified to pH 2 with 6N hydrochloric acid (175 ml), and extracted with ethyl acetate (2×1.1 L). The combined organic extracts were washed with brine (560 ml). The organic layer was treated with activated carbon and anhydrous magnesium sulfate, filtered, and concentrated in vacuo to a yellow oil. n-Butyl acetate (380 ml) was added, and the solution was concentrated in vacuo (45° C.) to half of its volume. A second portion of n-butyl acetate (190 ml) was added and concentrated again such that 190 ml of n-butyl acetate remained. Heptane (300 ml) was added slowly with stirring to haziness, and seed crystals were added. After 15 minutes a white solid crystallized from the solution. A second portion of heptane (570 ml) was added slowly over 30 minutes, and the resulting slurry was stirred at room temperature overnight. The product was collected by filtration, washed with 1:3 n-butyl acetate:heptane (2×275 ml) and hexane (2×275 ml), air-dried, and then dried under high vacuum to produce 50.1 g of title product as a white solid; m.p. 73°–74° C.; $[\alpha]_D=-1.3°$ (c=1, 95% ethanol). TLC (ethanol:water, 3:1) $R_f=0.83$.

Anal. calc'd for $C_{14}H_{17}NO_5S$: C, 54.01; H, 5.50; N, 4.50 Found: C, 53.88; H, 5.45; N, 4.44.

The filtrate was concentrated so that 100 ml of butyl acetate remained. This solution was treated with 310 ml of heptane as described above to obtain a second crop of 8.4 g of title product as a white solid for a total yield of 58.5 g.

f) [S-(R*,R*)-2-[[4-(Acetylthio)-1-oxo-2-[[(phenylmethoxy)carbonyl]amino]butyl]amino]-6,6-dimethoxyhexanoic acid, methyl ester S-Acetyl-N-[(phenylmethoxy)carbonyl]-L-homocysteine (0.456 mol) was dissolved in a mixture of methylene chloride (600 ml) and dimethylformamide (90 ml), and hydroxybenzotriazole hydrate (64.72 g, 0.479 mol) was added. The mixture was cooled in an ice-bath and a solution of (S)-2-amino-6,6-dimethoxyhexanoic acid, methyl ester [prepared as described in Example 1(e), 93.7 g, 0.456 mol) dissolved in methylene chloride (600 ml) was added. Finally, ethyl-3-(dimethylamino)propylcarbodiimide, hydrochloride salt (91.83 g, 0.479 mol) was added and the reaction was stirred for one hour at 0° C., then for 2 hours at room temperature. At the end of that time, the reaction mixture was concentrated in vacuo and the residue was partitioned between ethyl acetate (3 L) and saturated aqueous sodium bicarbonate (1 L). The organic extract was washed with water (1 L), 5% potassium bisulfate (1 L), water (1 L), and brine (1 L), then dried (sodium sulfate) and concentrated in vacuo to 238 g of crude product. The crude product was dissolved in ethyl acetate:methylene chloride (1:1, 300 ml) and applied to a 10×15 cm pad of Merck silica gel. Elution with 8:2 ethyl acetate:hexane (7 L) followed by ethyl acetate (4 L) provided 205.28 g of title product.

g) [4S-(4α,7α,10aβ)]-Octahydro-4-[[(phenylmethoxy)carbonyl]amino]-5-oxo-7H-pyrido[2,1-b][1,3]thiazepine-7-carboxylic acid, methyl ester A solution of the product from part (f) [205.28 g, 0.412 mol, dried by evaporating in methylene chloride/toluene) in methanol (2 L) was cooled to 0° C. (ice bath) and purged with argon for 30 minutes. A 25% by weight solution of sodium methoxide in methanol (95.1 ml, 1.01 eq.) was added rapidly with continued argon purging, and the reaction was stirred for 10 minutes longer, then quenched by the addition of 1 L of saturated ammonium chloride solution, diluted with 0.5 L of water, and treated with 3 L of ethyl acetate. The resulting mixture was divided into two portions which were each separately concentrated in vacuo to remove organics (ethyl acetate and methanol). The concentrated residues were recombined and treated with 1 L of ethyl acetate. The organic layer was separated and rinsed with 0.5 L of saturated ammonium chloride. The combined aqueous solutions were reextracted with 1 L of ethyl acetate. The organic extracts were combined and washed with 1 L of water and two 1 L portions of brine, dried (sodium sulfate), filtered and concentrated. The residue was further evaporated with methylene chloride and dried in vacuo to give 182.65 g of free sulfhydryl of the product from part (f).

This free sulfhydryl intermediate (0.400 mol) was dissolved in methylene chloride (4 L) and treated with 30.8 ml (0.400 mol) of trifluoroacetic acid. The reaction mixture was refluxed for 16 hours, then cooled and concentrated in vacuo. The resulting residue was dissolved in 2 L of ethyl acetate, then washed with 400 ml of 0.1N hydrochloric acid, 1 L of water, 1 L of saturated sodium bicarbonate, 1 L of water, and 1 L of brine, dried (sodium sulfate), filtered and concentrated. The residue was evaporated with methylene chloride and dried in vacuo to afford 166.24 g of title product.

h) [4S-(4α,7α,10aβ)]-Octahydro-4-amino-5-oxo-7H-pyrido[2,1-b][1,3]thiazepine-7-carboxylic acid, methyl ester Iodotrimethylsilane (76.6 ml, 0.538 mol) was added to a solution under argon containing the product from part (g) (162.43 g, 0.414 mol) dissolved in methylene chloride (1.5 L). After stirring for 1.5 hours, the reaction mixture was concentrated in vacuo and the residue was partitioned between 1 L of ethyl acetate and 700 ml of 1N hydrochloric acid (evolution of $CO_2$ occurs; pH 1.2). The ethyl acetate layer was separated and extracted with 300 ml of 1N hydrochloric acid. The combined acidic aqueous extracts were washed with a further 1 L of ethyl acetate, then cooled to 0° C. and basified with 4N sodium hydroxide (about 275 ml) to pH 10.0. The aqueous layer was saturated with solid sodium chloride, then extracted with five 1 L portions of methylene chloride. The combined organic extracts were dried (sodium sulfate), filtered and concentrated in vacuo. The residue was redissolved in 1 L of methylene chloride and rinsed with 0.5 L of brine, dried (sodium sulfate), filtered and concentrated to give 98.8 g of title product.

i) [4S-[4α(R*),7α,10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl ester (S)-2-(Acetylthio)benzenepropanoic acid, dicyclohexylamine salt (173.1 g, 0.427 mol) was partitioned between ethyl acetate (1 L) and 10% potassium bisulfate (800 ml). The organic layer was separated and washed with 5% potassium bisulfate (1 L), 50% brine (1 L) and brine (1 L), dried (sodium sulfate), filtered and concentrated in vacuo. The residue was evaporated several times with methylene chloride, then dried overnight in vacuo to yield 97.3 g of crude (S)-2-(acetylthio)benzenepropanoic acid.

A solution of this (S)-2-(acetylthio)benzenepropanoic acid (0.427 mol) dissolved in methylene chloride (900 ml) was cooled in an ice-bath and treated with a solution of the product from part (h) (100.28 g, 0.388 mol) in methylene chloride (600 ml), triethylamine (154.1 ml, 0.388 mol), and finally benzotriazol-1-yloxytris(dimethylamino)phosphonium hexafluorophosphate (188.9 g, 0.427 mol) added in one portion. After one hour at 0° C. and 2 hours at room temperature, the reaction mixture was concentrated in vacuo and dissolved in 2 L of ethyl acetate. The organic solution was concentrated in vacuo and dissolved in 2 L of ethyl acetate. The organic solution was washed with 0.5 L of brine, 1 L of 0.5N hydrochloric acid, 1 L of water, 2 L of saturated sodium bicarbonate, 1 L of water, and 1 L of brine, dried (sodium sulfate), filtered and concentrated. At this point, those aqueous rinses which contained product (TLC indication) were reextracted with ethyl acetate. The ethyl acetate extracts were worked up in the usual manner and all combined to give a crude yellow oil product. The yellow oil was applied to a 15×15 cm silica gel pad prepared in 1:1 ethyl acetate:hexanes and eluted with 7 L of 1:1 ethyl acetate:hexanes followed by 4 L of 6:4 ethyl acetate:hexanes and finally 2 L of 7:3 ethyl acetate:hexanes. The filtrates containing the desired product were concentrated to give 123.57 g of title product.

j) [4S-4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid Into a 12 l three-necked flask, fitted with an additional funnel and mechanical stirrer, was placed a solution of the product from part (i) (96.0 g, 0.207 mol) in methanol (1.1 l). The solution was purged with argon for 30 minutes then cooled in an ice-bath until the internal temperature was +7° C. A total of 1.45 L of 1N sodium hydroxide solution (previously sparged with argon for 30 minutes) was added over 1 hour. The reaction mixture was continuously sparged with argon during the addition. The reaction temperature rose to +12° C. and was maintained during the addition. The reaction mixture was stirred for an additional 30 minutes, then warmed to room temperature with an ambient water bath and stirred with sparging for 2.5 hours. About 250 ml of 6N hydrochloric acid was added dropwise over 15–20 minutes to adjust the pH to 2. A gummy precipitate formed during the acidification. After continual stirring for a further 2 hours, the precipitate changed to a fine white solid, with the presence of some larger chunks of solid product. The product was collected on a 600 ml sintered glass funnel. Washing the collected solid with 1 L of water followed by 2 L of anhydrous ether and final drying in vacuo afforded 70.3 g of title product as a fine white solid; m.p. 218°–220° C. (dec.). TLC (1:99 acetic acid/ethyl acetate) $R_f$=0.48.

HPLC: $t_R$ (YMC S-3 ODS 6.0×150 mm; 1.5 mL/min., isocratic 60% B, Buffer A=methanol/water/phosphoric acid (10:90:0.2), Buffer B=methanol/water/phosphoric acid (90:10:0.2))=9.33 min., 99.3% of total peak area at 220 nm.

Anal. calc'd for $C_{19}H_{24}N_2O_4S_2$: C, 55.86; H, 5.92; N, 6.86; S, 15.70 Found: C, 55.83; H, 5.83; N, 6.96; S, 15.70.

EXAMPLE 24

[4S-[4α(R*),7α,10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl ester The coupling reaction described in Examples 3(c), 11(i), 22(b), and 23(i) was also carried out as follows:

A solution of (S)-2-(acetylthio)benzenepropanoic acid (1.83 g, 8.14 mmol) and [4S-(4α,7α,10aβ)]octahydro-4-amino-5-oxo-7H-pyrido[2,1-b][1,3]thiazepine-7-carboxylic acid, methyl ester (2.11 g, 8.17 mmol) in dry methylene chloride (20 ml) was cooled to 0° C. and ethyl-3-(dimethylamino)propyl carbodiimide, hydrochloride salt (1.77 g, 9.32 mmol) was added in a single portion. The reaction mixture was stirred at 0° C. for 6 hours and then was concentrated to an oily foam. The residue was then partitioned between ethyl acetate (100 ml) and 1N hydrochloric acid (50 ml). The organic phase was washed with 1N hydrochloric acid (50 ml), saturated aqueous sodium bicarbonate (2×50 ml), and saturated aqueous sodium chloride (50 ml), dried (anhydrous sodium sulfate), filtered and concentrated in vacuo to give 3.43 g of title product as a white foam.

EXAMPLE 25

[4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid, 1,1-dimethylethylamine salt A 15 ml, 3-necked flask equipped with a reflux condenser was evacuated and refilled with argon three times. [4S-[4α(R*),7α,10aβ]-Octahydro-4-[(2-mercapto-1-oxo-3-phenylpropyl)amino]-5-oxo-7H-pyrido[2,1-b][1,3]thiazepine-7-carboxylic acid (0.20 g) and a 1:1 solution of degassed absolute ethanol and acetonitrile (1.0 ml) were charged into the flask. As the heterogeneous mixture was stirred, tert-butylamine (53.0 µl, 1.03 eq.) was added dropwise. The solution became homogeneous within three minutes after the amine addition was completed. The solution (internal temperature of 20° C.) was diluted slowly by the dropwise addition of acetonitrile to a final volume of 10 ml. After an additional 2 hours of stirring, the solids were filtered, washed once with 100% acetonitrile (5 ml), air dried, and placed under high vacuum for 2 hours to remove residual solvents to give 0.2 g of title product as a white crystalline solid.

The above material was combined with material from other runs and recrystallized as follows. A 25 ml, 3-necked flask equipped with a reflux condenser, magnetic stirrer bar, and addition funnel was evacuated and refilled with argon three times. The batches of 1,1-dimethylamine salt product (0.37 g) and 59% acetonitrile/ethanol (2.28 ml) were added to the flask. The flask and contents were warmed to 29°-32° C. to dissolve the solids. The solution was diluted with acetonitrile (27 ml). The heating bath was removed, and the flask was allowed to cool to room temperature (20° C.). After one hour of additional stirring, the mixture was filtered, and the solids were washed once with acetontrile (10 ml), air-dried, and placed under high vacuum to remove residual solvents and give 0.29 g of title product as a white crystalline solid; m.p. shrinks at 160° C. and slowly melts and decomposes as the temperature is increased to 190°-191° C. (at 190°-191° C., the remaining glossy material melts rapidly).

EXAMPLE 26

[4S-(4α,7α,10aβ)]-Octahydro-4-amino-5-oxo-7H-pyrido[2,1-b]1,3]thiazepine-7-carboxylic acid, methyl ester This intermediate of Examples 3(c), 11(h) and 23(h) was also prepared as follows:

a) 2-(Acetylamino)-2-[4-(acetyloxy)butyl] propanedioic acid, diethyl ester

A stirred suspension of 95% sodium hydride (60.8 g, 2.532 mol) in anhydrous dimethylformamide (500 ml) under an atmosphere of argon was cooled to 0° C. (ice bath). A solution of diethyl acetamidomalonate (500 g, 2.302 mol) in anhydrous dimethylformamide (1.2 l) was added over a period of 45 minutes while keeping the reaction temperature below 18° C. After the addition was complete, the turbid solution was gradually warmed to room temperature. After stirring for one hour at room temperature, 4-bromobutyl acetate (471.5 g, 2.417 mol) was added. The mixture was then stirred at 59°-60° C. for 18 hours. The resulting slurry was cooled to room temperature, quenched with absolute ethanol (40 ml) and glacial acetic acid (4 ml), stirred for about 15 minutes, poured into a 10% lithium chloride solution and extracted with ethyl acetate (2×3 l). The combined ethyl acetate extracts were washed with 10% lithium chloride (3×3 l), dried (anhydrous sodium sulfate), and evaporated in vacuo to give 750 g of title product as an oil.

b) 2-(Acetylamino)-6-hydroxyhexanoic acid

The product from part (a) (730 g, 2.2 mol) was weighed into a 5 l. 3-neck flask (equipped with a thermometer, magnetic stirrer and air cooled condenser) and diluted with absolute ethanol (300 ml) followed by the addition of aqueous 6N sodium hydroxide (1.6 l, 9.6 mol). The reaction mixture was heated at 68°-70° C. for 5 hours and a homogenous solution was obtained. The reaction was cooled to room temperature, and 6N hydrochloric acid (1.32 l) was added slowly to pH 1.3. The flask was equipped with a short path still head to distill off the ethanol as the temperature was slowly increased to 87°-90° C. and maintained at this temperature for 8.5 hours. Slow carbon dioxide evolution was observed. The total volume of distillate was 600 ml. The pH of the final solution was 3.0. The reaction mixture was concentrated in vacuo until all of the water evaporated off and then concentrated from toluene (2×500 ml). The semi-solid mass was triturated with absolute ethanol (1 l), filtered, and rinsed with additional absolute ethanol (500 ml). The filtrate was concentrated in vacuo to yield 509 g of crude oil (82% purity) which contained ethanol and toluene.

c) (S)-2-Amino-6-hydroxyhexanoic acid

The crude product from part (b) (443 g, includes some toluene and ethanol, starting material weight estimated to be 394 g) was dissolved in water (3.3 l) and 1N lithium hydroxide was added until the pH was 7.5 (1.53 l required). The mixture was heated to 35° C. and acylase (grade 1 from porcine kidney, 0.4 g) was added and the reaction mixture was stirred for 24 hours. At the end of this time period the pH was 7.33. The pH was readjusted to 7.5 with 1N lithium hydroxide (about 2 ml), additional acylase (0.4 g) was added, and the reaction was stirred for 17 more hours (pH 7.3). The pH of the solution was adjusted to 5.9 with acetic acid. Celite® (20 g) and charcoal (20 g) were added and the reaction was heated to 92° C. and maintained for 5 minutes. The reaction was filtered through a pad of Celite® and concentrated in vacuo to a semi-paste (441 g). This was triturated with 900 ml of 1:5:10 water:ethanol:dimethylformamide. Some warming was required to break up the original cake. The reaction mixture was refrigerated overnight, filtered, and washed with 200 ml. of the above solvent mixture to yield 214 g of crude material (about 40% N-acetyl material). This material was suspended in methanol (500 ml), warmed on a steam bath, allowed to stand for 2 hours, and filtered. This procedure was repeated a second time to yield 108 g of title product; [α]$_D$=+22° (c=1.44, 6N hydrochloric acid).

Alternatively, steps (b) and (c) were also performed as follows:

b) 2-(Acetylamino)-6-hydroxyhexanoic acid

A 5 l, 3-necked flask, equipped with a mechanical stirrer and thermocouple thermometer, was charged with the product from part (a) (631 g, 1.933 mol) and tetrahydrofuran (259 ml). A 6N sodium hydroxide solution (1385 ml, 8.31 mol) was added to the stirred solution over 40 minutes. A strong exotherm occurred and it was necessary to cool the reaction mixture in an ice bath to keep the temperature under 60° C. The reaction mixture was then heated to slight reflux (pot temperature at 67°–68° C.) for 5.5 hours.

The mixture was stirred at room temperature overnight (16.5 hours). The pH was brought from 12.75 to 1.30 with the gradual addition of 6N hydrochloric acid solution (1150 ml, 6.9 mol), maintaining the temperature at about 25° C. The mixture was heated gradually with a short distillation head until distillation and gas (carbon dioxide) evolution started (72.3° C. pot temperature, 70° C. head temperature) and until distillation stopped and gas evolution became very slow (94.1° C. pot temperature, 50° C. head temperature). Total distillate collected was 410 ml and the pot residue had a pH of 3.9. Heating was continued for another ten minutes with no additional gas evolution. Total heating time from the start of distillation was 7.5 hours.

After stirring at room temperature overnight, the clear reaction mixture (pH 3.50) was stripped in the rotary evaporator under vacuum in a 60° C. bath and the pasty residue was stirred with absolute ethanol (750 ml). The resulting crystalline suspension was stripped in the rotary evaporator (pump vacuum, 60° C. bath) and the pasty residue was chased with absolute ethanol (2×750 ml). To the final residue, absolute ethanol (1500 ml) was added and the mixture was stirred in a 60° C. bath until it became a fine crystalline suspension, about 20 minutes, and then stirred at room temperature for 20 minutes. The suspension was filtered and the cake was washed with absolute ethanol (2×300 ml). The filtrates appeared hazy and were further clarified by filtration through a pad of Celite®. The new, clear filtrate was stripped in the rotary evaporator to give 434.6 g of title product as an amber-colored thick syrup. TLC (10:1:1, methanol:acetic acid:water) R$_f$=0.59.

c) (S)-2-Amino-6-hydroxyhexanoic acid

A 5 l, 3-necked flask, equipped with a mechanical stirrer and thermometer, was charged with the product from part (b) (434 g ,1.93 mol), and water (3 l). The pH of the hazy solution was adjusted from 4.05 to 7.50 by the addition of 1N lithium hydroxide (705 ml). The solution was warmed to 36° C. and porcine kidney acylase I (0.710 g) was added. The mixture was stirred at 35° to 36° C. for 23.5 hours. The reaction mixture was cooled to room temperature and the pH was brought from 7.0 to 5.9 by the addition of glacial acetic acid (4.4 ml). Celite® (29 g) and charcoal (29 g) were added and the temperature was raised with stirring to 91° C. The heating was removed and the mixture was allowed to cool to room temperature. The suspension was filtered through an 18.5 cm filter paper disc and the cake was thoroughly washed with water. The colorless filtrates (about 3.9 l) were concentrated in a rotary evaporator at 60° C. to give 476 g of a clear, thick oil. Absolute ethanol (720 ml) was added and the mixture was stirred until it became a homogeneous crystalline suspension. The solvent was again stripped off and absolute ethanol (1584 ml) was added to the white solid residue. The suspension was rolled in the rotary evaporator at room temperature overnight (15 hours) and filtered through 18.5 cm paper. The cake was washed with absolute ethanol (7×100 ml) and dried to constant weight under vacuum to give 85.8 g of white, crystalline title product. TLC (methanol:water:acetic acid, 10:1:1) R$_f$=0.62.

Anal. calc'd for $C_6H_{13}NO_3$: C, 48.25; H, 8.94; N, 9.38 Found: C, 48.66; H, 8.77; N, 9.43.

d) [S-(R*,R*)-2-[[4-(Acetylthio)-1-oxo-2-[[(phenylmethoxy)carbonyl]amino]butyl]amino]-6-hydroxyhexanoic acid, methyl ester A slurry of (S)-2-amino-6-hydroxyhexanoic acid (1.0 g, 6.8 mmol) in methanol (20 ml) was stirred under argon at room temperature and treated with trimethylsilyl chloride (1.9 ml, 15 mmol). The resulting solution was stirred at room temperature for 18 hours. The solvent volume was reduced to about 3.5 ml under reduced pressure. Acetonitrile (5 ml) was added and the solution was cooled to –10° C. N,N-Diisopropylethylamine (4.15 ml, 23.8 mmol) was then added and the solution was cooled to –40° C. to give a solution containing (S)-2-amino-6-hydroxyhexanoic acid, methyl ester.

In a separate flask, a solution of S-acetyl-N-[(phenylmethoxy)carbonyl]homocysteine [prepared as described in Example 23(e), 2.117 g, 6.8 mmol] in acetonitrile (5 ml) at 0° C. was treated with N,N-diisopropylethylamine (1.20 ml, 6.8 mmol). In another flask, hydroxybenzotriazole hydrate (0.104 g, 0.68 mmol) and methanesulfonyloxybenzotriazole (1.450 g, 6.8 mmol) were dissolved in acetonitrile and cooled to –18° C. The previously formed S-acetyl-N-[(phenylmethoxy)carbonyl] homocysteine was then added dropwise to this solution while maintaining the internal temperature at less than –10° C. After stirring at –18° to –12° C. for three hours, the resulting solution was added dropwise to the above solution containing (S)-2-amino-6-hydroxyhexanoic acid, methyl ester at –40° C. The mixture was allowed to slowly warm to 16° C. over 18 hours. The reaction was then poured into ethyl acetate (50 ml) and 1N hydrochloric acid (50 ml). The mixture was transferred into a separatory funnel and the layers were separated. The aqueous layer was extracted with ethyl acetate (2×50 ml). The organic layers were combined and then washed with 1N hydrochloric acid (100 ml), saturated sodium bicarbonate (100 ml), and saturated sodium chloride (100 ml). The solution was dried over magnesium sulfate, filtered, and concentrated to a white solid. To this solid was added tert-butyl methyl ether (20 ml) and the resulting slurry was stirred at room temperature for 4 hours and filtered. The product was washed with tert-butyl methyl ether and dried to yield 2.087 g of title product; m.p. 89°–90° C.

e) [S-(R*,R*)]-2-[[4-(Acetylthio)-1-oxo-2-[[phenylmethoxy)carbonyl]amino]butyl]amino]-6-oxohexanoic acid, methyl ester To a solution of oxalyl chloride (546 μl, 6.27 mmol) in dry methylene chloride (16 ml) at –65° C. (internal temperature) was added dropwise a solution of dimethylsulfoxide (905 μl, 12.54 mmol) in methylene chloride (13 ml) over 12 minutes while maintaining an internal temperature between –65° and –60° C. A solution of the product from part (d) (1.90 g, 4.18 mmol) in methylene chloride (7 ml) was added to the reaction flask over 20 minutes producing a turbid mixture. Additional methylene chloride (1 ml) was used to complete the transfer of the alcohol into the reaction flask and the reaction was allowed to stir at –65° C. for 40 minutes. Next N,N-diisopropylethylamine (3.7 ml, 20.90 mmol) was added thus producing a clear solution. After stirring an additional 30 minutes at –65° C., the reaction was allowed to warm to −18° C. over 2 hours. The reaction was quenched with 10% aqueous potassium bisulfate (30 ml) and then warmed to room temperature. The reaction mixture was diluted with 25 ml of water, mixed, and the phases were separated. The aqueous fraction was back-extracted with methylene chloride (2×25 ml). The combined organic extracts were washed with 10% aqueous potassium bisulfate (25 ml), saturated aqueous sodium bicarbonate (2×25 ml), brine (25 ml), dried (magnesium sulfate), filtered and concentrated in vacuo to give 1.84 g of title product as a white solid.

f) [4S-(4α,7α,10aβ)]-Octahydro-4-[[(phenylmethoxy)carbonyl]amino]-5-oxo-7H-pyrido[2,1-b][1,3]thiazepine-7-carboxylic acid, methyl ester A dried flask under argon was charged with the product from part (e) (1.76 g, 3.89 mmol) and methanol (17 ml). The solution was cooled to 0° C. and sparged with argon for 25 minutes. Sodium methoxide solution (25% by weight in methanol, 983 µl, 4.28 mmol) was added to the reaction mixture over about 15 seconds. The reaction was quenched after one hour with 1N hydrochloric acid solution (20 ml) and then allowed to warm to room temperature. Ethyl acetate (35 ml) was added and after mixing, the layers were separated. The aqueous fraction was back-extracted with ethyl acetate (2×15 ml). The combined organic fractions were washed with 1N hydrochloric acid solution (15 ml), brine, dried (magnesium sulfate), filtered, and concentrated in vacuo to give 1.69 g of [S-(R*,R*)]-2-[[4-mercapto-1-oxo-2-[[(phenylmethoxy)carbonyl]amino]butyl]amino]-6-oxohexanoic acid, methyl ester as a white foam.

A solution of this white foam and trifluoroacetic acid (305 µl, 3.95 mmol) in methylene chloride (17 ml) was refluxed for 2.25 hours. After cooling to room temperature, the reaction was concentrated and the residue was dissolved in ethyl acetate (25 ml), washed with saturated sodium bicarbonate solution (2×20 ml) and brine, dried (magnesium sulfate), filtered and concentrated in vacuo to yield 1.50 g of title product as a white foam.

g) [4S-(4α,7α,10aβ)]-Octahydro-4-amino-5-oxo-7H-pyrido[2,1-b][1,3]thiazepine-7-carboxylic acid, methyl ester Treatment of the product from part (f) with iodotrimethylsilane according to the procedure of Example 23(h) or 11(h) removes the N-protecting group and yields the desired 4-amino product.

EXAMPLE 27

(S)-2-Phthalimido-6-hydroxyhexanoic acid

This intermediate of Example 1(c) was also prepared as follows:

To a solution of 2-(acetylamino)-2-[4-(acetyloxy)butyl]propanedioic acid, diethyl ester [730 g, 2.2 mol, prepared as described in Example 24(a)] in absolute ethanol (300 ml) was added 6N sodium hydroxide solution (1.6 l). The reaction was heated at 70°–75° C. for 5 hours, then at 90° to 95° C. to distill off most of the ethanol. The reaction was cooled and acidified to pH 1.3 using 6N hydrochloric acid (about 1.3 l), then heated at 90°–100° C. to achieve decarboxylation. Upon completion, the crude reaction mixture was cooled to room temperature.

The above crude reaction mixture was heated to 35° C. and treated with about 600 ml of 6N sodium hydroxide followed by 1N sodium hydroxide to adjust to pH of 7.5 (final volume was about 5.3 l). To this mixture was added 0.6 g of porcine kidney acylase I. After stirring overnight at 35° C. the pH was 7.25. The pH was adjusted to 7.5 and an additional 300 mg of acylase was added. After stirring overnight, the reaction appeared to be about 90% complete. The reaction mixture was next treated with 20 g of charcoal and 20 g of Celite®, then heated to 85° C. and maintained at that temperature for 10 minutes, then cooled to 50° C. and filtered. At this point, the total volume of the filtrate was about 4.9 l. The filtrate was cooled to 5° C. and solid sodium carbonate was added to adjust the pH to 9.3. N-Carbethoxyphthalimide (263.04 g, 1.2 mol) was added in one portion and sodium carbonate was added as needed to keep the pH at 9.3. After 2 hours at 5° C. followed by 3 hours at room temperature, the pH dropped to 8.5 and most of the reagents had dissolved. The reaction mixture was filtered, cooled to 5° C. and acidified to pH 2.3 with 6N hydrochloric acid. The precipitated solid was collected by filtration and washed with 200 ml of cold water, then dried in vacuo to yield 220 g of title product.

EXAMPLE 28

[4S-(4α,7α,10aβ)]-Octahydro-4-[[2-mercapto-3-(1-naphthalenyl)-1-oxopropyl]amino]-5-oxo-7H-pyrido[2,1-b][1,3]thiazepine-7-carboxylic acid a) (Acetylamino)(1-naphthalenylmethyl)propanedioic, diethyl ester

To a solution of sodium ethoxide (21% in ethanol, 4.613 gm, 67.8 mmol) in ethanol (100 ml) was added diethyl acetamidomalonate (14.74 gm, 67.8 mmol), then 1-(bromomethyl)napthalene (10.0 gm, 45.2 mmol). The solution was stirred at room temperature for one hour. The reaction mixture was then concentrated to an orange oil. The oil was dissolved in ethyl acetate and washed with 50% saturated ammonium chloride water and brine, then dried over sodium sulfate, filtered and concentrated to afford an orange solid. The solid was recrystallized from ethyl acetate and hexane to afford beige crystals contaminated with diethylacetamido malonate. The solid was dissolved in 50% ethyl acetate in hexane and purified by flash chromatography on Merck silica gel in 50% ethyl acetate in hexane. Those fractions containing pure product were combined and concentrated to afford 10.225 g. of product as a white solid; m.p. 105°–108° C.; $R_f$=0.57 (50% ethyl acetate in hexane).

b) α-Amino-1-naphthalenepropanoic acid

A solution of the product from part (a) (16.182 gm., 47.5 mmol) was suspended in 48% hydrogen bromide (100 ml) and refluxed under argon for 14 hours. The hydrogen bromide salt of the product was filtered out of solution as a white solid, then taken up in hot (50 ° C.) water (500 ml) and the solution neutralized with concentrated ammonium hydroxide. The product precipitated out of solution as a fine white solid. Upon filtration and drying under high vacuum overnight (18 hours), 8.335 g. of product was obtained as a fluffy white solid; m.p. 264 ° C.

c) α-Bromo-1-naphthalenepropanoic acid

To a solution of the product from part (b) (4.000 g., 18.6 mmol) and potassium bromide (7.63 g., 63.2 mmol) in 2.5N sulfuric acid (35 ml) kept at 0 ° C. was added sodium nitrite (1.92 g., 27.8 mmol) over one hour. The mixture was stirred for an additional hour at 0° C., then was warmed to room temperature and stirred for 2.5 hours. The reaction mixture was then extracted with ether (3×). The ether layers were combined and washed with water and brine, then dried over sodium sulfate, filtered and concentrated to give an orange oil. The oil was purified by flash chromatography on Merck silica gel in 70% ethyl acetate in hexane with 1% acetic acid added to reduce tailing. Those fractions containing the bromide were combined and concentrated to afford slightly contaminated product as an orange oil which solidified upon sitting overnight. $R_f$=0.40 (40% ethyl acetate in hexane with 1% acetic acid).

d) α-(Acetylthio)-1-naphthalenepropanoic acid

To a slurry of potassium thioacetate (0.912 g., 8.00 mmol) in acetonitrile (300 ml) at 0° C. was added the product from part (c) (2.030 g., 7.27 mmol) as a solution in acetonitrile (3 ml). The solution was stirred for one hour at 0° C., then was warmed to room temperature and stirred for 15 hours. Potassium bromide was then filtered out of the reaction mixture and the filtrate concentrated to afford an orange oil. The oil was dissolved in ethyl acetate and washed with 10% potassium bisulfate and brine, then dried over sodium sulfate, filtered and concentrated to afford an orange oil. The oil was purified by flash chromatography on Merck silica gel in 50% ethyl acetate in hexane with 1% acetic acid added to reduce tailing. Those fractions containing product were all contaminated with a compound with an $R_f$=0.43. Those fractions were pooled and concentrated to give an orange oil. The crude product was purified via the dicyclohexylamine salt by dissolving the orange oil in ether and adding an equivalent of dicyclohexylamine (1.32 g., 7.27 mmol) to the solution. The dicyclohexylamine salt was obtained in 2 crops of brown crystals (1.450 gm) still slightly contaminated with impurity. The crystals were suspended in ethyl acetate and shaken with 10% potassium bisulfate (3×). The organic layer was then washed with water and brine, then dried over sodium sulfate filtered and concentrated to afford 875 mg. of product as a yellow oil; $R_f$=0.40 (40% ethyl acetate in hexane with 1% acetic acid).

e) [4S-(4α,7α,10aβ)]-Octahydro-4-[[2-(acetylthio)-3-(1-naphthalenyl)-1-oxopropyl]amino]-5-oxo-7H-pyrido[2,1-b][1,3]thiazepine-7-carboxylic acid, methyl ester A solution of the racemic acid product from part (d) in methylene chloride and a solution of [4S-(4α,7α,10aβ)]-octahydro-4-amino-5-oxo-7H-pyrido[2,1-b][1,3]thiazepine-7-carboxylic acid, methyl ester in methylene chloride are reacted in the presence of triethylamine and benzotriazol-1-yloxytris(dimethylamino)phosphonium hexafluorophosphate according to the procedure of Example 23(i) to give the title product.

f) [4S-(4α,7α,10aβ)]-Octahydro-4-[[2-mercapto-3-(1-naphthalenyl)-1-oxopropyl]amino]-5-oxo-7H-pyrido[2,1-b][1,3]-thiazepine-7-carboxylic acid A solution of the product from part (e) in methanol is treated with 1N sodium hydroxide according to the procedure of Example 23(j) to give the title product.

EXAMPLE 29

[4S-[4α(R*),7α,10aβ]]-Octahydro-4-[[2-mercapto-1-oxo-3-(2-thienyl)propyl]amino]-5-oxo-7H-pyrido[2,1-b][1,3]thiazepine-7-carboxylic acid a) (S)-α-(Acetylthio)-2-thiophenepropanoic acid

Potassium chloride (3.0 g., 40.1 mmol.) was added to a solution of β-(2-thienyl)-D-alanine (1.37 g., 8.03 mmol.) in 2.5N hydrochloric acid (25 ml.) at room temperature under argon. After stirring for 10 minutes, the resulting mixture was cooled to 0° C. and treated with sodium nitrite (720 mg., 10.44 mmol.). After 2.5 hours, the reation mixture was warmed to room temperature and was stirred 1 hour. The mixture was partitioned between water and ethyl acetate and the organic layer was dried (sodium sulfate), filtered, and concentrated. The residue was flash chromatographed (Merck silica gel) eluting with 1% acetic acid in 3:1 hexane/ethyl acetate to give 760 mg. of (R)-α-chloro-2-thiophenecarboxylic acid as a yellow oil.

Cesium thioacetate (2.95 g., 14.19 mmol.) was added to a solution containing the above chloride (750 mg., 4.73 mmol.) in dimethylformamide (15 ml.) at room temperature under argon. After stirring for 2 hours, the reaction mixture was partitioned between 10% potassium bisulfate and ethyl acetate. The organic layer was washed with brine, dried (sodium sulfate), filtered, and concentrated and the residue was flash chromatographed (Merck silica gel) eluting with 1% acetic acid in 4:1 hexane/ethyl acetate to give 500 mg. of the title product as an oil. TLC (2% acetic acid in 3:1 ethyl acetate/hexane) $R_f$ 0.73.

b) [4S-[4α(R*),7α,10aβ]]-Octahydro-4-[[2-(acetylthio)-1-oxo-3-(2-thienyl)propyl]amino]-5-oxo-7H-pyrido[2,1-b][1,3]thiazepine-7-carboxylic acid, methyl ester A solution of the acid product from part (a) in methylene chloride and a solution of [4S-(4α,7α,10aβ)]-octahydro-4-amino-5-oxo-7H-pyrido[2,1-b][1,3]thiazepine-7-carboxylic acid, methyl ester in methylene chloride are reacted in the presence of triethylamine and benzotriazol-1-yloxytris(dimethylamino)phosphonium hexoflurophosphate according to the procedure of Example 23(i) to give the title product.

c) [4S-[4α(R*),7α,10aβ]]-Octahydro-4-[[2-mercapto-1-oxo-3-(2-thienyl)propyl]amino]-5-oxo-7H-pyrido-[2,1-b][1,3]thiazepine-7-carboxylic acid A solution of the product from part (b) in methanol is treated with 1N sodium hydroxide according to the procedure of Example 23(j) to give the title product.

EXAMPLE 30

[4S-[4α(S*),7α,10aβ]]-Octahydro-4-[(2-mercapto-1-oxo-3-phenylpropyl)amino]-5-oxo-7H-pyrido[2,1-b][1,3]thiazepine-7-carboxylic acid a) (R)-2-(Acetylthio)benzenepropanoic acid, dicylohexylamine salt

Following the procedure of Example 1(h) but substituting L-phenylalanine for the D-phenylalanine, (R)-2-(acetylthio)benzenepropanoic acid, dicyclohexylamine salt was obtained.

b) [4S-[4α(S*),7α,10aβ]]-Octahydro-4-[[2-(acetylthio)-1-oxo-3-phenylpropyl]amino]-5-oxo-7H-pyrido[2,1-b][1,3]thiazepine-7-carboxylic acid, methyl A stirred suspension of (R)-2-(acetylthio)benzenepropanoic acid, dicyclohexylamine salt (353.5 mg, 0.872 mmol) in ethyl acetate (5 ml) was washed with 5% potassium bisulfate solution (3×5 ml). The organic extracts were combined, washed with brine, dried (magnesium sulfate), filtered, concentrated, dried in vacuo and stripped twice from hexanes to obtain (R)-2-(acetylthio)benzenepropanoic acid as an oil.

The resulting free acid (181.4 mg, 0.809 mmol) was dissolved in methylene chloride (2 ml) and stirred under nitrogen at 0° C. To this solution was added a solution of [4S-(4α,7α,10aβ)]-octahydro-4-amino-5-oxo-7H-pyrido[2, 1-b][1,3]thiazepine-7-carboxylic acid, methyl ester (200 mg, 0.774 mmol) in methylene chloride (6 ml), then triethylamine (0.113 ml, 0.813 mmol) and finally benzotriazol-1-yloxytris(dimethylamino)phosphonium hexafluorophosphate (360 mg, 0.813 mmol). The reaction was stirred at 0° C. and then slowly allowed to warm to room temperature. After a total of 20 hours, the reaction was concentrated in vacuo. The residue was dissolved in ethyl acetate and the solution was washed with a 5% solution of potassium bisulfate, a saturated solution of sodium bicarbonate, and brine. The organic layer was dried (magnesium sulfate), filtered, and concentrated to a yellow solid. Purification by flash chromatography (eluting with 2:3 ethyl acetate/hexane) gave 261.7 mg of title product as a clear oil.

c) [4S-[4α(S*),7α,10aβ]]-Octahydro-4-[(2-mercapto-1-oxo-3-phenylpropyl)amino]-5-oxo-7H-pyrido[2,1-b][1,3]thiazepine-7-carboxylic acid A solution of the product from part (b) (261.1 mg, 0.562 mmol) in methanol (6 ml, deoxygenated via nitrogen bubbling) was cooled to 0° C. and treated with 1N sodium hydroxide (6 ml, deoxygenated via nitrogen bubbling). After stirring for one hour at 0° C. while purging continuously with nitrogen, the reaction was warmed to room temperature. After stirring for 30 minutes at room temperature, a clear solution was obtained. After 5.5 hours, the reaction was acidified, to pH 1 with 5% potassium bisulfate and extracted with ethyl acetate. The organic layers were combined, washed with water and brine, dried (sodium sulfate), filtered and concentrated in vacuo. Purification by flash chromatography (6:0.01:3.99 ethyl acetate:acetic acid:hexane) gave 190 mg of title product as a white solid; $[\alpha]_D = -87.5°$ (c=0.51, chloroform). TLC (6:0.01:3.99, ethyl acetate:acetic acid:hexane) $R_f = 0.20$.

HPLC: $t_R = 25.3$ min; YMC S-3 ODS (C-18) 6.0×150 mm; 0% to 100% B:A, 30 min. linear gradient and 10 min. hold, 1.5 ml/min; A=90% water:methanol+0.2% phosphoric acid, B=90% methanol:water+0.2% phosphoric acid; 220 nm.

Anal. calc'd for $C_{19}H_{24}O_4N_2S_2 \cdot 0.15$ $C_4H_8O_2 \cdot 0.15$ $C_7H_{16} \cdot 0.39$ $H_2O$: C, 55.89; H, 6.45; N, 6.31; S, 14.45 Found: C, 56.19; H, 6.50; N, 6.71; S, 13.96.

EXAMPLE 31

[4S-(4α,7α,9aβ)]-Octahydro-4-[[2-mercapto-1-oxo-3-(4-thiazolyl)propyl]amino]-5-oxopyrrolo[2,1-b][1,3]thiazepine-7-carboxylic acid a) (R)-2-Amino-3-(4-thiazolyl)propanoic acid A solution of 4N hydrochloric acid in dioxane (10 ml) was added to a solution of (R)-2-[[(1,1-dimethylethoxy)carbonyl]amino]-3-(4-thiazolyl)propanoic acid (2.0 g, 7.3 mmol) in dioxane (2 ml). The reaction mixture was stirred at room temperature for 3 hours, concentrated in vacuo and the residue was dissolved in water (3 ml). The pH was adjusted to 6.5 with 1N sodium hydroxide and this solution was passed through 20 ml of Dowex® AG50(H⁺). The column was eluted with water (250 ml) followed by 2% pyridine in water (300 ml). The product containing fractions were concentrated in vacuo to yield 0.94 g of title product.

b) (R)-2-Bromo-3-(4-thiazolyl)propanoic acid

A solution of the product from part (a) (0.516 g, 3 mmol) and potassium bromide (1.19 g, 10.1 mmol) in water (5.94 ml) and sulfuric acid (0.43 ml) was stirred at −10° C. for 5 minutes followed by the portionwise addition of sodium nitrite (0.318 g, 4.61 mmol) over a 10 minute period. The reaction mixture was stirred an additional 10 minutes at 0° C. and at room temperature for one hour, and then extracted with ether (3×100 ml). The ether extracts were washed with brine (2×20 ml), dried (sodium sulfate), filtered, and concentrated in vacuo to yield 0.37 g of title product; $[\alpha]_D = +37.35°$ (c=0.7, methanol). A second run was carried out starting with 2.67 mmol of the product from part (a) using the same procedure to yield an additional 0.35 g of title product.

c) (S)-2-(Acetylthio)-3-(4-thiazolyl)propanoic acid

The product from part (b) (0.72 g, 3.05 mmol) and potassium thioacetate (0.35 g, 3.05 mmol) were stirred in acetonitrile (9 ml) overnight at room temperature and at 30° C. for one hour. The reaction mixture was diluted with ethyl acetate (100 ml) and filtered. The filtrate was concentrated in vacuo. The residue was redissolved in ethyl acetate (100 ml), washed with water (2×50 ml) and brine (20 ml), dried (sodium sulfate), filtered and concentrated in vacuo to yield 0.52 g of title product; $[\alpha]_D = -15.89°$ (c=0.6, methanol).

d) [4S-(4α,7α,9aβ)]-Octahydro-4-[[2-(acetylthio)-1-oxo-3-(4-thiazolyl)propyl]amino]-5-oxopyrrolo-[2,1-b][1,3]thiazepine-7-carboxylic acid, methyl ester

[4S-(4α,7α,9aβ)]-4-Amino-octahydro-5-oxopyrrolo[2,1-b][1,3]thiazepine-7-carboxylic acid, methyl ester, p-toluenesulfonic acid salt [0.367 g, 0.882 mmol, prepared from the material described in Example 5(d)] was dissolved in methylene chloride (5 ml) 0° C., followed by the addition of triethylamine (0.12 ml, 0.868 mmol). The product from part (c) (0.2 g, 0.865 mmol) was added to this solution followed by a second portion of triethylamine (0.12 ml, 0.865 mmol). Benzotriazol-1-yloxytris(dimethylamino)phosphonium hexafluorophosphate (0.383 g, 0.865 mmol) was added and the reaction mixture was stirred at 0° C. for one hour and a room temperature for 4 hours. The reaction mixture was concentrated in vacuo and the residue was dissolved in ethyl acetate (60 ml). The organic extract was washed with 5% aqueous potassium bisulfate (10 ml) and brine (2×10 ml), dried (sodium sulfate), filtered and concentrated in vacuo. This crude material was chromatographed through 100 g of Merck silica gel using 0.2% methanol in ethyl acetate. The fractions enriched in the slower isomer were concentrated in vacuo to yield 0.134 g of title product.

e) [4S-(4α,7α,9aβ)]-Octahydro-4-[[2-mercapto-1-oxo-3-(4-thiazolyl)propyl]amino]-5-oxopyrrolo[2,1-b][1,3]thiazepine-7-carboxylic acid The product from part (d) (0.135 g, 0.29 mmol) was dissolved in methanol (3 ml) and argon was bubbled into the solution for 30 minutes at 0° C. 1N Sodium hydroxide (1.32 ml) also purged with argon was added to the above solution and the reaction mixture was stirred at 0° C. with argon bubbling through the solution for one hour and at room temperature for 2 hours. The reaction was quenched by the addition of 5% aqueous potassium bisulfate (20 ml) and the organics were extracted with ethyl acetate (3×50 ml). The ethyl acetate solution was washed with brine, dried (sodium sulfate), filtered, and concentrated in vacuo. The concentrate was chromatographed through 40 g of Merck silica gel using chloroform containing 5% methanol and 0.5% acetic acid. The appropriate fractions were combined, concentrated and partitioned between 20 ml of ethyl acetate and 5% aqueous potassium bisulfate. The ethyl acetate solution was washed with water and brine, dried (sodium sulfate), and concentrated in vacuo. The residue was lyophilized from dioxane (4 ml) to yield 36 mg of title product as a 70:30 mixture of isomers; m.p. 95°–115° C.; $[\alpha]_D = -191.7°$ (c=0.06, chloroform). TLC (chloroform:methanol:acetic acid, 8:2:0.2) $R_f = 0.59$.

HPLC: $t_R$=3.06 min; YMC S-3 ODS (C-18) 6.0×150 mm, 3μ end capped column, isocratic 60% aqueous methanol containing 0.2% phosphoric acid, 25 min, 1.5 ml/min. (95.4%).

Anal. calc'd for $C_{15}H_{19}N_3O_4S_3 \cdot 0.2\ C_4H_8O_2 \cdot 0.9\ H_2O$: C,43.59; H, 5.19; N, 9.65; S, 22.09 Found: C,43.54; H, 4.89; N, 9.44; S, 21.90.

EXAMPLE 32

1000 tablets each containing the following ingredients:

| | |
|---|---|
| [4S-[4α(R*),7α,10aβ]]-Octahydro-4-[(2-mercapto-1-oxo-3-phenylpropyl)-amino]-5-oxo-7H-pyrido[2,1-b][1,3]thia-zepine-7-carboxylic acid | 100 mg. |
| Cornstarch | 100 mg. |
| Gelatin | 20 mg. |
| Avicel(microcrystalline cellulose) | 50 mg. |
| Magnesium stearate | 5 mg. |
| | 275 mg. | are prepared from sufficient bulk quantities by mixing the product of Example 3 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 100 mg. of active ingredient.

In a similar manner, tablets containing 200 mg. of the product of Examples 12, 4 to 23, 25, and 28 to 31 can be prepared.

Similar procedures can be employed to form tablets or capsules containing from 10 mg. to 500 mg. of active ingredient.

What is claimed is:

1. A compound of the formula

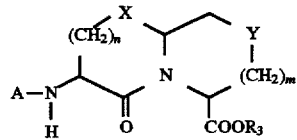

or a pharmaceutically acceptable salt thereof wherein:

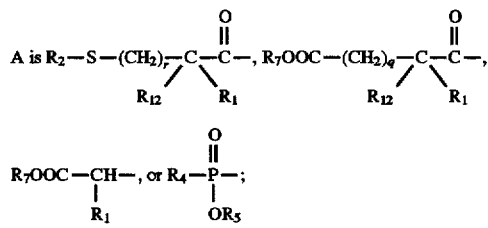

X is O or S—(O)$_t$;

$R_1$ and $R_{12}$ are independently selected from the group consisting of hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen, $$R_6-\overset{O}{\underset{\|}{C}}-,$$

or $R_{11}$—S—;

$R_3$, $R_5$ and $R_7$ are independently selected from the group consisting of hydrogen, alkyl, substituted alkyl, aryl-$(CH_2)_p$—, substituted aryl-$(CH_2)_p$—, heteroaryl-$(CH_2)_p$—,

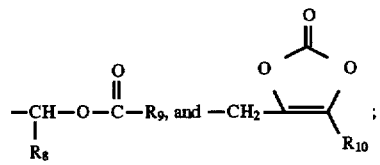

$R_4$ is alkyl, cycloalkyl-$(CH_2)_p$—, substituted alkyl, aryl-$(CH_2)_p$—, substituted aryl-$(CH_2)_p$—, or heteroaryl-$(CH_2)_p$—;

$R_6$ is alkyl, substituted alkyl, cycloalkyl-$(CH_2)_p$—, aryl-$(CH_2)_p$—, substituted aryl-$(CH_2)_p$—, or heteroaryl-$(CH_2)_p$—;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl-$(CH_2)_p$—;

$R_{11}$ is hydrogen, alkyl, substituted alkyl, cycloalkyl-$(CH_2)_p$—, aryl-$(CH_2)_p$—, substituted aryl-$(CH_2)_p$—, heteroaryl-$(CH_2)_p$—, or —S—$R_{11}$ completes a symmetrical disulfide wherein $R_{11}$ is

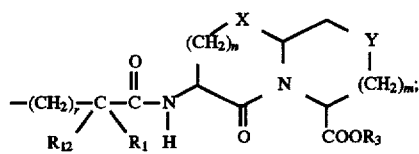

m is zero or one;

Y is $CH_2$, S—(O)$_t$, or O provided that Y is S—(O)$_t$ or O only when m is one;

n is one;

p is zero or an integer from 1 to 6;

q is zero or an integer from 1 to 3;

r is zero or one; and t is zero, one, or two.

2. A compound of claim 1 having the formula

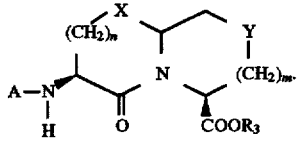

3. A compound of claim 2 wherein:

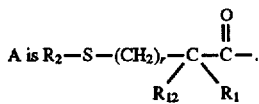

4. A compound of claim 3 wherein:

$R_2$ is hydrogen, $$R_6-\overset{\overset{O}{\|}}{C}-,$$

or $R_{11}-S-$;

$R_3$ is hydrogen or lower alkyl of 1 to 4 carbons;

r is zero or one;

$R_{11}$ is lower alkyl or 1 to 4 carbons;

$R_1$ is aryl-$CH_2-$, substituted aryl-$CH_2-$, heteroaryl-$CH_2-$, cycloalkyl-$CH_2-$ wherein cycloalkyl is of 3 to 7 carbons, or straight or branched chain alkyl of 1 to 7 carbons and $R_{12}$ is hydrogen; or $R_1$ and $R_{12}$ taken together with the carbon to which they are attached complete a cycloalkyl ring of 5 to 7 carbons;

$R_6$ is lower alkyl of 1 to 4 carbons or phenyl;

m is zero or one;

X is O or S; and

Y is $CH_2$, O, or S provided that Y is O or S only when m is one.

5. A compound of claim 3 wherein:

$R_2$ is hydrogen or $$H_3C-\overset{\overset{O}{\|}}{C}-;$$

$R_3$ is hydrogen;

r is zero or one;

$R_1$ is benzyl, cyclopropylmethyl, or straight or branched chain alkyl of 3 to 5 carbons;

$R_{12}$ is hydrogen;

m is zero or one;

X is O or S; and

Y is $CH_2$, O, or S provided that Y is O or S only when m is one.

6. A compound of claim 5 wherein:

X is S;

Y is $CH_2$; and m is one.

7. A compound of claim 6 wherein:

r is zero;

$R_2$ is hydrogen;

$R_1$ is benzyl; and $R_{12}$ is hydrogen.

8. The compound of claim 7, [3R-[3α(S*),6α,9aβ]]-hexahydro-3-[(2-mercapto-1-oxo-3-phenylpropyl)amino]-4-oxo-2H,6H-pyrido[2,1-b][1,3]thiazine-6-carboxylic acid.

9. A pharmaceutical composition useful in the treatment of cardipyascular disease such as hypertension and congestive heart failure comprising a pharmaceutically acceptable carrier and one or more compounds of the formula including a pharmaceutically acceptable salt thereof wherein A, X, Y, n, m and $R_3$ are as defined in claim 1.

10. A method of treating cardiovascular diseases such as hypertension and congestive heart failure in a mammalian species which comprises administering an effective amount of the composition of claim 9.

11. A compound of the formula or a salt thereof wherein:

n is one;

m is zero or one;

Y is $CH_2$, O, or S provided that Y is O or S only when m is one;

$R_3$ is hydrogen, lower alkyl, or aryl-$(CH_2)_p-$; and p is zero or an integer from 1 to 6.

12. A compound of claim 11 having the formula

13. The compound of claim 12 wherein:

Y is $CH_2$;

m is one; and $R_3$ is methyl.

14. A compound of the formula or a salt thereof wherein:

n is one;

m is one;

Y is $CH_2$, O or S;

$R_3$ is hydrogen, lower alkyl, or aryl-$(CH_2)_p$; and p is zero or an integer from 1 to 6.

15. A compound of claim 14 having the formula

* * * * *